(12) United States Patent
Gachango

(10) Patent No.: US 12,239,137 B2
(45) Date of Patent: Mar. 4, 2025

(54) COMPOSITIONS AND METHODS FOR CONTROLLING PLANT PESTS AND IMPROVING PLANT HEALTH

(71) Applicant: AgBiome, Inc., Durham, NC (US)

(72) Inventor: Esther Gachango, Durham, NC (US)

(73) Assignee: Ginkgo Bioworks, Inc., Boston, MA (US)

( * ) Notice: Subject to any disclaimer, the term of this patent is extended or adjusted under 35 U.S.C. 154(b) by 840 days.

(21) Appl. No.: 17/288,786

(22) PCT Filed: Oct. 29, 2019

(86) PCT No.: PCT/US2019/058581
§ 371 (c)(1),
(2) Date: Apr. 26, 2021

(87) PCT Pub. No.: WO2020/092381
PCT Pub. Date: May 7, 2020

(65) Prior Publication Data
US 2022/0000120 A1   Jan. 6, 2022

Related U.S. Application Data

(60) Provisional application No. 62/752,542, filed on Oct. 30, 2018.

(51) Int. Cl.
| | |
|---|---|
| *A01N 63/27* | (2020.01) |
| *A01N 63/22* | (2020.01) |
| *A01N 63/23* | (2020.01) |
| *A01P 3/00* | (2006.01) |
| *A01P 7/04* | (2006.01) |
| *C12N 1/20* | (2006.01) |

(52) U.S. Cl.
CPC ............ *A01N 63/27* (2020.01); *A01N 63/22* (2020.01); *A01N 63/23* (2020.01); *A01P 3/00* (2021.08); *A01P 7/04* (2021.08); *C12N 1/20* (2013.01)

(58) Field of Classification Search
None
See application file for complete search history.

(56) References Cited

U.S. PATENT DOCUMENTS

| | | |
|---|---|---|
| 5,919,447 A | 7/1999 | Marrone et al. |
| 2011/0212835 A1* | 9/2011 | Bais ............... A01N 63/22 |
| | | 504/117 |
| 2015/0335028 A1* | 11/2015 | Hellwege ........... A01N 47/34 |
| | | 424/93.46 |

FOREIGN PATENT DOCUMENTS

| | | | |
|---|---|---|---|
| EP | 1 241 247 A1 | 9/2002 | |
| JP | 2018-525420 A | 9/2018 | |
| JP | 2022-512655 A | 2/2022 | |
| WO | WO 95/28085 A1 | 10/1995 | |
| WO | WO 00/29426 A1 | 5/2000 | |
| WO | WO 2008/049230 A1 | 5/2008 | |
| WO | WO-2009060012 A2 * | 5/2009 | ............ A01N 37/46 |
| WO | WO 2017/040273 A2 | 3/2017 | |
| WO | WO 2020/077042 A1 | 4/2020 | |

OTHER PUBLICATIONS

Jouzani, G., et al., "Bacillus thuringiensis: a successful insecticide with new environmental features and tidings," *Applied Microbiology And Biotechnology*, 2017, vol. 101(7), pp. 2691-2711.

Anderson, A., et anan, "Biopesticides produced by plant-probiotic *Pseudomonas chlororaphis* isolates," *Crop Protection*, 2018, vol. 105, pp. 62-69.

Berg, G., et al., "Evaluation of potential biocontrol rhizobacteria from different host plants of *Verticillium dahlia* Kleb," *Journal of Applied Microbiology*, 2001, vol. 91, pp. 963-971.

Bi, T., et al., "New Pseudomonas chlororaphis PSJI strain having specified 16S ribosomal RNA nucleotide sequence, useful for preventing and treating banded leaf and sheath blight disease caused by Rhizoctonia solani in corn," *Clarivate Analytics*, 2017, vol. 2014(30), 1 page, abstract.

Dunaytsev, I, et al., "Phosphate-Dissolving Strain pseudomonas chlororaphis ssp chlororaphis vsk-26a3, With Fungicidal and Bactericidal Activity," *Clarivate Analytics*, 2017, vol. 2017(5), 1 page.

Hill, D., et anan, "Evaluation of AtEze for suppression of fusarium wilt of chrysanthemum," *Can J. Plant Pathol.*, 1999, vol. 21, p. 194, abstract only.

Hu, H., et al., "New Pseudomonas chlorophis HT66 useful in manufacture of bio-pesticide for preventing and treating rice sheath blight, watermelon Fusarium wilt, sweet leaf Chrysanthemum spot blight or soybean, beans, peas, sweet potato," 2017, *Clarivate Analytics*, 2017, vol. 2014(79), pp. 1-2.

(Continued)

*Primary Examiner* — Michelle F. Paguio Frising
(74) *Attorney, Agent, or Firm* — Womble Bond Dickinson (US) LLP

(57) ABSTRACT

Compositions and methods for controlling plant pests and/or improving at least one agronomic trait of interest in a plant are provided. Such compositions and methods comprise a bacterial strain that can be used as an inoculant for plants. Therefore, methods for growing a plant susceptible to a plant pest and/or plant disease caused by a plant pest and methods for controlling plant pests and/or plant disease on a plant susceptible to the plant pest and/or plant disease are also provided.

20 Claims, No Drawings

(56) References Cited

OTHER PUBLICATIONS

Lee, J., et al., "Nematicidal Activity of a Nonpathogenic Biocontrol Bacterium, *Pseudomonas chlororaphis* O6," *Curr Microbiol*, 2011, vol. 62, pp. 746-751.

Palumbo, J., et al., "Inhibition of *Aspergillus flavus* in Soil by Antagonistic *Pseudomonas* Strains Reduces the Potential for Airborne Spore Dispersal," *Phytopathology*, 2010, vol. 100(6), pp. 532-538.

Schellenberger, U., et al., "A selective insecticidal protein from *Pseudomonas* for controlling corn rootworms," *Science*, 2016, vol. 354(6312), pp. 634-637.

\* cited by examiner

COMPOSITIONS AND METHODS FOR CONTROLLING PLANT PESTS AND IMPROVING PLANT HEALTH

CROSS-REFERENCE TO RELATED APPLICATIONS

This application is a national stage filing under 35 U.S.C. 371 of PCT/US2019/058581 filed Oct. 29, 2019, which International Application was published by the International Bureau in English on May 7, 2020, and application claims priority from U.S. Provisional Patent Application No. 62/752,542, filed Oct. 30, 2018, which applications are hereby incorporated in their entirety by reference in this application.

FIELD OF THE INVENTION

The invention relates to bacterial strains and populations for controlling plant pests and/or improving an agronomic trait of interest in a plant.

BACKGROUND

Damage and diseases caused by plant pests are responsible for significant agricultural losses. Effects can range from mild symptoms to catastrophic plant damage, which can lead to major economic and social consequences. Methods are needed to effectively control plant pests.

SUMMARY

Compositions and methods for controlling plant pests and/or for improving at least one agronomic trait of interest in a plant are provided. Such compositions and methods comprise bacterial strains that control one or more plant pests, and/or improve at least one agronomic trait of interest. The bacterial strains can be used as an inoculant for plants. Also provided herein are methods for growing a plant susceptible to a plant pest or plant disease caused by a plant pest and for treating or preventing a plant disease or damage caused by a plant pest. Further provided are methods and compositions for making a modified bacterial strain having resistance to a biocide of interest.

DETAILED DESCRIPTION

I. Overview

Compositions and methods for controlling one or more plant pests and/or improving at least one agronomic trait of interest are provided. A biological agent, biocontrol agent, bacterial strain, modified bacterial strain, modified biological agent, or modified biocontrol agent or active variant thereof are used herein to describe a microorganism that is used to control plant pests and/or improve at least one agronomic trait of interest.

II. Bacterial Strains

Various biocontrol agents or bacterial strains are provided which can be used to control one or more plant pest and/or improve at least one agronomic trait of interest. Such bacterial strains include AIP045885 (a *Pseudomonas chlororaphis* strain), AIP075655 (a *Pseudomonas chlororaphis* strain), AIP009474 (a *Bacillus subtilis* strain), AIP0024525 (a *Bacillus thuringiensis* strain), AIP033287 (a *Bacillus subtilis* strain), AIP0093798 (a *Bacillus subtilis* strain), AIP061639 (a *Pseudomonas chlororaphis* strain), AIP082862 (a *Pseudomonas chlororaphis* strain), AIP058187 (a *Pseudomonas chlororaphis* strain), AIP059286 (a *Pseudomonas chlororaphis* strain), and AIP036706 (a *Pseudomonas chlororaphis* strain). Cell populations comprising one or more of AIP045885, AIP075655, AIP09474, AIP024525, AIP033287, AIP093798, AIP061639, AIP082862, AIP058187, AIP059286, and AIP036706 are provided, as well as, populations of spores derived from each of these strains, or any preparation thereof.

Thus, various bacterial strains and/or the pesticidal compositions provided herein comprise as an active ingredient a cell population comprising one or more of AIP045885, AIP075655, AIP09474, AIP024525, AIP033287, AIP093798, AIP061639, AIP082862, AIP058187, AIP059286, and AIP036706, or an active variant of any thereof.

AIP045885 was deposited with the Patent Depository of the National Center for Agricultural Utilization Research Agricultural Research Service, U.S. Department of Agriculture, 1815 North University Street, Peoria, Illinois 61604 U.S.A. on Aug. 3, 2018 and assigned NRRL No. B-67650.

AIP075655 was deposited with the Patent Depository of the National Center for Agricultural Utilization Research Agricultural Research Service, U.S. Department of Agriculture, 1815 North University Street, Peoria, Illinois 61604 U.S.A. on Aug. 3, 2018 and assigned NRRL No. B-67651.

AIP009474 was deposited with the Patent Depository of the National Center for Agricultural Utilization Research Agricultural Research Service, U.S. Department of Agriculture, 1815 North University Street, Peoria, Illinois 61604 U.S.A. on Aug. 3, 2018 and assigned NRRL No. B-67657.

AIP024525 was deposited with the Patent Depository of the National Center for Agricultural Utilization Research Agricultural Research Service, U.S. Department of Agriculture, 1815 North University Street, Peoria, Illinois 61604 U.S.A. on Aug. 3, 2018 and assigned NRRL No. B-67661.

AIP033287 was deposited with the Patent Depository of the National Center for Agricultural Utilization Research Agricultural Research Service, U.S. Department of Agriculture, 1815 North University Street, Peoria, Illinois 61604 U.S.A. on Aug. 3, 2018 and assigned NRRL No. B-67659.

AIP093798 was deposited with the Patent Depository of the National Center for Agricultural Utilization Research Agricultural Research Service, U.S. Department of Agriculture, 1815 North University Street, Peoria, Illinois 61604 U.S.A. on Aug. 3, 2018 and assigned NRRL No. B-67660.

AIP061639 was deposited with the Patent Depository of the National Center for Agricultural Utilization Research Agricultural Research Service, U.S. Department of Agriculture, 1815 North University Street, Peoria, Illinois 61604 U.S.A. on Aug. 3, 2018 and assigned NRRL No. B-67654.

AIP082862 was deposited with the Patent Depository of the National Center for Agricultural Utilization Research Agricultural Research Service, U.S. Department of Agriculture, 1815 North University Street, Peoria, Illinois 61604 U.S.A. on Aug. 3, 2018 and assigned NRRL No. B-67656.

AIP058187 was deposited with the Patent Depository of the National Center for Agricultural Utilization Research Agricultural Research Service, U.S. Department of Agriculture, 1815 North University Street, Peoria, Illinois 61604 U.S.A. on Aug. 3, 2018 and assigned NRRL No. B-67655.

AIP059286 was deposited with the Patent Depository of the National Center for Agricultural Utilization Research Agricultural Research Service, U.S. Department of Agriculture, 1815 North University Street, Peoria, Illinois 61604 U.S.A. on Aug. 3, 2018 and assigned NRRL No. B-67653.

AIP036706 was deposited with the Patent Depository of the National Center for Agricultural Utilization Research Agricultural Research Service, U.S. Department of Agriculture, 1815 North University Street, Peoria, Illinois 61604 U.S.A. on Aug. 3, 2018 and assigned NRRL No. B-67652.

Each of the deposits identified above will be maintained under the terms of the Budapest Treaty on the International Recognition of the Deposit of Microorganisms for the Purposes of Patent Procedure. Each deposit was made merely as a convenience for those of skill in the art and is not an admission that a deposit is required under 35 U.S.C. § 112.

The term "isolated" encompasses a bacterium, spore, or other entity or substance, that has been (1) separated from at least some of the components with which it was associated when initially produced (whether in nature or in an experimental setting), and/or (2) produced, prepared, purified, and/or manufactured by the hand of man. Isolated bacteria may be separated from at least about 10%, about 20%, about 30%, about 40%, about 50%, about 60%, about 70%, about 80%, about 90%, or more of the other components with which they were initially associated.

As used herein, a substance is "pure" if it is substantially free of other components. The terms "purify," "purifying" and "purified" refer to a bacterium, spore, or other material that has been separated from at least some of the components with which it was associated either when initially produced or generated (e.g., whether in nature or in an experimental setting), or during any time after its initial production. A bacterium or spore or a bacterial population or a spore population may be considered purified if it is isolated at or after production, such as from a material or environment containing the bacterium or bacterial population or spore, and a purified bacterium or bacterial population or spore may contain other materials up to about 10%, about 20%, about 30%, about 40%, about 50%, about 60%, about 70%, about 80%, about 90%, or above about 90% and still be considered purified. In some embodiments, purified bacteria or spores and bacterial populations or spore populations are more than about 80%, about 85%, about 90%, about 91%, about 92%, about 93%, about 94%, about 95%, about 96%, about 97%, about 98%, about 99%, or more than about 99% pure. In specific embodiments, a culture of bacteria contains no other bacterial species in quantities to be detected by normal bacteriological techniques.

In some embodiments, the compositions of the invention comprise substantially pure cultures of bacterial strain AIP045885, AIP075655, AIP09474, AIP024525, AIP033287, AIP093798, AIP061639, AIP082862, AIP058187, AIP059286, or AIP036706. The compositions of the invention also provide progeny of substantially pure cultures of bacterial strain AIP045885, AIP075655, AIP09474, AIP024525, AIP033287, AIP093798, AIP061639, AIP082862, AIP058187, AIP059286, or AIP036706, wherein the culture has all of the physiological and morphological characteristics of AIP045885, AIP075655, AIP09474, AIP024525, AIP033287, AIP093798, AIP061639, AIP082862, AIP058187, AIP059286, or AIP036706, respectively. By "population" is intended a group or collection that comprises two or more individuals (i.e., 10, 100, 1,000, 10,000, $1 \times 10^6$, $1 \times 10^7$, or $1 \times 10^8$ or greater) of a given bacterial strain. Various compositions are provided herein that comprise a population of at least one bacterial strain or a mixed population of individuals from more than one bacterial strain. In specific embodiments, the population of at least one of a bacterial strain (i.e., cells of AIP045885, AIP075655, AIP09474, AIP024525, AIP033287, AIP093798, AIP061639, AIP082862, AIP058187, AIP059286, and AIP036706, or an active variant of any thereof, or spores or forespores or a combination of cells, forespores and/or spores, formed from one or more of AIP045885, AIP075655, AIP09474, AIP024525, AIP033287, AIP093798, AIP061639, AIP082862, AIP058187, AIP059286, and AIP036706, or an active variant of any thereof) comprises a concentration of at least about $10^5$ CFU/ml to about $10^{11}$ CFU/ml, about $10^5$ CFU/ml to about $10^{10}$ CFU/ml, about $10^5$ CFU/ml to about $10^{12}$ CFU/ml, about $10^5$ CFU/ml to about $10^6$ CFU/ml, about $10^6$ CFU/ml to about $10^7$ CFU/ml, about $10^7$ CFU/ml to about $10^8$ CFU/ml, about $10^8$ CFU/ml to about $10^9$ CFU/ml, about $10^9$ CFU/ml to about $10^{10}$ CFU/ml, about $10^{10}$ CFU/ml to about $10^{11}$ CFU/ml, about $10^{11}$ CFU/ml to about $10^{12}$ CFU/ml. In other embodiments, the concentration of the bacterial strain provided herein or active variant thereof comprises at least about $10^5$ CFU/ml, at least about $10^6$ CFU/ml, at least about $10^7$ CFU/ml, at least about $10^8$ CFU/ml, at least about $10^9$ CFU/ml, at least about $10^{10}$ CFU/ml, at least about $10^{11}$ CFU/ml, or at least about $10^{12}$ CFU/ml.

A "spore" refers to at least one dormant (at application) but viable reproductive unit of a bacterial species. Non-limiting methods by which spores are formed from each of AIP045885, AIP075655, AIP09474, AIP024525, AIP033287, AIP093798, AIP061639, AIP082862, AIP058187, AIP059286, and AIP036706 (or variants of any thereof) are disclosed elsewhere herein. It is further recognized the populations disclosed herein can comprise a combination of vegetative cells and forepores (cells in an intermediate stage of spore formation); a combination of forespores and spores; or a combination of forespores, vegetative cells and/or spores.

As used herein, "derived from" means directly isolated or obtained from a particular source or alternatively having identifying characteristics of a substance or organism isolated or obtained from a particular source. In the event that the "source" is an organism, "derived from" means that it may be isolated or obtained from the organism itself or culture broth, suspension, or medium used to culture or grow said organism. A compound or composition "derived from" or "obtainable from" means that the compound or composition may be isolated from or produced by a cell culture or a whole cell broth, or suspension, filtrate, supernatant, fraction, or extract derived from a cell culture or a whole cell broth.

As used herein, "whole broth culture" or whole cell broth" refers to a liquid culture containing both cells and media. If bacteria are grown on a plate, the cells can be harvested in water or other liquid, whole culture. The terms "whole broth culture" and "whole cell broth" are used interchangeably.

As used herein, "supernatant" refers to the liquid remaining when cells grown in broth or are harvested in another liquid from an agar plate and are removed by centrifugation, filtration, sedimentation, or other means well known in the art. In some embodiments, the supernatant may be diluted with another composition, such as water, buffer, fresh media, and/or a formulation. The diluted supernatant is still considered a supernatant of the invention.

As used herein, "filtrate" refers to liquid from a whole broth culture that has passed through a membrane. The filtrate may comprise a concentrated amount of an effective compound or metabolite compared to the concentration of the effective compound or metabolite in the whole broth culture or supernatant. As used herein, "extract" refers to liquid substance removed from cells by a solvent (water, detergent, buffer, and/or organic solvent, for example) and separated from the cells by centrifugation, filtration, or other method known in the art. The extract may comprise a concentrated amount of an effective compound or metabolite compared to the concentration of the effective compound or metabolite in the cells prior to extraction. Alternatively, the filtrate or extract may then be diluted with another composition, such as water, buffer, fresh media, and/or a formulation. Such diluted filtrates or extracts are still considered filtrates and extracts of the invention.

As used herein, "metabolite" refers to a compound, substance, or byproduct of fermentation of a bacterial strain (i.e., at least one of AIP045885, AIP075655, AIP09474, AIP024525, AIP033287, AIP093798, AIP061639, AIP082862, AIP058187, AIP059286, AIP036706, or an active variant of any thereof). An effective compound or metabolite is a compound present in the supernatant, whole cell broth, or bacterial strain which may improve any agronomic trait of interest of a plant, or controls a plant pest or plant pathogen that causes a plant disease, when applied to a plant of interest at an effective amount.

In some embodiments, a composition of the invention comprises a filtrate or extract derived from fermentation of a bacterial strain, wherein said composition comprises a concentrated amount of an effective compound or metabolite compared to the amount in a whole cell broth or supernatant of said bacterial strain, wherein the bacterial is at least one of AIP045885, AIP075655, AIP09474, AIP024525, AIP033287, AIP093798, AIP061639, AIP082862, AIP058187, AIP059286, AIP036706, or an active variant of any thereof. In other embodiments, a compositions of the invention comprises a diluted filtrate, diluted extract, or diluted supernatant derived from the fermentation of a bacterial strain, wherein said composition comprises a diluted amount of the effective compound or metabolite compared to the amount whole cell broth or undiluted supernatant of said bacterial strain, wherein the bacterial is at least one of AIP045885, AIP075655, AIP09474, AIP024525, AIP033287, AIP093798, AIP061639, AIP082862, AIP058187, AIP059286, AIP036706, or an active variant of any thereof. The diluted filtrate, diluted extract, or diluted supernatant may still comprise an effective amount of the effective compound or metabolite.

The compositions and methods described herein comprise or are derived from a bacterial strain (i.e., at least one of AIP045885, AIP075655, AIP09474, AIP024525, AIP033287, AIP093798, AIP061639, AIP082862, AIP058187, AIP059286, AIP036706, or an active variant of any thereof, or a spore or a forespore or a combination of cells, forespores or/and spores, from any one of AIP045885, AIP075655, AIP09474, AIP024525, AIP033287, AIP093798, AIP061639, AIP082862, AIP058187, AIP059286, AIP036706, or an active variant of any thereof). Methods comprise cultivating at least one of these bacterial strains. In some embodiments, at least one of these bacterial strains is cultivated and compounds and/or compositions are obtained by isolating these compounds and/or compositions from the culture of at least one of these bacterial strains.

In some embodiments, at least one bacterial strain is cultivated in nutrient medium using methods known in the art. The bacterial strain can be cultivated by shake flask cultivation or by small scale or large scale fermentation (including but not limited to continuous, batch, fed-batch, or solid state fermentation) in laboratory or industrial fermenters performed in a suitable medium and under conditions allowing for bacterial cell growth. The cultivation can take place in suitable nutrient medium comprising carbon and nitrogen sources and inorganic salts, using procedures known in the art. Suitable media are available from commercial sources or are prepared according to publications well-known in the art.

Following cultivation, compounds, metabolites, and/or compositions can be extracted from the culture broth. The extract can be fractionated by chromatography. The extract can be further purified using methods well-known in the art. The extract can also be diluted using methods well-known in the art.

The compositions comprising a cell of a bacterial strain (i.e., at least one of AIP045885, AIP075655, AIP09474, AIP024525, AIP033287, AIP093798, AIP061639, AIP082862, AIP058187, AIP059286, and AIP036706 or an active variant of any thereof, or a spore or a forespore or a combination of cells, forespores and/or spores, and/or a composition derived from any one of AIP045885, AIP075655, AIP09474, AIP024525, AIP033287, AIP093798, AIP061639, AIP082862, AIP058187, AIP059286, and AIP036706, or an active variant of any thereof) can further comprise an agriculturally acceptable carrier. The term "agriculturally acceptable carrier" is intended to include any material that facilitates application of a composition to the intended subject (i.e., a plant or plant part susceptible to damage or disease caused by a plant pest or a plant or plant part for improving an agronomic trait of interest). Carriers used in compositions for application to plants and plant parts are preferably non-phytotoxic or only mildly phytotoxic. A suitable carrier may be a solid, liquid or gas depending on the desired formulation. In one embodiment, carriers include polar or non-polar liquid carriers such as water, mineral oils and vegetable oils. Additional carriers are disclosed elsewhere herein.

A. Active Variants of a Bacterial Strain

Further provided are active variants of AIP045885, AIP075655, AIP09474, AIP024525, AIP033287, AIP093798, AIP061639, AIP082862, AIP058187, AIP059286, and AIP036706. Such variants will retain the ability to control one or more plant pests or improve one or more agronomic traits of interest in a plant. Thus, in some embodiments, the active variants of the bacterial strains provided herein will retain pesticidal activity against a plant pest. As used herein, "pesticidal activity" refers to activity against one or more pests, including insects, fungi, bacteria, nematodes, viruses or viroids, protozoan pathogens, and the like, such that the pest is killed or controlled. In some embodiments, variants will retain the ability to control one or more insect pests or nematode pests. In particular embodiments, variants will retain the ability to control coleopteran insect pests, including corn rootworms (e.g., Western corn rootworm), Colorado potato beetle, weevils (e.g., sweet potato weevil), or hemipteran insect pests.

Active variants of the various bacterial strains provided herein include, for example, any isolate or mutant of AIP045885, AIP075655, AIP09474, AIP024525, AIP033287, AIP093798, AIP061639, AIP082862, AIP058187, AIP059286, and AIP036706.

The term "mutant" refers to a variant of the parental strain as well as methods for obtaining a mutant or variant in which the pesticidal activity is greater than that expressed by the parental strain. The "parent strain" is the original strain before mutagenesis. To obtain such mutants the parental strain may be treated with a chemical such as N-methyl-N'-nitro-N-nitrosoguanidine, ethylmethanesulfone (EMS), or by irradiation using gamma, x-ray, or UV-irradiation, or by other means well known in the art.

In some embodiments, the active variant contains at least mutation in at least one gene, relative to the deposited strain.

The gene(s) may have a role in, for example, biofilm formation, motility, chemotaxis, extracellular secretion, transport (for example ABC transporter proteins), stress responses, volatiles, transcription (for example alternative sigma factors and global transcription regulators), root colonization, ability to stimulate induced systemic resistance in a plant, and/or secondary metabolism including synthesis of lipopeptides, polyketides, macromolecular hydrolases (for example proteases and/or carbohydrases), and/or antimicrobial compounds including antibiotics. Secondary metabolism refers to both non-ribosomal and ribosomal synthesis of antimicrobial compounds, including cyclic lipopeptides, polyketides, iturins, bacteriocins (for example plantazolicin and amylocyclicin) and dipeptides (for example bacilysin).

An example of an active variant is a cell of bacterial strain AIP045885, AIP075655, AIP09474, AIP024525, AIP033287, AIP093798, AIP061639, AIP082862, AIP058187, AIP059286, or AIP036706, wherein the cell further comprises a mutation in the swrA gene that results in loss of function. The swrA mutation, which affects biofilm formation (Kearns et al., Molecular Microbiology (2011) 52(2): 357-369) may result in an active variant of a strain of the invention which has enhanced ability to control a plant pest or improve an agronomic trait of interest of a plant. Other genes that are involved in biofilm formation, such as sfp, epsC, degQ, and a plasmid gene called rapP (see for example, McLoon et al., J of Bacteriology, (2011) 193(8): 2027-2034), may also be mutated in an active variant of a bacterial strain of the invention.

In specific embodiments, the bacterial strain is compatible with a biocide. A biocide is a chemical substance that can exert a controlling effect on an organism by chemical or biological means. Biocides include pesticides, such as fungicides or insecticides; herbicides; other crop protection chemicals, and the like. Such compounds are discussed in detail elsewhere herein. A bacterial strain is compatible with a biocide when the bacterial strain is able to survive and/or reproduce in the presence of an effective amount of a biocide of interest. In instances where the bacterial strain is not compatible with a biocide of interest, if desired, methods can be undertaken to modify the bacterial strain to impart the compatibility of interest. Such methods to produce modified bacterial strains include both selection techniques and/or transformation techniques.

By "modified bacterial strain" is intended a population wherein the strain has been modified (by selection and/or transformation) to have one or more additional traits of interest. In some cases the modified bacterial strain comprises any one of AIP045885, AIP075655, AIP09474, AIP024525, AIP033287, AIP093798, AIP061639, AIP082862, AIP058187, AIP059286, and AIP036706, or an active variant of any thereof. In specific embodiments, the modified bacterial strain is compatible with a biocide of interest, including but not limited to, resistance to a herbicide, fungicide, pesticide, or other crop protection chemical. The modified biocide-resistant strains have the same identification characteristics as the original sensitive strain except they are significantly more resistant to the particular herbicide, fungicide, pesticide, or other crop protection chemical. Their identification is readily possible by comparison with characteristics of the known sensitive strain. Thus, isolated populations of modified bacterial strains are provided.

An increase in resistance to a biocide (e.g., a herbicide, insecticide, fungicide, pesticide, or other crop protection chemical resistance) refers to the ability of an organism (e.g., bacterial cell or spore) to survive and reproduce following exposure to a dose of the biocide (e.g, herbicide, insecticide, fungicide, pesticide, or other crop protection chemical) that would normally be lethal to the unmodified organism or would substantially reduce growth of the unmodified organism. In specific embodiments, the increase in resistance to a biocide is demonstrated in the presence of an agriculturally effective amount of the biocide.

In such instances, the modified bacterial strain having resistance to one or more biocides is useful for enhancing the competitiveness of bacterial strains particularly over other microbial agents which are not resistant to herbicides, insecticides, fungicides, pesticides, or other crop protection chemicals. Therefore, compositions provided herein include selected or engineered bacterial strains and modified populations of bacterial strains. These bacterial strains or modified bacterial strains can be used as an inoculant for plants. They can also be applied as a spray application directly to the aerial parts of plants or can be applied as a seed coating, and can be mixed with the herbicide or other chemical to which they have been modified to become tolerant.

Thus, active variants of the bacterial strains disclosed herein, include for example, a modified strain, such that the active variant controls a plant pest and further is able to grow in the presence of at least one biocide. Recombinant bacterial strains having resistance to an herbicide, insecticide, fungicide, pesticide, or other crop protection chemical can be made through genetic engineering techniques and such engineered or recombinant bacterial strains grown to produce a modified population of bacterial strains. A recombinant bacterial strain is produced by introducing polynucleotides into the bacterial host cell by transformation. Methods for transforming microorganisms are known and available in the art. See, generally, Hanahan, D. (1983) Studies on transformation of *Escherichia coli* with plasmids *J. Mol. Biol.* 166, 557-77; Seidman, C. E. (1994) In: *Current Protocols in Molecular Biology*, Ausubel, F. M. et al. eds., John Wiley and Sons, NY; Choi et al. (2006) J. Microbiol. Methods 64:391-397; Wang et al. 2010. *J. Chem. Technol. Biotechnol.* 85:775-778. Transformation may occur by natural uptake of naked DNA by competent cells from their environment in the laboratory. Alternatively, cells can be made competent by exposure to divalent cations under cold conditions, by electroporation, by exposure to polyethylene glycol, by treatment with fibrous nanoparticles, or other methods well known in the art.

Herbicide resistance genes for use in transforming a recombinant bacterial strain include, but are not limited to, fumonisin detoxification genes (U.S. Pat. No. 5,792,931); acetolactate synthase (ALS) mutants that lead to herbicide resistance, in particular the sulfonylurea-type herbicides, such as the S4 and/or Hra mutations; inhibitors of glutamine synthase such as phosphinothricin or basta (e.g., bar gene); and glyphosate resistance (EPSPS gene); gluphosinate, and HPPD resistance (WO 96/38576, U.S. Pat. Nos. 6,758,044; 7,250,561; 7,935,869; and 8,124,846), or other such genes known in the art. The disclosures of WO 96/38576, U.S. Pat. Nos. 5,792,931, 6,758,044; 7,250,561; 7,935,869; and 8,124,846 are herein incorporated by reference. The bar gene encodes resistance to the herbicide basta, the nptII gene encodes resistance to the antibiotics kanamycin and geneticin, and the ALS-gene mutants encode resistance to the sulfonylurea herbicides including chlorsulfuron, metsulfuron, sulfometuron, nicosulfuron, rimsulfuron, flazasulfuron, sulfosulfuron, and triasulfuron, and the imadizolinone herbicides including imazethapyr, imazaquin, imazapyr, and imazamethabenz.

To identify and produce a modified population of bacterial strains through selection, the bacterial strains are grown in the presence of the herbicide, insecticide, fungicide, pesticide, or other crop protection chemical as the selection pressure. Susceptible agents are killed while resistant agents survive to reproduce without competition. As the bacterial strains are grown in the presence of the herbicide, insecticide, fungicide, pesticide, or other crop protection chemical, resistant bacterial strains successfully reproduce and become dominant in the population, becoming a modified population of bacterial strains. Methods for selecting resistant strains are known and include U.S. Pat. Nos. 4,306,027 and 4,094,097, herein incorporated by reference. The active variant of the bacterial strain comprising a modified population of bacterial strains will have the same identification characteristics as the original sensitive strain except they are significantly more tolerant to the particular herbicide, insecticide, fungicide, pesticide, or other crop protection chemical. Thus, their identification is readily possible by comparison with characteristics of the known sensitive strain.

Further active variants of the various bacteria provided herein can be identified employing, for example, methods that determine the sequence identity relatedness between the 16S ribosomal RNA, methods to identify groups of derived and functionally identical or nearly identical strains include Multi-locus sequence typing (MLST), concatenated shared genes trees, Whole Genome Alignment (WGA), Average Nucleotide Identity, and MinHash (Mash) distance metric.

In one aspect, the active variants of the bacterial strain AIP045885, AIP075655, AIP09474, AIP024525, AIP033287, AIP093798, AIP061639, AIP082862, AIP058187, AIP059286, and AIP036706 include strains that are closely related to any of the disclosed strains by employing the Bishop MLST method of organism classification as defined in Bishop et al. (2009) *BMC Biology* 7(1)1741-7007-7-3. Thus, in specific embodiments, an active variant of a bacterial strain disclosed herein includes a bacterial strain that falls within at least a 80%, 85%, 86%, 87%, 88%, 89%, 90%, 91%, 92%, 93%. 94%, 95%, 96%, 97%, 98%, 98.5%, 98.8%, 99%, 99.1%, 99.2%, 99.3%, 99.4%, 99.5%, 99.6%, 99.7%, 99.8%, or 99.9% sequence cut off employing the Bishop method of organism classification as set forth in Bishop et al. (2009) *BMC Biology* 7(1)1741-7007-7-3, which is herein incorporated by reference in its entirety. Active variants of the bacteria identified by such methods will retain the ability to control at least one plant pest and/or to improve at least one agronomic trait when applied in an effective amount to a plant, plant part, or an area of cultivation, including for example reducing plant pests, reducing infestations of plant pests, and/or increasing pest resistance including insect pest resistance (e.g., Coleoptera insects such as Western corn rootworm, Colorado potato beetle, and/or sweet potato weevil).

In another aspect, the active variant of the bacterial strain(s) disclosed herein include strains that are closely related to any of the disclosed strains on the basis of the Average Nucleotide Identity (ANI) method of organism classification. ANI (see, for example, Konstantinidis, K. T., et al., (2005) *PNAS USA* 102(7):2567-72; and Richter, M., et al., (2009) *PNAS* 106(45):19126-31) and variants (see, for example, Varghese, N. J., et al., *Nucleic Acids Research* (Jul. 6, 2015): gkv657) are based on summarizing the average nucleotides shared between the genomes of strains that align in WGAs. Thus, in specific embodiments, an active variant of bacterial strain AIP045885, AIP075655, AIP09474, AIP024525, AIP033287, AIP093798, AIP061639, AIP082862, AIP058187, AIP059286, and AIP036706 disclosed herein includes a bacterial strain that falls within at least a 90%, 95%, 96%, 97%, 97.5%, 98%, 98.5%, 98.8%, 99%, 99.5%, or 99.8% sequence cut off employing the ANI method of organism classification as set forth in Konstantinidis, K. T., et al., (2005) *PNAS USA* 102(7):2567-72, which is herein incorporated by reference in its entirety. Active variants of the bacteria identified by such methods will retain the ability to control at least one plant pest and/or to improve at least one agronomic trait when applied in an effective amount to a plant, plant part, or an area of cultivation, including for example, reducing plant pests, reducing infestations of plant pests, and/or increasing pest resistance including insect pest resistance (e.g., Coleoptera insects such as Western corn rootworm, Colorado potato beetle, and/or sweet potato weevil).

In another aspect, the active variants of the isolated bacterial strain(s) disclosed herein include strain(s) that are closely related to any of the above strains (for example, closely related to AIP045885, AIP075655, AIP09474, AIP024525, AIP033287, AIP093798, AIP061639, AIP082862, AIP058187, AIP059286, or AIP036706) on the basis of 16S rDNA sequence identity. See Stackebrandt E, et al., "Report of the ad hoc committee for the re-evaluation of the species definition in bacteriology," *Int J Syst Evol Microbiol.* 52(3):1043-7 (2002) regarding use of 16S rDNA sequence identity for determining relatedness in bacteria. In an embodiment, the active variant is at least 95% identical to any of the above strains on the basis of 16S rDNA sequence identity, at least 96% identical to any of the above strains on the basis of 16S rDNA sequence identity, at least 97% identical to an of the above strains on the basis of 16S rDNA sequence identity, at least 98% to any of the above strains on the basis of 16S rDNA sequence identity, at least 98.5% identical to any of the above strains on the basis of 16S rDNA sequence identity, at least 99% identical to any of the above strains on the basis of 16S rDNA sequence identity, at least 99.5% to any of the above strains on the basis of 16S rDNA sequence identity or at least 100% to any of the above strains on the basis of 16S rDNA sequence identity. Active variants of the bacteria identified by such methods will retain the ability to control at least one plant pest and/or to improve at least one agronomic trait when applied in an effective amount to a plant, plant part, or an area of cultivation, including for example, reducing plant pests, reducing infestations of plant pests, and/or increasing pest resistance including insect pest resistance (e.g., Coleoptera insects such as Western corn rootworm, Colorado potato beetle, and/or sweet potato weevil).

The MinHash (Mash) distance metric is a comparison method that defines thresholds for hierarchical classification of microorganisms at high resolution and requires few parameters and steps (Ondov et al. (2016) *Genome Biology* 17:132). The Mash distance estimates the mutation rate between two sequences directly from their MinHash sketches (Ondov et al. (2016) *Genome Biology* 17:132). Mash distance strongly corresponds to Average Nucleotide Identity method (ANI) for hierarchical classification (See, Konstantinidis, K. T. et al. (2005) PNAS USA 102(7):2567-72, herein incorporated by reference in its entirety). That is, an ANI of 97% is approximately equal to a Mash distance of 0.03, such that values put forth as useful classification thresholds in the ANI literature can be directly applied with the Mash distance.

Active variants of the bacterial strain(s) disclosed herein include strains that are closely related to AIP045885, AIP075655, AIP09474, AIP024525, AIP033287, AIP093798, AIP061639, AIP082862, AIP058187, AIP059286, or AIP036706 on the basis of the Minhash (Mash) distance between complete genome DNA sequences. Thus, in specific embodiments, an active variant of a bacterial strain disclosed herein includes bacterial strains having a genome within a Mash distance of less than about 0.015 to the disclosed strains. In other embodiments, an active variant of a bacterial strain disclosed herein includes a distance metric of less than about 0.001, 0.0025, 0.005, 0.010, 0.015, 0.020, 0.025, or 0.030. A genome, as it relates to the Mash distance includes both bacterial chromosomal DNA and bacterial plasmid DNA. In other embodiments, the active variant of a bacterial strain has a genome that is above a Mash distance threshold to the disclosed strains that is greater than dissimilarity caused by technical variance. In further instances, the active variant of a bacterial strain has a genome that is above a Mash distance threshold to the disclosed strains that is greater than dissimilarity caused by technical variance and has a Mash distance of less than about 0.015. In other instances, the active variant of a bacterial strain has a genome that is above a Mash distance threshold to the disclosed strains that is greater than dissimilarity caused by technical variance and has a Mash distance of less than about 0.001, 0.0025, 0.005, 0.010, 0.015, 0.020, 0.025, or 0.030.

As used herein, "above technical variation" means above the Mash distance between two strains caused by errors in the genome assemblies provided the genomes being compared were each DNA sequenced with at least 20× coverage with the Illumina HiSeq 2500 DNA sequencing technology and the genomes are at least 99% complete with evidence for contamination of less than 2%. While 20× coverage is an art recognized term, for clarity, an example of 20× coverage is as follows: for a genome size of 5 megabases (MB), 100 MB of DNA sequencing from the given genome is required to have 20× sequencing coverage on average at each position along the genome. There are many suitable collections of marker genes to use for genome completeness calculations including the sets found in Campbell et al. (2013) *PNAS USA* 110(14):5540-45, Dupont et al. (2012) *ISMEJ* 6:1625-1628, and the CheckM framework (Parks et al. (2015) *Genome Research* 25:1043-1055); each of these references is herein incorporated in their entirety. Contamination is defined as the percentage of typically single copy marker genes that are found in multiple copies in the given genome sequence (e.g. Parks et al. (2015) *Genome Research* 25:1043-1055); each of these references is herein incorporated in their entirety. Completeness and contamination are calculated using the same collection of marker genes. Unless otherwise stated, the set of collection markers employed in the completeness and contamination assay is those set forth in Campbell et al. (2013) *PNAS USA* 110(14):5540-45, herein incorporated by reference.

Exemplary steps to obtain a distance estimate between the genomes in question are as follows: (1) Genomes of sufficient quality for comparison must be produced. A genome of sufficient quality is defined as a genome assembly created with enough DNA sequence to amount to at least 20× genome coverage using Illumina HiSeq 2500 technology. The genome must be at least 99% complete with contamination of less than 2% to be compared to the claimed microbe's genome. (2) Genomes are to be compared using the Minhash workflow as demonstrated in Ondov et al. (2016) *Genome Biology* 17:132, herein incorporated by reference in its entirety. Unless otherwise stated, parameters employed are as follows: "sketch" size of 1000, and "k-mer length" of 21. (3) Confirm that the Mash distance between the two genomes is less than 0.001, 0.0025, 0.005, 0.010, 0.015, 0.020, 0.025, or 0.030. Using the parameters and methods stated above, a Mash distance of 0.015 between two genomes means the expected mutation rate is 0.015 mutations per homologous position. Active variants of the bacteria identified by such methods will retain the ability to control at least one plant pest and/or to improve at least one agronomic trait when applied in an effective amount to a plant, plant part, or an area of cultivation, including for example, reducing plant pests, reducing infestations of plant pests, and/or increasing pest resistance including insect pest resistance (e.g., Coleoptera insects such as Western corn rootworm, Colorado potato beetle, and/or sweet potato weevil).

III. Formulations

The bacterial strains provided herein (i.e., cells of AIP045885, AIP075655, AIP09474, AIP024525, AIP033287, AIP093798, AIP061639, AIP082862, AIP058187, AIP059286, AIP036706, or active variants of any thereof, or a spore or a forespore or a combination of cells, forespores and/or spores, and/or a composition derived from any one of AIP045885, AIP075655, AIP09474, AIP024525, AIP033287, AIP093798, AIP061639, AIP082862, AIP058187, AIP059286, AIP036706, or an active variant of any thereof) can be formulated as a cell paste, wettable powders, a cell pellet, dusts, granules, a slurry, a dry powder, aqueous or oil based liquid products, and the like. Such formulations will comprise the bacteria provided herein or an active variant thereof, and/or a composition derived therefrom in addition to carriers and other agents. The formulations can be used in a variety of methods as disclosed elsewhere herein.

The bacterial strains disclosed herein and the active variants thereof can be formulated to include at least one or more of an extender, a solvent, spontaneity promoter, carrier, emulsifier, dispersant, frost protectant, thickener, and/or adjuvant. In some embodiments, the extender, solvent, spontaneity promoter, carrier, emulsifier, dispersant, frost protectant, thickener, and/or adjuvant is a non-natural or synthetic extender, a solvent, spontaneity promoters, carriers, emulsifiers, dispersants, frost protectants, thickeners, and/or adjuvants. In particular embodiments, the bacterial strains disclosed herein and the active variants thereof can be formulated to include at least one or more natural extender, a solvent, spontaneity promoter, carrier, emulsifier, dispersant, frost protectant, thickener, and/or adjuvant.

Examples of typical formulations include water-soluble liquids (SL), emulsifiable concentrates (EC), emulsions in water (EW), suspension concentrates (SC), suspo-emulsions (SE), flowable concentrates for seed treatment (FS), oil dispersions (OD), water-dispersible granules (WG), granules (GR), capsule concentrates (CS), water-dispersible granules (WG), granules (GR), block baits (BB), water-soluble granules (SG), and mixed formulations of CS and SC (ZC). These and other possible types of formulation are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations may comprise active agrochemical compounds other than one or more active compounds of the invention.

The formulations or application forms of the various bacterial strains or active variants thereof can comprise, but are not limited to, auxiliaries, such as extenders, solvents, spontaneity promoters, carriers, emulsifiers, dispersants, frost protectants, biocides, solid carriers, surfactants, thickeners and/or other auxiliaries, such as adjuvants. An adjuvant in this context is a component which enhances the biological effect of the formulation, without the component itself having a biological effect. Examples of adjuvants are agents which promote the retention, spreading, attachment to the leaf surface, or penetration.

Non-limiting extenders are, for example, water, polar and nonpolar organic chemical liquids, for example from the classes of the aromatic and non-aromatic hydrocarbons (such as paraffins, alkyl benzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide). If the extender used is water, it is also possible to employ, for example, organic solvents as auxiliary solvents. Essentially, non-limiting liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water. In principle it is possible to use any suitable solvent. Non-limiting solvents are, for example, aromatic hydrocarbons, such as xylene, toluene or alkylnaphthalenes, for example, chlorinated aromatic or aliphatic hydrocarbons, such as chlorobenzene, chloroethylene or methylene chloride, for example, aliphatic hydrocarbons, such as cyclohexane, for example, paraffins, petroleum fractions, mineral and vegetable oils, alcohols, such as methanol, ethanol, isopropanol, butanol or glycol, for example, and also their ethers and esters, ketones such as acetone, methyl ethyl ketone, methyl isobutyl ketone or cyclohexanone, for example, strongly polar solvents, such as dimethyl sulphoxide, and water.

Non-limiting examples of suitable carriers include, for example, ammonium salts and ground natural minerals such as kaolins, clays, talc, chalk, quartz, attapulgite, montmorillonite or diatomaceous earth, and ground synthetic minerals, such as finely divided silica, alumina and natural or synthetic silicates, resins, waxes and/or solid fertilizers. Mixtures of such carriers may likewise be used. Carriers suitable for granules include the following: for example, crushed and fractionated natural minerals such as calcite, marble, pumice, sepiolite, dolomite, and also synthetic granules of inorganic and organic meals, and also granules of organic material such as sawdust, paper, coconut shells, maize cobs, and tobacco stalks.

Liquefied gaseous extenders or solvents may also be used. Non-limiting examples are those extenders or carriers which at standard temperature and under standard pressure are gaseous, examples being aerosol propellants, such as halogenated hydrocarbons, and also butane, propane, nitrogen and carbon dioxide. Examples of emulsifiers and/or foam-formers, dispersants or wetting agents having ionic or nonionic properties, or mixtures of these surface-active substances, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyltaurates), phosphoric esters of polyethoxylated alcohols or phenols, fatty acid esters of polyols, and derivatives of the compounds containing sulphates, sulphonates and phosphates, examples being alkylaryl polyglycol ethers, alkylsulphonates, alkyl sulphates, arylsulphonates, protein hydrolysates, lignin-sulphite waste liquors and methylcellulose. The presence of a surface-active substance is advantageous if one of the active compounds and/or one of the inert carriers is not soluble in water and if application takes place in water.

Further auxiliaries that may be present in the formulations and in the application forms derived from them include colorants such as inorganic pigments, examples being iron oxide, titanium oxide, Prussian Blue, and organic dyes, such as alizarin dyes, azo dyes and metal phthalocyanine dyes, and nutrients and trace nutrients, such as salts of iron, manganese, boron, copper, cobalt, molybdenum, and zinc.

Stabilizers, such as low-temperature stabilizers, preservatives, antioxidants, light stabilizers or other agents which improve chemical and/or physical stability may also be present. Additionally present may be foam-formers or defoamers.

Furthermore, the formulations and application forms derived from them may also comprise, as additional auxiliaries, stickers such as carboxymethylcellulose, natural and synthetic polymers in powder, granule or latex form, such as gum arabic, polyvinyl alcohol, polyvinyl acetate, and also natural phospholipids, such as cephalins and lecithins, and synthetic phospholipids. Further possible auxiliaries include mineral and vegetable oils.

There may possibly be further auxiliaries present in the formulations and the application forms derived from them. Examples of such additives include fragrances, protective colloids, binders, adhesives, thickeners, thixotropic substances, penetrants, retention promoters, stabilizers, sequestrants, complexing agents, humectants and spreaders. Generally speaking, the active compounds may be combined with any solid or liquid additive commonly used for formulation purposes.

Suitable retention promoters include all those substances which reduce the dynamic surface tension, such as dioctyl sulphosuccinate, or increase the viscoelasticity, such as hydroxypropylguar polymers, for example.

Suitable penetrants in the present context include all those substances which are typically used in order to enhance the penetration of active agrochemical compounds into plants. Penetrants in this context are defined in that, from the (generally aqueous) application liquor and/or from the spray coating, they are able to penetrate the cuticle of the plant and thereby increase the mobility of the active compounds in the cuticle. This property can be determined using the method described in the literature (Baur et al., 1997, Pesticide Science 51: 131-152). Examples include alcohol alkoxylates such as coconut fatty ethoxylate (10) or isotridecyl ethoxylate (12), fatty acid esters such as rapeseed or soybean oil methyl esters, fatty amine alkoxylates such as tallowamine ethoxylate (15), or ammonium and/or phosphonium salts such as ammonium sulphate or diammonium hydrogen phosphate, for example.

The various compositions and formulations disclosed herein can comprise an amount of a cell of a bacterial strain, such as AIP045885, AIP075655, AIP09474, AIP024525, AIP033287, AIP093798, AIP061639, AIP082862, AIP058187, AIP059286, AIP036706, or active variant of any thereof, or a spore or a forespore or a combination of cells, forespores and/or spores, and/or can comprise an amount of a composition derived from any one of AIP045885, AIP075655, AIP09474, AIP024525, AIP033287, AIP093798, AIP061639, AIP082862, AIP058187, AIP059286, AIP036706, or an active variant of any thereof. Such an amount can comprise a concentration of the bacterial strain of at least about $10^4$ to about $10^{11}$, at least about $10^5$ CFU/gram to about $10^{11}$ CFU/gram, about $10^5$ CFU/gram to about $10^{10}$ CFU/gram, about $10^5$ CFU/gram to about $10^{12}$ CFU/gram, about $10^5$ CFU/gram to about $10^6$ CFU/gram, about $10^6$ CFU/gram to about $10^7$ CFU/gram, about $10^7$ CFU/gram to about $10^8$ CFU/gram, about $10^8$ CFU/gram to about $10^9$ CFU/gram, about $10^9$ CFU/gram to about $10^{10}$ CFU/gram, about $10^{10}$ CFU/gram to about $10^{11}$ CFU/gram, or about $10^{11}$ CFU/gram to about $10^{12}$ CFU/gram. In other embodiments, the concentration of the bacterial strain comprises at least about $10^4$ CFU/gram, at least about $10^5$ CFU/gram, at least about $10^6$ CFU/gram, at least about $10^7$ CFU/gram, at least about $10^8$ CFU/gram, at least about $10^9$ CFU/gram, at least about $10^{10}$ CFU/gram, at least about $10^{11}$ CFU/gram, at least about $10^{12}$ CFU/gram. Such concentrations of the bacterial strain can occur in any formulation type of interest, including, for example in a liquid formulation, wettable power, spray dried formulation, in a cell paste, wettable granule, or freeze dried formulation.

In some embodiments, the bacterial strain can occur in a liquid formulation. Liquid formulations can comprise an amount of a cell of a bacterial strain, such as AIP045885, AIP075655, AIP09474, AIP024525, AIP033287, AIP093798, AIP061639, AIP082862, AIP058187, AIP059286, AIP036706, or active variant of any thereof, or a spore or a forespore or a combination of cells, forespores and/or spores, from any one of AIP045885, AIP075655, AIP09474, AIP024525, AIP033287, AIP093798, AIP061639, AIP082862, AIP058187, AIP059286, AIP036706, or an active variant of any thereof, and/or a composition derived therefrom. In liquid formulations, the amount of bacterial strain, or active variant thereof, and/or a composition derived therefrom, disclosed herein can comprise a concentration of at least about $10^4$ to about $10^{11}$ CFU/mL, at least about $10^5$ CFU/mL to about $10^{11}$ CFU/mL, about $10^5$ CFU/mL to about $10^{10}$ CFU/mL, about $10^5$ CFU/mL to about $10^{12}$ CFU/mL, about $10^5$ CFU/mL to about $10^6$ CFU/mL, about $10^6$ CFU/mL to about $10^7$ CFU/mL, about $10^7$ CFU/mL to about $10^8$ CFU/mL, about $10^8$ CFU/mL to about $10^9$ CFU/mL, about $10^9$ CFU/mL to about $10^{10}$ CFU/mL, about $10^{10}$ CFU/mL to about $10^{11}$ CFU/mL, or about $10^{11}$ CFU/mL to about $10^{12}$ CFU/mL or at least about $10^4$ CFU/mL, at least about $10^5$ CFU/mL, at least about $10^6$ CFU/mL, at least about $10^7$ CFU/mL, at least about $10^8$ CFU/mL, at least about $10^9$ CFU/mL, at least about $10^{10}$ CFU/mL, at least about $10^{11}$ CFU/mL, at least about $10^{12}$ CFU/mL.

Dry formulations such as cell pastes, wettable powders, and spray dried formulations can comprise a cell of a bacterial strain, such as AIP045885, AIP075655, AIP09474, AIP024525, AIP033287, AIP093798, AIP061639, AIP082862, AIP058187, AIP059286, AIP036706, or active variant of any thereof, or a spore or a forespore or a combination of cells, forespores and/or spores of any thereof, and/or can comprise a composition derived from any one of AIP045885, AIP075655, AIP09474, AIP024525, AIP033287, AIP093798, AIP061639, AIP082862, AIP058187, AIP059286, AIP036706, or an active variant of any thereof. The amount of the bacterial strain in the dry formulation (e.g., cell pastes, wettable powders, and/or spray dried formulations) can comprise a concentration of the bacterial strain of at least about $10^5$ CFU/gram to about $10^{11}$ CFU/gram, about $10^7$ CFU/gram to about $10^{10}$ CFU/gram, about $10^7$ CFU/gram to about $10^{11}$ CFU/gram, about $10^6$ CFU/gram to about $10^{10}$ CFU/gram, about $10^6$ CFU/gram to about $10^{11}$ CFU/gram, about $10^{11}$ CFU/gram to about $10^{12}$ CFU/gram, about $10^5$ CFU/gram to about $10^{10}$ CFU/gram, about $10^5$ CFU/gram to about $10^{12}$ CFU/gram, about $10^5$ CFU/gram to about $10^6$ CFU/gram, about $10^6$ CFU/gram to about $10^7$ CFU/gram, about $10^7$ CFU/gram to about $10^8$ CFU/gram, about $10^8$ CFU/gram to about $10^9$ CFU/gram, about $10^9$ CFU/gram to about $10^{10}$ CFU/gram, about $10^{10}$ CFU/gram to about $10^{11}$ CFU/gram, or about $10^{11}$ CFU/gram to about $10^{12}$ CFU/gram. In some embodiments, the concentration of the bacterial strain comprises at least about $10^5$ CFU/gram, at least about $10^6$ CFU/gram, at least about $10^7$ CFU/gram, at least about $10^8$ CFU/gram, at least about $10^9$ CFU/gram, at least about $10^{10}$ CFU/gram, at least about $10^{11}$ CFU/gram, at least about $10^{12}$ CFU/gram, or at least about $10^{13}$ CFU/gram.

As used herein, a "cell paste" comprises a population of cells that has been centrifuged and/or filtered or otherwise concentrated. Further provided is a coated seed which comprises a seed and a coating on the seed, wherein the coating comprises a cell of at least one bacterial strain, such as AIP045885, AIP075655, AIP09474, AIP024525, AIP033287, AIP093798, AIP061639, AIP082862, AIP058187, AIP059286, AIP036706, or an active variant of any thereof, or a spore or a forespore or a combination of cells, forespores and/or spores of any thereof, and/or can comprise a composition derived from any one of AIP045885, AIP075655, AIP09474, AIP024525, AIP033287, AIP093798, AIP061639, AIP082862, AIP058187, AIP059286, AIP036706, or an active variant of any thereof, wherein said bacterial strain or the active variant thereof is present on the seed at about $10^5$ CFU/seed to about $10^7$ CFU/seed, at about $10^4$ CFU/seed to about $10^8$ CFU/seed, at about $10^4$ CFU/seed to about $10^5$ CFU/seed, at about $10^5$ CFU/seed to about $10^6$ CFU/seed, at about $10^6$ CFU/seed to about $10^7$ CFU/seed, or at about $10^7$ CFU/seed to about $10^8$ CFU/seed. Various plants of interest are disclosed elsewhere herein.

In particular embodiments, seeds are provided which comprise a heterologous coating on the seed, wherein the heterologous coating comprises a cell of at least one bacterial strain, such as AIP045885, AIP075655, AIP09474, AIP024525, AIP033287, AIP093798, AIP061639, AIP082862, AIP058187, AIP059286, AIP036706, or an active variant of any thereof, or a spore or a forespore or a combination of cells, forespores and/or spores, and/or can comprise a composition derived from any one of AIP045885, AIP075655, AIP09474, AIP024525, AIP033287, AIP093798, AIP061639, AIP082862, AIP058187, AIP059286, AIP036706, or an active variant of any thereof, wherein said bacterial strain or the active variant thereof is present on the seed at about $10^5$ CFU/seed to about $10^7$ CFU/seed, at about $10^4$ CFU/seed to about $10^8$ CFU/seed, at about $10^4$ CFU/seed to about $10^5$ CFU/seed, at about $10^5$ CFU/seed to about $10^6$ CFU/seed, at about $10^6$ CFU/seed to about $10^7$ CFU/seed, or at about $10^7$ CFU/seed to about $10^8$ CFU/seed. As used herein, "heterologous" in reference to a coating can refer to a seed coating comprising a bacterial strain that is not found in nature on the seed, or, if found in nature on the seed, is substantially modified from its native form in composition and/or concentration by deliberate human intervention. In particular embodiments, "heterologous" in reference to a coating can refer to a seed coating comprising a bacterial strain suspended in a solution in which the bacterial strain is not naturally found. The suspension solution for heterologous coatings can be natural or non-natural and can provide the bacterial strain with properties that the strain would not normally possess. For example, the suspension solution of a heterologous coating can permit the bacterial strain to adhere to the seed in such a manner that the bacteria retain activity during seed storage and germination.

A seed coating can further comprise at least one nutrient, at least one biocide (e.g., herbicide or pesticide). See, for example, US App Pub. 20040336049, 20140173979, and 20150033811.

Further provided is a composition comprising a whole cell broth, supernatant, filtrate, or extract derived from at least one of bacterial strain AIP045885, AIP075655, AIP09474, AIP024525, AIP033287, AIP093798, AIP061639, AIP082862, AIP058187, AIP059286, AIP036706, or an active variant of any thereof, wherein an effective amount of the composition improves an agronomic trait of interest of a plant or controls a plant pest or plant pathogen that causes disease. The composition contains effective compound(s), metabolite(s), and/or protein(s) which improve an agronomic trait of interest of a plant or controls a plant pest or plant pathogen that causes disease. The supernatant refers to the liquid remaining when cells are grown in broth or are harvested in another liquid from an agar plate and are removed by centrifugation, filtration, sedimentation, or other means well known in the art. The supernatant may be further concentrated to produce a filtrate. The filtrate may comprise a concentrated amount of an effective compound or metabolite compared to the concentration of the effective compound or metabolite in the supernatant or whole cell broth. In some embodiments, the supernatant, filtrate, or extract may be processed to a wettable powder and/or a spray dried formulation. In other embodiments, the supernatant, filtrate, or extract may be concentrated (e.g., water is removed) but remain in a liquid formulation. The composition described above can be applied alone or in combination with another substance, in an effective amount to control a plant pest or improve an agronomic trait of interest of a plant.

The various formulations disclosed herein can be stable for at least 30, 40, 50, 60, 70, 80, 90, 100, 125, 150, 200, 225, 250, 275, 300, 325, 350 days, 1.5 years, 2 years or longer. By stable is intended that the formulation retains viable bacteria and/or retains an effective amount of a biologically active bacterial population. Biological activity as used herein refers to the ability of the formulation to improve an agronomic trait of interest or control a plant pest. In one embodiment, the stable formulation retains at least about 1%, about 10%, about 20%, about 30% about 40%, about 50%, about 60%, about 70%, about 80%, or about 90% of CFU/gram in the formulation at a given storage time point when compared to the CFU/gram produced after immediate preparation of the formulation. In another embodiment, the stable formulation retains at least about 30% to 80%, about 50% to about 80%, about 60% to about 70%, about 70% to about 80%, about 40% to about 50%, about 50% to about 60%, about 60% to about 70% of biological activity in the formulation at a given storage time point when compared to the biological activity found in the formulation immediately after production. In another embodiment, the stable formulation at a given storage time point retains at least about 30%, 45%, 50%, 60%, 70%, 80%, 90% of biological activity when compared to the biological activity found in the formulation immediately after production. In still another embodiment, the stable formation retains any combination of the viability and biological activity noted above.

The formulations preferably comprise between 0.00000001% and 98% by weight of active compound or, with particular preference, between 0.01% and 95% by weight of active compound, more preferably between 0.5% and 90% by weight of active compound, based on the weight of the formulation.

The active compound content of the application forms prepared from the formulations may vary within wide ranges. The active compound concentration of the application forms may be situated typically between 0.00000001% and 95% by weight of active compound, preferably between 0.00001% and 1% by weight, based on the weight of the application form. Application takes place in a customary manner adapted to the application forms.

Moreover, the bacterial strain provided herein or an active variant thereof, and/or a composition derived therefrom can be mixed with a biocide, such as a fungicide, insecticide, or herbicide to enhance its activity or the activity of the chemical to which it has been added. In some cases, the combination of the bacterial strain (or the composition derived therefrom) and chemical may show synergistic activity where the mixture of the two exceeds that expected from their simple additive effect. In other embodiments, the biocontrol agents described herein can be mixed with other biocontrol agents.

In specific embodiments, the bacterial strain, active variant thereof, and/or a composition derived therefrom is compatible with agricultural chemicals used to improve performance of biocides. Such agricultural chemicals include safeners, surfactants, stickers, spreaders, UV protectants, and suspension and dispersal aids. Safeners are chemicals that improve or modify the performance of herbicides. Surfactants, spreaders, and stickers are chemicals included in agricultural spray preparations that change the mechanical properties of the spray (for example, by altering surface tension or improving leaf cuticle penetration). UV protectants improve the performance of agricultural biocides by reducing degradation by ultraviolet light. Suspension and dispersal aids improve the performance of biocides by altering their behavior in a spray tank. In instances where the bacterial strain or active variant is not compatible with an agricultural chemical of interest, if desired, methods can be undertaken to modify the bacterial strain to impart the compatibility of interest. Such methods to produce modified bacterial strains include both selection techniques and/or transformation techniques.

The bacterial strain provided herein, active variant thereof, and/or a composition derived therefrom can be used to significantly improve at least one agronomic trait of interest (e.g., reduce susceptibility to plant pests, such as insect and nematode pests). The bacterial strain provided herein, active variant thereof, and/or a composition derived therefrom can be used with other pesticides for an effective integrated pest management program. In one embodiment, the biocontrol populations can be mixed with known pesticides in a manner described in WO 94/10845, herein incorporated by reference.

Non-limiting examples of compounds and compositions that can be added to the formulation, include but are not limited to, Acetyl tributyl citrate [Citric acid, 2-(acetyloxy)-, tributyl ester]; Agar; Almond hulls; Almond shells; alpha-Cyclodextrin; Aluminatesilicate; Aluminum magnesium silicate [Silicic acid, aluminum magnesium salt]; Aluminum potassium sodium silicate [Silicic acid, aluminum potassium sodium salt]; Aluminum silicate; Aluminum sodium silicate [Silicic acid, aluminum sodium salt]; Aluminum sodium silicate (1:1:1)[Silicic acid ($H_4SiO_4$), aluminum sodium salt (1:1:1)]; Ammonium benzoate [Benzoic acid, ammonium salt]; Ammonium stearate [Octadecanoic acid, ammonium salt]; Amylopectin, acid-hydrolyzed, 1-octenylbutanedioate; Amylopectin, hydrogen 1-octadecenylbutanedioate; Animal glue; Ascorbyl palmitate; Attapulgite-type clay; Beeswax; Bentonite; Bentonite, sodian; *Beta*-Cyclodextrin; Bone meal; Bran; Bread crumbs; (+)-Butyl lactate; [Lactic acid, n-butyl ester, (S)]; Butyl lactate [Lactic acid, n-butyl ester]; Butyl stearate [Octadecanoic acid, butyl ester]; Calcareous shale; Calcite ($Ca(Co_3)$); Calcium acetate; Calcium acetate monohydrate [Acetic acid, calcium salt, monohydrate]; Calcium benzoate [Benzoic acid, calcium salt]; Calcium carbonate; Calcium citrate [Citric acid, calcium salt]; Calcium octanoate; Calcium oxide silicate ($Ca_3O(SiO_4)$); Calcium silicate [Silicic acid, calcium salt]; Calcium stearate [Octadecanoic acid, calcium salt]; Calcium sulfate; Calcium sulfate dehydrate; Calcium sulfate hemihydrate; Canary seed; Carbon; Carbon dioxide; Carboxymethyl cellulose [Cellulose, carboxymethyl ether]; Cardboard; Carnauba wax; Carob gum [Locust bean gum]; Carrageenan; Caseins; Castor oil; Castor oil, hydrogenated; Cat food; Cellulose; Cellulose acetate; Cellulose, mixture with cellulose carboxymethyl ether, sodium salt; Cellulose, pulp; Cellulose, regenerated; Cheese; Chlorophyll a; Chlorophyll b; *Citrus* meal; Citric acid; Citric acid, monohydrate; *Citrus* pectin; *Citrus* pulp; Clam shells; Cocoa; Cocoa shell flour; Cocoa shells; Cod-liver oil; Coffee grounds; Cookies; Cork; Corn cobs; Cotton; Cottonseed meal; Cracked wheat; Decanoic acid, monoester with 1,2,3-propanetriol; Dextrins; Diglyceryl monooleate [9-Octadecenoic acid, ester with 1,2,3-propanetriol]; Diglyceryl monostearate [9-Octadecanoic acid, monoester with xybis(propanediol)]; Dilaurin [Dodecanoic acid, diester with 1,2,3-propanetriol]; Dipalmitin [Hexadecanoic acid, diester with 1,2,3-propanetriol]; Dipotassium citrate [Citric acid, dipotassium salt]; Disodium citrate [Citric acid, disodium salt]; Disodium sulfate decahydrate; Diatomaceous earth (less than 1% crystalline silica); Dodecanoic acid, monoester with 1,2,3-propanetriol; Dolomite; Douglas fir bark; Egg shells; Eggs; (+)-Ethyl lactate [Lactic acid, ethyl ester, (S)]; Ethyl lactate [Lactic acid, ethyl ester]; Feldspar; Fish meal; Fish oil (not conforming to 40 CFR 180.950); Fuller's earth; Fumaric acid; gamma-Cyclodextrin; Gelatins; Gellan gum; Glue (as depolymd. animal collagen); Glycerin [1,2,3-Propanetriol]; Glycerol monooleate [9-Octadecenoic acid (Z)-, 2,3-dihydroxypropyl ester]; Glyceryl dicaprylate [Octanoic acid, diester with 1,2,3-propanetriol]; Glyceryl dimyristate [Tetradecanoic acid, diester with 1,2,3-propanetriol]; Glyceryl dioleate [9-Octadecenoic acid (9Z)-, diester with 1,2,3-propanetriol]; Glyceryl distearate; Glyceryl monomyristate [Tetradecanoic acid, monoester with 1,2,3-propanetriol]; Glyceryl monooctanoate [Octanoic acid, monoester with 1,2,3-propanetriol]; Glyceryl monooleate [9-Octadecenoic acid (9Z)-, monoester with 1,2,3-propanetriol]; Glyceryl monostearate [Octadecanoic acid, monoester with 1,2,3-propanetriol]; Glyceryl stearate [Octadecanoic acid, ester with 1,2,3-propanetriol]; Granite; Graphite; Guar gum; Gum Arabic; Gum tragacanth; Gypsum; Hematite ($Fe_2O_3$); Humic acid; Hydrogenated cottonseed oil; Hydrogenated rapeseed oil; Hydrogenated soybean oil; Hydroxyethyl cellulose [Cellulose, 2-hydroxyethyl ether]; Hydroxypropyl cellulose [Cellulose, 2-hydroxypropyl ether]; Hydroxypropyl methyl cellulose [Cellulose, 2-hydroxypropyl methyl ether]; Iron magnesium oxide ($Fe_2MgO_4$); Iron oxide ($Fe_2O_3$); Iron oxide ($Fe_2O_3$); Iron oxide ($Fe_3O4$); Iron oxide (FeO); Isopropyl alcohol [2-Propanol]; Isopropyl myristate; Kaolin; Lactose; Lactose monohydrate; Lanolin; Latex rubber; Lauric acid; Lecithins; Licorice extract; Lime (chemical) dolomitic; Limestone; Linseed oil; Magnesium carbonate [Carbonic acid, magnesium salt (1:1); Magnesium benzoate; Magnesium oxide; Magnesium oxide silicate ($Mg_3O(Si_2O_5)_2$), monohydrate; Magnesium silicate; Magnesium silicate hydrate; Magnesium silicon oxide ($Mg_2Si_3O_8$); Magnesium stearate [Octadecanoic acid, magnesium salt]; Magnesium sulfate; Magnesium sulfate heptahydrate; Malic acid; Malt extract; Malt flavor; Maltodextrin; Methylcellulose [Cellulose, methyl ether]; Mica; Mica-group minerals; Milk; N/A Millet seed; Mineral oil (U.S.P.); 1-Monolaurin [Dodecanoic acid, 2,3-dihydroxypropyl ester]; 1-Monomyristin [Tetradecanoic acid, 2,3-dihydroxypropyl ester]; Monomyristin [Decanoic acid, diester with 1,2,3-propanetriol]; Monopalmitin [Hexadecanoic acid, monoester with 1,2,3-propanetriol]; Monopotassium citrate [Citric acid, monopotassium salt; Monosodium citrate [Citric acid, monosodium salt]; Montmorillonite; Myristic acid; Nepheline syenite; Nitrogen; Nutria meat; Nylon; Octanoic acid, potassium salt; Octanoic acid, sodium salt; Oils, almond; Oils, wheat; Oleic acid; Oyster shells; Palm oil; Palm oil, hydrogenated; Palmitic acid [Hexadecanoic acid]; Paraffin wax; Peanut butter; Peanut shells; Peanuts; Peat moss; Pectin; Perlite; Perlite, expanded; Plaster of paris; Polyethylene; Polyglyceryl oleate; Polyglyceryl stearate; Potassium acetate [Acetic acid, potassium salt]; Potassium aluminum silicate, anhydrous; Potassium benzoate [Benzoic acid, potassium salt]; Potassium bicarbonate [Carbonic acid, monopotassium salt]; Potassium chloride; Potassium citrate [Citric acid, potassium salt]; Potassium humate [Humic acids, potassium salts]; Potassium myristate [Tetradecanoic acid, potassium salt]; Potassium oleate [9-Octadecenoic acid (9Z)-, potassium salt; Potassium ricinoleate [9-Octadecenoic acid, 12-hydroxy-, monopotassium salt, (9Z,12R)-]; Potassium sorbate [Sorbic acid, potassium salt]; Potassium stearate [Octadecanoic acid, potassium salt]; Potassium sulfate; Potassium sulfate [Sulfuric acid, monopotassium salt]; 1,2-Propylene carbonate [1,3-Dioxolan-2-one, 4-methyl-]; Pumice; Red cabbage color (expressed from edible red cabbage heads via a pressing process using only acidified water); Red cedar chips; Red dog flour; Rubber; Sawdust; Shale; Silica, amorphous, fumed (crystalline free); Silica, amorphous, precipated and gel; Silica (crystalline free); Silica gel; Silica gel, precipitated, crystalline-free; Silica, hydrate; Silica, vitreous; Silicic acid ($H_2SiO_3$), magnesium salt (1:1); Soap (The water soluble sodium or potassium salts of fatty acids produced by either the saponification of fats and oils, or the neutralization of fatty acid); Soapbark [Quillaja saponin]; Soapstone; Sodium acetate [Acetic acid, sodium salt]; Sodium alginate; Sodium benzoate [Benzoic acid, sodium salt]; Sodium bicarbonate; Sodium carboxymethyl cellulose [Cellulose, carboxymethyl ether, sodium salt]; Sodium chloride; Sodium citrate; Sodium humate [Humic acids, sodium salts]; Sodium oleate; Sodium ricinoleate [9-Octadecenoic acid, 12-hydroxy-, monosodium salt, (9Z,12R)-]; Sodium stearate [Octadecanoic acid, sodium salt]; Sodium sulfate; Sorbitol [D-glucitol]; Soy protein; Soya lecithins [Lecithins, soya]; Soybean hulls; Soybean meal; Soybean, flour; Stearic acid [Octadecanoic acid]; Sulfur; Syrups, hydrolyzed starch, hydrogenated; Tetragylceryl monooleate [9-Octadecenoic acid (9Z)-, monoester with tetraglycerol]; Tricalcium citrate [Citric acid, calcium salt (2:3)]; Triethyl citrate [Citric acid, triethyl ester; Tripotassium citrate [Citric acid, tripotassium salt]; Tripotassium citrate monohydrate [Citric acid, tripotassium salt, monohydrate]; Trisodium citrate [Citric acid, trisodium salt]; Trisodium citrate dehydrate [Citric acid, trisodium salt, dehydrate]; Trisodium citrate pentahydrate [Citric acid, trisodium salt, pentahydrate]; Ultramarine blue [C.I. Pigment Blue 29]; Urea; Vanilla; Vermiculite; Vinegar (maximum 8% acetic acid in solution); Vitamin C [L-Ascorbic acid]; Vitamin; Walnut flour; Walnut shells; Wheat; Wheat flour; Wheat germ oil; Whey; White mineral oil (petroleum); Wintergreen oil; Wollastonite (Ca(SiO3)); Wool; Xanthan gum; Yeast; Zeolites (excluding erionite (CAS Reg. No. 66733-21-9)); Zeolites, NaA; Zinc iron oxide; Zinc oxide (ZnO); and Zinc stearate [Octadecanoic acid, zinc salt].

IV. Methods of Use

The bacterial strains or modified bacterial strains, active variants thereof, and/or compositions derived therefrom provided herein can be employed with any plant species to control a plant pest or improve an agronomic trait of interest. Agronomic traits of interest include any trait that improves plant health or commercial value. Non-limiting examples of agronomic traits of interest including increase in biomass, increase in drought tolerance, thermal tolerance, herbicide tolerance, drought resistance, pest resistance (e.g., nematode resistance, insect resistance, fungus resistance, virus resistance, bacteria resistance), male sterility, cold tolerance, salt tolerance, increased yield, enhanced nutrient use efficiency, increased nitrogen use efficiency, increased tolerance to nitrogen stress, increased fermentable carbohydrate content, reduced lignin content, increased antioxidant content, enhanced water use efficiency, increased vigor, increased germination efficiency, earlier or increased flowering, increased biomass, altered root-to-shoot biomass ratio, enhanced soil water retention, or a combination thereof. In other instances, the agronomic trait of interest includes an altered oil content, altered protein content, altered seed carbohydrate composition, altered seed oil composition, and altered seed protein composition, chemical tolerance, cold tolerance, delayed senescence, disease resistance, drought tolerance, ear weight, growth improvement, health enhancement, heat tolerance, herbicide tolerance, herbivore resistance, improved nitrogen fixation, improved nitrogen utilization, improved root architecture, improved water use efficiency, increased biomass, increased root length, increased seed weight, increased shoot length, increased yield, increased yield under water-limited conditions, kernel mass, kernel moisture content, metal tolerance, number of ears, number of kernels per ear, number of pods, nutrition enhancement, photosynthetic capability improvement, salinity tolerance, stay-green, vigor improvement, increased dry weight of mature seeds, increased fresh weight of mature seeds, increased number of mature seeds per plant, increased chlorophyll content, increased number of pods per plant, increased length of pods per plant, reduced number of wilted leaves per plant, reduced number of severely wilted leaves per plant, and increased number of non-wilted leaves per plant, a detectable modulation in the level of a metabolite, a detectable modulation in the level of a transcript, or a detectable modulation in the proteome relative to a reference plant.

In one non-limiting embodiment, the bacterial strain, active variant thereof, and/or a composition derived therefrom provided herein can be employed with any plant species susceptible to a plant pest or at risk of developing a plant disease or damage caused by a plant pest. By "pest resistance" is intended that the bacterial strain, active variant thereof, and/or a composition derived therefrom provided herein can inhibit (inhibit growth, feeding, fecundity, or viability), suppress (suppressing growth, feeding, fecundity, or viability), reduce (reduce the pest infestation, reduce the pest feeding activities on a particular plant) or kill (cause the morbidity, mortality, or reduced fecundity of) a pest, such as an insect pest. By "a plant susceptible to a pest" is meant that a pest is able to infect or damage the plant. For example, a plant susceptible to a pest can be susceptible to damage caused by a fungal, insect, or nematode pest as disclosed elsewhere herein.

Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), Sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), *Citrus* trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), grape (Vitus spp.), strawberry (*Fragaria* x *ananassa*), cherry (*Prunus* spp.), apple (*Malus domestica*), orange (*Citrus* x *sinensis*) cashew (*Anacardium occidentale*), Macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), Hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and *chrysanthemum*.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, *Sorghum*, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, *Sorghum*, rye, etc. Oil-seed plants include cotton, soybean, safflower, sunflower, *Brassica*, maize, alfalfa, palm, coconut, etc. Leguminous plants include beans, peas, and dry pulses. Beans include guar, locust bean, fenugreek, soybean, garden beans, cowpea, mungbean, lima bean, fava bean, lentils, chickpea, etc.

A. Non-Limiting Plant Pests

In specific embodiments, the bacterial strains provided herein are those that target one or more plant pests. The term "pests" includes but is not limited to, insects, fungi, bacteria, nematodes, viruses or viroids, protozoan pathogens, and the like.

In specific embodiments, the bacterial strains provided herein are those that target one or more insect or insect pests. The term "insects" or "insect pests" as used herein refers to insects and other similar pests. The term "insect" encompasses eggs, larvae, juvenile and mature forms of insects. Insects can be targeted at any stage of development. For example, insects can be targeted after the first instar, during the second instar, third instar, fourth instar, fifth instar, or any other developmental or adult growth stage. As used herein, the term "instar" is used to denote the developmental stage of the larval or nymphal forms of insects. Insect pests include insects selected from the orders Coleoptera, Lepidoptera, Hemiptera, Diptera, Hymenoptera, Lepidoptera, Mallophaga, Homoptera, Hemiptera, Orthroptera, Thysanoptera, Trombidiformes, Dermaptera, Isoptera, Anoplura, Siphonaptera, Trichoptera, etc.

Insect pests of the order Coleoptera include, but are not limited to, *Agriotes* spp., *Anthonomus* spp., *Atomaria linearis*, *Chaetocnema tibialis*, *Cosmopolites* spp., *Curculio* spp., *Dermestes* spp., *Epilachna* spp., *Eremnus* spp., *Leptinotarsa decemlineata*, *Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., Scarabeidae, *Sitophilus* spp., *Sitotroga* spp., *Tenebrio* spp., *Tribolium* spp., and *Trogoderma* spp. In specific embodiments, Coleoptera insects include, but are not limited to weevils from the families Anthribidae, Bruchidae, and Curculionidae (e.g., sweetpotato weevil (*Cylas formicarius* (Fabricius)), boll weevil (*Anthonomus grandis* Boheman), rice water weevil (*Lissorhoptrus oryzophilus* Kuschel), rice weevil (*Sitophilus oryzae* L.)); flea beetles, cucumber beetles, rootworms, leaf beetles, potato beetles, and leafminers in the family Chrysomelidae (e.g., Colorado potato beetle (*Leptinotarsa decemlineata* Say), *Diabrotica* spp. including western corn rootworm (*Diabrotica virgifera virgifera* LeConte)); chafers and other beetles from the family Scaribaeidae (e.g., Japanese beetle (*Popillia japonica* Newman) and European chafer (*Rhizotrogus majalis* Razoumowsky)); wireworms from the family Elateridae and bark beetles from the family Scolytidae.

As disclosed herein, insect pests include Coleoptera pests of the corn rootworm complex: Western corn rootworm, *Diabrotica virgifera virgifera*; northern corn rootworm, *D. barberi*; Southern corn rootworm or spotted cucumber beetle, *Diabrotica undecimpunctata howardi*; and the Mexican corn rootworm, *D. virgifera zeae*. In specific embodiments, the insect pest is Western corn rootworm, *Diabrotica virgifera virgifera*.

Insect pests that can be controlled with the compositions and methods disclosed herein further include insects of the order Lepidoptera, e.g. *Achoroia grisella, Acleris gloverana, Acleris variana, Adoxophyes orana, Agrotis ipsilon, Alabama argillacea, Alsophila pometaria, Amyelois transitella, Anagasta kuehniella, Anarsia lineatella, Anisota senatoria, Antheraea pernyi, Anticarsia gemmatalis, Archips* spp., *Argyrotaenia* spp., *Athetis mindara, Bombyx mori, Bucculatrix thurberiella, Cadra cautella, Choristoneura* sp., *Cochylls hospes, Colias eurytheme, Corcyra cephalonica, Cydia latiferreanus, Cydia pomonella, Datana integerrima, Dendrolimus sibericus, Desmiafeneralis* spp., *Diaphania hyalinata, Diaphania nitidalis, Diatraea grandiosella, Diatraea saccharalis, Ennomos subsignaria, Eoreuma loftini, Esphestia elutella, Erannis tilaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea, Heliothis virescens, Hemileuca oliviae, Homoeosoma electellum, Hyphantia cunea, Keiferia lycopersicella, Lambdina fiscellaria fiscellaria, Lambdina fiscellaria lugubrosa, Leucoma salicis, Lobesia botrana, Loxostege sticticalis, Lymantria dispar, Macalla thyrisalis, Malacosoma* spp., *Mamestra brassicae, Mamestra configurata, Manduca quinquemaculata, Manduca sexta, Maruca testulalis, Melanchra picta, Operophtera brumata, Orgyia* spp., *Ostrinia nubilalis, Paleacrita vernata, Papilio cresphontes, Pectinophora gossypiella, Phryganidia californica, Phyllonorycter blancardella, Pieris napi, Pieris rapae, Plathypena scabra, Platynota flouendana, Platynota stultana, Platyptilia carduidactyla, Plodia interpunctella, Plutella xylostella, Pontia protodice, Pseudaletia unipuncta, Pseudoplasia includens, Sabulodes aegrotata, Schizura concinna, Sitotroga cerealella, Spilonta ocellana, Spodoptera* spp., *Thaurnstopoea pityocampa, Tinsola bisselliella, Trichoplusia hi, Tuta absoluta, Udea rubigalis, Xylomyges curiails*, and *Yponomeuta padella*.

The methods and compositions provided herein can also be used against insect pests of the order Hemiptera including, but not limited to, *Lygus* spp., including *Lygus* spp. including *Lygus hesperus, Lygus lineolaris, Lygus pratensis, Lygus rugulipennis*, and *Lygus pabulinus, Calocoris norvegicus, Orthops compestris, Plesiocoris rugicollis, Cyrtopeltis modestus, Cyrtopeltis notatus, Spanagonicus albofasciatus, Diaphnocoris chlorinonis, Labopidicola allii, Pseudatomoscelis seriatus, Adelphocoris rapidus, Poecilocapsus lineatus, Blissus leucopterus, Nysius* spp. including *Nysius ericae* and *Nysius raphanus, Nezara viridula, Acrosternum hilare, Euschistus* spp. including *Euschistus serous* and *Euschistus heros, Dichelops* spp. including *Dichelops melacantus* and *Dichelops furcatus, Halyomorpha halys, Lipaphis erysimi, Aphis gossypii, Macrosiphum avenae, Myzus persicae, Acyrthosiphon pisum*, Aphidoidea spp, *Eurygaster* spp., Coreidae spp., Pyrrhocoridae spp., Blostomatidae spp., Reduviidae spp., Cimicidae spp. *Aleurocanthus woglumi, Aleyrodes proletella, Bemisia* spp. including *Bemisia argentifolii* and *Bemisia tabaci*, and *Trialeurodes vaporariorum*

The methods and compositions provided herein can also be used against insect pests of the order Thysenoptera including, but not limited to, *Thrips* species, including *Frankliniella* spp., for example Western Flower *Thrips* (*Frankliniella occidentalis* (Pergande)); *Thrips* spp., for example *Thrips tabaci; Scirtothrips* spp., for example *Scirtothrips dorsalis; Klambothrips* spp., for example *Klambothrips myopori; Echinothrips* spp., for example *Echinothrips americanus*; and *Megalurothrips* spp., for example *Megalurothrips usitatus*.

The methods and compositions provided herein can also be used against insect pests of the order Trombidiformes including, but are not limited to, plant feeding mites, including six-spotted spider mite (*Eutetranychus sexmaculatus*), Texas Citrus mite (*Eutetranychus banksi*), Citrus red mite (*Panonychus citri*), European red mite (*Panonychus ulmi*), McDaniel mite (*Tetranychus mcdanieli*), Pacific spider mite (*Tetranychus pacificus*), Strawberry spider mite (*Tetrany-*

*chus urticae*), Spruce spider mite (*Oligonychus ununguis*), Sugi spider mite (*Oligonychus nondonensisi*), and *Tetranychus evansi*.

Insect pests of interest also include *Araecerus fasciculatus*, coffee bean weevil; *Acanthoscelides obtectus*, bean weevil; *Bruchus rufimanus*, broadbean weevil; *Bruchus pisorum*, pea weevil; *Zabrotes subfasciatus*, Mexican bean weevil; *Diabrotica balteata*, banded cucumber beetle; *Cerotoma trifurcata*, bean leaf beetle; *Diabrotica virgifera*, Mexican corn rootworm; *Epitrix cucumeris*, potato flea beetle; *Chaetocnema confinis*, sweet potato flea beetle; *Hypera postica*, alfalfa weevil; *Anthonomus quadrigibbus*, apple *Curculio*; *Sternechus paludatus*, bean stalk weevil; *Hypera brunnipennis*, Egyptian alfalfa weevil; *Sitophilus granaries*, granary weevil; *Craponius inaequalis*, grape *Curculio*; *Sitophilus zeamais*, maize weevil; *Conotrachelus nenuphar*, plum *Curculio*; *Euscepes postfaciatus*, West Indian sweet potato weevil; *Maladera castanea*, Asiatic garden beetle; *Rhizotrogus majalis*, European chafer; *Macrodactylus subspinosus*, rose chafer; *Tribolium confusum*, confused flour beetle; *Tenebrio obscurus*, dark mealworm; *Tribolium castaneum*, red flour beetle; *Tenebrio molitor*, yellow mealworm and the family Drosophilidae including *Drosophila suzukii*, spotted wing *drosophila*.

Insect pests also include insects selected from the orders Diptera, Hymenoptera, Mallophaga, Homoptera, Hemiptera, Orthroptera, Thysanoptera, Dermaptera, Isoptera, Anoplura, Siphonaptera, and Trichoptera. Insect pests of the present invention can further include those of the order Acari including, but not limited to, mites and ticks. In specific embodiments, coleopteran pests include Western corn rootworm, Colorado potato beetle, and/or sweet potato weevil.

Insect pests that can be controlled with the compositions and methods of the invention for the major crops include, but are not limited to: Maize: *Ostrinia nubilalis*, European corn borer; *Agrotis ipsilon*, black cutworm; *Helicoverpa zeae*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, sugarcane borer; western corn rootworm, e.g., *Diabrotica virgifera virgifera*; northern corn rootworm, e.g., *Diabrotica longicornis barberi*; southern corn rootworm, e.g., *Diabrotica undecimpunctata howardi; Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Myzus persicae*, green peach aphid; *Nezara viridula*, southern green stink bug; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blotch leafminer; *Anaphothrips obscrurus*, grass *Thrips*; *Solenopsis milesta*, thief ant; *Tetranychus urticae*, two spotted spider mite; Sorghum: *Chilo partellus*, *Sorghum* borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes*, *Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*, corn leaf aphid; *Sipha flava*, yellow sugarcane aphid; chinch bug, e.g., *Blissus leucopterus leucopterus*; *Contarinia sorghicola*, *Sorghum* midge; *Tetranychus cinnabarinus*, carmine spider mite; *Tetranychus urticae*, two-spotted spider mite; Wheat: *Pseudaletia unipunctata*, armyworm; *Spodoptera frugiperda*, fall armyworm; *Elasmopalpus lignosellus*, lesser cornstalk borer; *Agrotis orthogonia*, pale western cutworm; *Elasmopalpus lignosellus*, lesser cornstalk borer; *Oulema melanopus*, cereal leaf beetle; *Hypera punctata*, clover leaf weevil; southern corn rootworm, e.g., *Diabrotica undecimpunctata howardi*; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco *Thrips*; *Cephus cinctus*, wheat stem sawfly; *Aceria tulipae*, wheat curl mite; Sunflower: *Cylindrocupturus adspersus*, sunflower stem weevil; *Smicronyx fulus*, red sunflower seed weevil; *Smicronyx sordidus*, gray sunflower seed weevil; *Suleima helianthana*, sunflower bud moth; *Homoeosoma electellum*, sunflower moth; *Zygogramma exclamationis*, sunflower beetle; *Bothyrus gibbosus*, carrot beetle; *Neolasioptera murtfeldtiana*, sunflower seed midge; Cotton: *Heliothis virescens*, tobacco budworm; *Helicoverpa zea*, cotton bollworm; *Spodoptera exigua*, beet armyworm; *Pectinophora gossypiella*, pink bollworm; boll weevil, e.g., *Anthonomus grandis*; *Aphis gossypii*, cotton aphid; *Pseudatomoscelis seriatus*, cotton fleahopper; *Trialeurodes abutilonea*, banded winged whitefly; *Lygus lineolaris*, tarnished plant bug; *Melanoplus femurrubrum*, redlegged grasshopper; *Melanoplus differentialis*, differential grasshopper; *Thrips tabaci*, onion *Thrips*; *Frankliniella fusca*, tobacco *Thrips*; *Tetranychus cinnabarinus*, carmine spider mite; *Tetranychus urticae*, two-spotted spider mite; Rice: *Diatraea saccharalis*, sugarcane borer; *Spodoptera frugiperda*, fall armyworm; *Helicoverpa zea*, corn earworm; *Colaspis brunnea*, grape *colaspis*; *Lissorhoptrus oryzophilus*, rice water weevil; *Sitophilus oryzae*, rice weevil; *Nephotettix nigropictus*, rice leafhopper; chinch bug, e.g., *Blissus leucopterus leucopterus*; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, tobacco budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean *Thrips*; *Thrips tabaci*, onion *Thrips*; *Tetranychus turkestani*, strawberry spider mite; *Tetranychus urticae*, two-spotted spider mite; Barley: *Ostrinia nubilalis*, European corn borer; *Agrotis ipsilon*, black cutworm; *Schizaphis graminum*, greenbug; chinch bug, e.g., *Blissus leucopterus leucopterus*; *Acrosternum hilare*, green stink bug; *Euschistus serous*, brown stink bug; *Jylemya platura*, seedcorn maggot; *Mayetiola destructor*, Hessian fly; *Petrobia latens*, brown wheat mite; Oil Seed Rape: *Vrevicoryne brassicae*, cabbage aphid; *Phyllotreta cruciferae*, crucifer flea beetle; *Phyllotreta striolata*, striped flea beetle; *Phyllotreta nemorum*, striped turnip flea beetle; *Meligethes aeneus*, rapeseed beetle; and the pollen beetles *Meligethes rufimanus*, *Meligethes nigrescens*, *Meligethes canadianus*, and *Meligethes viridescens*; Potato: *Leptinotarsa decemlineata*, Colorado potato beetle; Sweet potato:

*Spartocera batatas*, giant sweet potato bug; *Charidotella* (=*Metriona*) *bicolor*, golden tortoise beetle; *Cylas formicarius*, sweet potato weevil; *Cylas puncticollis*, sweet potato weevil; *Cylas brunneus*, sweet potato weevil Naupactus (=*Graphognathus*) spp., whitefringed beetles; *Conoderus rudis*, wireworm; *Conoderus scissus*, peanut wireworm; *Blosyrus* spp., rough sweet potato weevil; *Acraea acerata*, sweet potato butterfly; *Agrius convolvuli*, sweet potato hornworm; *Spodoptera exigua*, armyworm; *Spodoptera eridania*, armyworm; *Synanthedon* spp., clearwing moth; Hairiness and eriophyid mites; *Euscepes postfasciatus*, West Indian sweetpotato weevil; *Peloropus batatae, Peloropus* weevil; *Omphisia anastomasalis*, sweet potato stemborer, and white grubs-larvae of various species of scarabid beetles.

In some embodiments, the compositions and methods provided herein control nematode plant pests. Nematodes include parasitic nematodes such as root-knot, cyst, and lesion nematodes, including of the species *Meloidogyne* such as the Southern Root-Knot nematode (*Meloidogyne incognita*), Javanese Root-Knot nematode (*Meloidogyne javanica*), Northern Root-Knot Nematode (*Meloidogyne hapla*) and Peanut Root-Knot Nematode (*Meloidogyne arenaria*); nematodes of the species *Ditylenchus* such as *Ditylenchus destructor* and *Ditylenchus dipsaci*; nematodes of the species *Pratylenchus* such as the Cob Root-Lesion Nematode (*Pratylenchus penetrans*), Chrysanthemum Root-Lesion Nematode (*Pratylenchus fallax*), *Pratylenchus coffeae, Pratylenchus loosi* and Walnut Root-Lesion Nematode (*Pratylenchus vulnus*); Nematodes of the species *Globodera* such as *Globodera rostochiensis* and *Globodera pallida*; Nematodes of the species *Heterodera* such as *Heterodera glycines* (soybean cyst nematode); *Heterodera schachtii* (beet cyst nematode); *Heterodera avenae* (cereal cyst nematode); Nematodes of the species *Aphelenchoides* such as the Rice White-tip Nematode (*Aphelenchoides besseyi*), *Aphelenchoides ritzemabosi* and *Aphelenchoides fragariae*; Nematodes of the species *Aphelenchus* such as *Aphelenchus avenae*; Nematodes of the species *Radopholus*, such as the Burrowing-Nematode (*Radopholus similis*); Nematodes of the species *Tylenchulus* such as *Tylenchulus semipenetrans*; Nematodes of the species *Rotylenchulus* such as *Rotylenchulus reniformis*; Nematodes living in trees such as *Bursaphelenchus xylophilus* and the Red Ring Nematode (*Bursaphelenchus cocophilus*) etc. and *Globodera* spp.; particularly members of the cyst nematodes, including, but not limited to *Globodera rostochiensis* and *Globodera pailida* (potato cyst nematodes); Spiral (*Helicotylenchus* spp.); Burrowing (*Radopholus similis*); Bulb and stem (*Ditylenchus dipsaci*); Reniform (*Rotylenchulus reniformis*); Dagger (*Xiphinema* spp.); Bud and leaf (*Aphelenchoides* spp.); and Pine Wilt Disease (*Bursaphelenchus xylophilus*). Lesion nematodes include *Pratylenchus* spp. The term "nematode" encompasses eggs, larvae, juvenile and mature forms of nematodes.

Bacterial strains or active variants thereof and/or a composition derived therefrom can be tested for pesticidal activity against a pest in any developmental stage, including early developmental stages, e.g., as larvae or other immature forms. For example, larvae of insect pests may be reared in total darkness at from about 20° C. to about 30° C. and from about 30% to about 70% relative humidity. Bioassays may be performed as described in Czapla and Lang (1990) *J. Econ. Entomol.* 83 (6): 2480-2485. Methods of rearing insect larvae and performing bioassays are well known to one of ordinary skill in the art.

In specific embodiments, the bacterial strains provided herein are those that target one or more insect or insect pests. For example, the various bacterial strains provided herein target one or more insect pests that cause damage to plants. For example, any of the bacterial strain provided herein or active variant thereof can have insecticidal activity against one, two, three, four, five, or more insect pests described herein.

In specific embodiments, a cell of the bacterial strain AIP045885, AIP075655, AIP09474, AIP024525, AIP033287, AIP093798, AIP061639, AIP082862, AIP058187, AIP059286, AIP036706, or an active variant of any thereof, or a spore, or a forespore or a combination of cells, forespores and/or spores control an insect or nematode pest. Thus, in some embodiments, the plant pest disclosed herein is an insect pest from the order Coleoptera. For example, a cell of the bacterial strain AIP045885, AIP075655, AIP09474, AIP024525, AIP033287, AIP093798, AIP061639, AIP082862, AIP058187, AIP059286, AIP036706, or an active variant of any thereof, or a spore, or a forespore or a combination of cells, forespores and/or spores can control corn rootworm, Colorado potato beetle, and weevils. In specific embodiments, a cell of the bacterial strain AIP045885, AIP075655, AIP09474, AIP024525, AIP033287, AIP093798, AIP061639, AIP082862, AIP058187, AIP059286, AIP036706, or an active variant of any thereof, can have activity against Western corn rootworm, Colorado potato beetle, and/or sweet potato weevil. In particular embodiments, AIP045885, AIP075655, AIP09474, AIP024525, AIP033287, AIP093798, AIP061639, AIP082862, AIP058187, AIP059286, AIP036706, or an active variant of any thereof, has activity against root-knot nematodes and Southern green stink bug.

The methods and compositions disclosed herein can be used to control one or more bacterial pathogens. A bacterial pathogen can be, but is not limited to, a bacterial species selected from the group consisting of *Erwinia* spp., such as *Erwinia amylovora*, *Pseudomonas* spp. such as *Pseudomonas syringae* pv. *phaseolicola*, *Ralstonia* spp. such as *Ralstonia solanacearum*, *Xanthomonas* spp. such as *Xanthomonas vesicatoria*, and *Streptomyces* spp. such as *Streptomyces scabies*. The methods and compositions disclosed herein can also be used to control *Salmonella* spp. such as *Salmonella enterica* and/or *Escherichia* spp. such as *Escherichia coli*.

The methods and compositions disclosed herein can be used to control one or more fungal pests. A fungal pest can be, but is not limited to, a fungus selected from the group consisting of *Aspergillus* spp., *Botrytis* spp., *Botrytis cinerea*, *Cersospora* spp., *Cercospora sojina*, *Cercospora beticola*, *Alternaria* spp., *Alternaria solani*, *Rhizoctonia* spp., *Rhizoctonia solani*, *Blumeria graminis* f sp. *Tritici*, *Erysiphe necator*, *Podosphaera xanthii*, *Golovinomyces cichoracearum*, *Erysiphe lagerstroemiae*, *Sphaerotheca pannosa*, *Colletotrichum cereale*, *Apiognomonia errabunda*, *Apiognomonia veneta*, *Colletotrichum* spp, *Colletotrichum gloeosporiodes*, *Discula fraxinea*, *Mycosphaerella* spp., *Phomopsis* spp., *Plasmopara viticola*, *Pseudoperonospora cubensis*, *Peronospora belbahrii*, *Bremia lactucae*, *Peronospora lamii*, *Plasmopara obduscens*, *Pythium* spp., *Pythium cryptoirregulare*, *Pythium aphanidermatum*, *Pythium irregulare*, *Pythium sylvaticum*, *Pythium myriotylum*, *Pythium ultimum*, *Phytophthora* spp., *Phytophthora capsici*, *Phytophthora nicotianae*, *Phytophthora infestans*, *Phytophthora tropicalis*, *Phytophthora sojae*, *Fusarium* spp., *Fusarium graminearum*, *Fusarium solani*, *Fusarium oxysporum*, *Fusarium graminicola*, *Fusarium virguliforme*,

*Gibberella zeae, Colletotrichum graminicola, Penicillium* spp., *Phakopsora* spp., *Phakopsora meibomiae, Phakopsora pachyrizi, Puccinia triticina, Puccinia recondita, Puccinia striiformis, Puccinia graminis, Puccinia* spp., *Sclerotium* spp., *Sclerotinia* spp., *Venturia inaequalis, Verticillium* spp., *Erwinia amylovora, Monilinia* spp., *Monilinia fructicola, Monilinia lax*, and *Monilinia fructigena*.

In some embodiments, the fungal pest is selected from the group consisting of *Botrytis cinerea, Cercospora sojina, Alternaria solani, Rhizoctonia solani, Erysiphe necator, Podosphaera xanthii, Colletotrichum cereale, Plasmopara viticola, Peronospora belbahrii, Pythium aphanidermatum, Pythium sylvaticum, Pythium myriotylum, Pythium ultimum, Phytophthora nicotianae, Phytophthora infestans, Phytophthora tropicalis, Phytophthora sojae, Fusarium graminearum, Fusarium solani, Phakopsora pachyrizi*, and *Venturia inaequalis*

In further embodiments, the fungal pathogen is *Phakopsora* sp., including *Phakopsora pachyrhizi* and/or *Phakopsora meibomiae*.

Examples of fungal plant conditions and diseases caused by fungal pests include, but are not limited to, Asian Soybean Rust (ASR), gray mold, leaf spot, Frogeye Leaf Spot, Early Blight, Damping off complex, Brown Patch, black scurf, root rot, belly rot, sheath blight, Powdery Mildew, Anthracnose leaf spot, Downy Mildew, *Pythium* Blight, Late Blight, *Fusarium* Head Blight, sudden death syndrome (SDS),

*Fusarium* Wilt, Corn Stalk Rot, Brown Rust, Black Rust, Yellow Rust, Wheat Rust, Rust, Apple Scab, *Verticillium* Wilt, Fire Blight, and Brown Rot.

B. Methods of Controlling Plant Pests and Treating or Preventing Plant Disease

Provided herein are methods for controlling plant pests comprising applying to a plant an effective amount of at least one bacterial strain provided herein or an active variant thereof, and/or a composition derived therefrom wherein the bacterial strain and/or the composition derived therefrom controls the plant pest, such as an insect or nematode pest. Also provided herein are methods of reducing susceptibility to a plant pest and/or increasing resistance to a plant pest comprising applying to a plant having a plant pest, a plant disease or damage caused by a plant pest or damage or at risk of developing a plant disease or damage caused by a plant pest an effective amount of at least one bacterial strain provided herein or an active variant thereof, and/or a composition derived therefrom wherein the bacterial strain and/or the composition derived therefrom controls the plant pest. Provided herein are methods of treating or preventing a plant disease or damage comprising applying to a plant having a plant disease or damage or at risk of developing a plant disease or damage an effective amount of at least one bacterial strain provided herein or an active variant thereof, and/or a composition derived therefrom wherein the bacterial strain and/or the composition derived therefrom controls a plant pest that causes the plant disease or damage. In particular embodiments, the plant damage is caused by an insect pest, such as a coleopteran pest. In certain embodiments, the bacterial strain provided herein or active variant thereof may comprise a cell of at least one of AIP045885, AIP075655, AIP09474, AIP024525, AIP033287, AIP093798, AIP061639, AIP082862, AIP058187, AIP059286, AIP036706, or an active variant of any thereof; or a spore, or a forespore or a combination of cells, forespores and/or spores from any one of AIP045885, AIP075655, AIP09474, AIP024525, AIP033287, AIP093798, AIP061639, AIP082862, AIP058187, AIP059286, AIP036706, or an active variant of any thereof.

In some embodiments, the effective amount of the bacterial strain or active variant thereof comprises at least about $10^{12}$ to $10^{16}$ CFU per hectare or least about $10^4$ to $10^{16}$ CFU per hectare, or least about $10^5$ to $10^{11}$ CFU per hectare. In some embodiments, the composition is derived from a bacterial strain provided herein or active variant thereof which may comprise a cell of at least one of AIP045885, AIP075655, AIP09474, AIP024525, AIP033287, AIP093798, AIP061639, AIP082862, AIP058187, AIP059286, AIP036706, or an active variant of any thereof, or a spore, or a forespore or a combination of cells, forespores and/or spores from any one of AIP045885, AIP075655, AIP09474, AIP024525, AIP033287, AIP093798, AIP061639, AIP082862, AIP058187, AIP059286, AIP036706, or an active variant of any thereof.

Any of the bacterial strains provided herein, active variants thereof, or compositions derived therefrom can control one, two, three, four, five, or more plant pests described herein. In some methods, the bacterial strain controls one, two, three, four, five or more insect pests, such as coleopteran pests. In some embodiments, any of the bacterial strains provided herein or active variants thereof can have activity against a combination of insect pests and other plant pests, including fungi, viruses or viroids, bacteria, insects, nematodes, and protozoa pests. The bacterial strain provided herein or an active variant thereof can be employed with any plant species susceptible to a plant pest of interest.

Examples of diseases causes by exemplary plant pests are provided in Table 1. Also provided are non-limiting exemplary crop species that are susceptible to the plant diseases caused by the pests. For example, Table 1 shows that *Bortrytis cinerea* causes gray mold on all flowering crops. Therefore, a bacterial strain provided herein or active variant thereof that controls *Bortrytis cinerea* can be applied to a plant having gray mold or at risk of developing gray mold in order to treat or prevent gray mold in the plant. Similarly, Table 1 shows that *Rhizoctonia solani* causes Damping off complex in corn, Damping off complex in soybean, Brown Patch in turf, and Damping off complex in ornamentals. Therefore, a bacterial strain provided herein or active variant thereof that controls *Rhizoctonia solani* can be applied to a plant having Damping off complex and/or brown patch or at risk of developing Damping off complex and/or brown patch in order to treat or prevent Damping off complex and/or brown patch in the plant. In yet another example, Table 1 shows that *Colletotrichum cereale, Apiognomonia errabunda, Apiognomonia veneta, Colletotrichum gloeosporiodes, Discula fraxinea* cause Anthracnose leaf spot. Therefore, a bacterial strain provided herein or active variant thereof that controls one or more of *Colletotrichum cereale, Apiognomonia errabunda, Apiognomonia veneta, Colletotrichum gloeosporiodes, Discula fraxinea* can be applied to a plant having Anthracnose leaf spot or at risk of developing Anthracnose leaf spot in order to treat or prevent Anthracnose leaf spot in the plant.

TABLE 1

| Causal Pest | Disease | Crop-species |
|---|---|---|
| *Botrytis cinerea* | gray mold | all flowering crops |
| *Cersospora* spp | Leaf Spot | Ornamentals |
| *Cercospora sojina* | Frogeye leaf spot | Soybeans |
| *Cercospora beticola* | | beets, spinach, chard |
| *Alternaria solani* | Early Blight | solanaceous plants |
| *Rhizoctonia solani* | Damping off complex | Corn |
| *Rhizoctonia solani* | Damping off complex | Soybean |
| *Rhizoctonia solani* | Brown Patch | Turf |
| *Rhizoctonia solani* | Damping off complex | Ornamentals |
| *Rhizoctonia solani* | black scurf | potato |
| *Rhizoctonia solani* | root rot | sugar beet |
| *Rhizoctonia solani* | belly rot | cucurbit |
| *Rhizoctonia solani* | sheath blight | rice |
| *Blumeria graminis* f. sp. *Tritici* | Powdery Mildew | Wheat |
| *Erysiphe necator* | Powdery Mildew | Grape |
| *Podosphaera xanthii* | Powdery Mildew | Cucurbit |
| *Golovinomyces cichoracearum* | Powdery Mildew | Ornamentals |
| *Erysiphe lagerstroemiae* | Powdery Mildew | Ornamentals |
| *Sphaerotheca pannosa* | Powdery Mildew | Ornamentals |
| *Colletotrichum cereale* | Anthracnose leaf spot | Turf/grasses/cereal |
| *Apiognomonia errabunda* | Anthracnose leaf spot | Turf/grasses/cereal |
| *Apiognomonia veneta* | Anthracnose leaf spot | Turf/grasses/cereal |
| *Colletotrichum gloeosporiodes* | Anthracnose leaf spot | Turf/grasses/cereal |
| *Discula fraxinea* | Anthracnose leaf spot | Turf/grasses/cereal |
| *Plasmopara viticola* | Downy Mildew | Grape |
| *Pseudoperonospora cubensis* | Downy Mildew | Cucurbit |
| *Peronospora belbahrii* | Downy Mildew | Basil |
| *Bremia lactucae* | Downy Mildew | Lettuce |
| *Peronospora lamii* | Downy Mildew | Coleus |
| *Plasmopara obduscens* | Downy Mildew | Impatiens |
| *Pythium cryptoirregulare* | Damping off complex | Ornamental Plants |
| *Pythium aphanidermatum* | Pythium Blight/ Damping off complex | turf/ornamentals/row crop |
| *Pythium irregulare* | Damping off complex | turf/ornamentals/row crop |
| *Pythium sylvaticum* | Damping off complex | turf/ornamentals/row crop |
| *Pythium myriotylum* | Damping off complex | turf/ornamentals/row crop |
| *Pythium ultimum* | Pythium Blight/ Damping off complex | turf/ornamentals/row crop |
| *Phytophthora capsici* | | cucurbit/pepper |
| *Phytophthora nicotianae* | | ornamental plants |
| *Phytophthora infestans* | Late Blight | solanaceous plant |
| *Phytophthora tropicalis* | | ornamental plants/peppers/ tropical nut trees |
| *Phytophthora sojae* | | Soybean |
| *Fusarium graminearum* | Fusarium Head Blight | Cereals-Wheat |
| *Fusarium solani* | SDS | Soybean |
| *Fusarium oxysporum* | Fusarium Wilt | Herbaceous Plants |
| *Fusarium graminicola* | Corn Stalk Rot | Maize |
| *Gibberella zeae* | Corn Stalk Rot | Maize |
| *Colletotrichum graminicola* | Corn Stalk Rot | Maize |
| *Phakopsora pachyrizi* | Asian Soybean Rust | Soybean |
| *Puccinia triticina* | Brown Rust | Cereals |
| *Puccinia recondita* | Black Rust | Cereals |
| *Puccinia striiformis* | Yellow Rust | Cereals |
| *Puccinia graminis* | Wheat Rust | Cereals |
| *Puccinia* spp. | Rust | Ornamentals |
| *Venturia inaequalis* | Apple Scab | Malus |
| *Verticillium* spp | Verticillium Wilt | All |
| *Erwinia amylovora* | Fire Blight | Rosacea family |
| *Monilinia fructicola* | Brown Rot | Stone Fruits |
| *Monilinia laxa* | Brown Rot | Stone Fruits |
| *Monilinia fructigena* | Brown Rot | Stone Fruits |

In specific embodiments, the bacterial strain provided herein or active variants thereof controls one or more nematode pests. For example, the bacterial strain or active variants thereof can control or treat root knot nematodes, (*Meloidogyne* spp.). Plant parasitic nematodes may attack the roots, stem, foliage and flowers of plants. All plant parasitic nematodes have piercing mouthparts called stylets. The presence of a stylet is the key diagnostic sign differentiating plant parasitic nematodes from all other types of nematodes. Typical root symptoms indicating nematode attack are root knots or galls, root lesions, excessive root branching, injured root tips and stunted root systems. Symptoms on the above-ground plant parts indicating root infection are a slow decline of the entire plant, wilting even with ample soil moisture, foliage yellowing and fewer and smaller leaves. These are, in fact, the symptoms that would appear in plants deprived of a properly functioning root system. Bulb and stem nematodes produce stem swellings and shortened internodes. Bud and leaf nematodes distort and kill bud and leaf tissue. In some cases, such as with SCN, yield loss may take place with no visible symptoms.

The term "treat" or "treating" or its derivatives includes substantially inhibiting, slowing, or reversing the progression of a condition, substantially ameliorating symptoms of a condition or substantially preventing the appearance of symptoms or conditions brought about by the insect pest, or the pathogen or pest that causes the plant disease.

The terms "controlling" a plant pest refers to one or more of inhibiting or reducing the growth, feeding, fecundity, reproduction, and/or proliferation of a plant pest or killing (e.g., causing the morbidity or mortality, or reduced fecundity) of a plant pest. As such, a plant treated with the bacterial strain provided herein and/or a composition derived therefrom may show a reduced infestation of pests, or reduced damage caused by pests by a statistically significant amount. In particular embodiments, "controlling" and "protecting" a plant from a pest refers to one or more of inhibiting or reducing the growth, germination, reproduction, and/or proliferation of a pest; and/or killing, removing, destroying, or otherwise diminishing the occurrence, and/or activity of a pest. As such, a plant treated with the bacterial strain provided herein and/or a composition derived therefrom may show a reduced severity or reduced development of disease or damage in the presence of plant pests by a statistically significant amount.

The term "prevent" and its variations means the countering in advance of bacterial, fungal, viral, insect or other pest growth, proliferation, infestation, spore germination, and hyphae growth. In this instance, the composition is applied before exposure to the plant pests.

The term "ameliorate" and "amelioration" relate to the improvement in the treated plant condition brought about by the compositions and methods provided herein. The improvement can be manifested in the forms of a decrease in pest growth and/or an improvement in the damaged or diseased plant height, weight, number of leaves, root system, or yield. In general, the term refers to the improvement in a damaged or diseased plant's physiological state.

The term "inhibit" and all variations of this term is intended to encompass the restriction or prohibition of bacterial, fungal, viral, nematode, insect, or any other pest growth, as well as spore germination.

The term "eliminate" relates to the substantial eradication or removal of bacteria, fungi, viruses, nematodes, insects, or any other pests by contacting them with the composition of the invention, optionally, according to the methods of the invention described below.

The terms "delay", "retard" and all variations thereof are intended to encompass the slowing of the progress of bacterial, fungal, viral, nematode, insect, or any other pest growth, and spore germination. The expression "delaying the onset" is interpreted as preventing or slowing the progression of bacterial, fungal, viral, nematodes, insect, or any other pest growth, infestation, infection, spore germination and hyphae growth for a period of time, such that said bacterial, fungal, viral, nematode, insect, or any other pest growth, infestation, infection, spore germination and hyphae growth do not progress as far along in development, or appear later than in the absence of the treatment according to the invention.

A plant, plant part, or area of cultivation treated with the bacterial strain provided herein or an active variant thereof may show a reduced severity or reduced development of disease or damage in the presence of plant pests by a statistically significant amount. A reduced severity or reduced development of disease or damage can be a reduction of about 10% to about 20%, about 20% to about 30%, about 30% to about 40%, about 40% to about 50%, about 50% to about 60%, about 60% to about 70%, about 70% to about 80%, about 80% to about 90%, or about 90% to about 100% when compared to non-treated control plants. In other instances, the plant treated with a bacterial strain provided herein or an active variant thereof may show a reduced severity or reduced development of disease or damage in the presence of a plant pest of at least about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% greater when compared to non-treated control plants. Methods for assessing plant damage or disease severity are known, and include, measuring percentage of damaged or diseased leaf area (Godoy et al. (2006) *Fitopatol. Bras.* 31(1) 63-68 or by measuring uredinia counts.

A plant, plant part, or area of cultivation treated with the bacterial strain provided herein or an active variant thereof may show a reduction of plant pests, including insect and/or nematode pests. A reduction of plant pests can be a reduction of about 10% to about 20%, about 20% to about 30%, about 30% to about 40%, about 40% to about 50%, about 50% to about 60%, about 60% to about 70%, about 70% to about 80%, about 80% to about 90%, or about 90% to about 100% when compared to non-treated control plants. In other instances, the plant treated with a bacterial strain provided herein or an active variant thereof may show a reduction of plant pests of at least about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% greater when compared to non-treated control plants. Methods for measuring the number of plant pests are known, and include, counting the number of pests, or contacting plants with one or more pests and determining the plant's ability to survive and/or cause the death of the pests. See, for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743,477, all of which are herein incorporated by reference in their entirety.

In some embodiments, the bacterial strains and active variants thereof, and/or a composition derived therefrom, provided herein have pesticidal activity against an insect pest (i.e., insecticidal activity). In some of these embodiments, the insecticidal activity is activity against a coleopteran species. In one embodiment, the insecticidal activity is against a lepidopteran insect. In one embodiment, the insecticidal activity is against a hemipteran species. In some embodiments, the insecticidal activity is against one or more insect pests, such as the Western corn rootworm, Southern corn rootworm, Northern corn rootworm, Mexican corn rootworm, the Colorado potato beetle, the sweet potato weevil, or the Southern green stink bug.

In specific embodiments, the bacterial strains, active variants thereof, and/or a composition derived therefrom provided herein reduce the damage or disease symptoms resulting from a plant pest by a statistically significant amount, including for example, at least about 10% to at least about 20%, at least about 20% to about 50%, at least about 10% to about 60%, at least about 30% to about 70%, at least about 40% to about 80%, or at least about 50% to about 90% or greater. Hence, the methods of the invention can be utilized to protect plants from disease or damage caused by plant pests.

Assays that quantitate damage or disease resistance following pest infestation are commonly known in the art. See, for example, U.S. Pat. No. 5,614,395, herein incorporated by reference. Such techniques include, measuring over time, the average lesion diameter, the pest biomass, and the overall percentage of decayed plant tissues. For example, a plant either expressing a pesticidal polypeptide or having a pesticidal composition applied to its surface shows a decrease in tissue necrosis (i.e., lesion diameter) or a decrease in plant death following challenge with a pest when compared to a control plant that was not exposed to the pesticidal composition. Alternatively, pesticidal activity can be measured by a decrease in pest biomass. For example, a plant expressing a pesticidal polypeptide or exposed to a pesticidal composition is challenged with a pest of interest. Over time, tissue samples from the pest-infested tissues are obtained and RNA is extracted. The percent of a specific pest RNA transcript relative to the level of a plant specific transcript allows the level of pest biomass to be determined. See, for example, Thomma et al. (1998) *Plant Biology* 95:15107-15111, herein incorporated by reference.

Furthermore, in vitro pesticidal assays include, for example, the addition of varying concentrations of the pesticidal composition to paper disks and placing the disks on agar containing a suspension of the pest of interest. Following incubation, clear inhibition zones develop around the discs that contain an effective concentration of the pesticidal composition (Liu et al. (1994) *Plant Biology* 91:1888-1892, herein incorporated by reference). Additionally, microspectrophotometrical analysis can be used to measure the in vitro pesticidal properties of a composition (Hu et al. (1997) *Plant Mol. Biol.* 34:949-959 and Cammue et al. (1992) *J. Biol. Chem.* 267: 2228-2233, both of which are herein incorporated by reference).

C. Methods of Inducing Pest and/or Disease Resistance in Plants and/or for Improving an Agronomic Trait of Interest Compositions and methods for inducing pest and/or disease resistance in a plant, wherein the disease is caused by a plant pest, are also provided. Accordingly, the compositions and methods are also useful in protecting plants against any type of plant pest, including fungal pests, viruses, nematodes, and insects. Provided herein are methods of inducing resistance against a plant pest comprising applying to a plant that is susceptible to infection or infestation by a plant pest or a plant disease caused by the plant pest an effective amount of at least one bacterial strain provided herein, an active variant thereof, and/or a composition derived therefrom. In certain embodiments, the bacterial strain provided herein, the active variant thereof, and/or the composition derived therefrom may comprise a cell of at least one of AIP045885, AIP075655, AIP09474, AIP024525, AIP024525, AIP033287, AIP093798, AIP061639, AIP082862, AIP058187, AIP059286, AIP036706, or an active variant of any thereof; or a spore, or a forespore or a combination of cells, forespores and/or spores from any one of AIP045885, AIP075655, AIP09474, AIP024525, AIP033287, AIP093798, AIP061639, AIP082862, AIP058187, AIP059286, AIP036706, or an active variant of any thereof. In certain embodiments, the bacterial strain provided herein, the active variant thereof, and/or the composition derived therefrom promotes a defensive response to the pest that causes the plant disease or damage. In some embodiments, the effective amount of the bacterial strain provided herein or active variant thereof comprises at least about $10^5$ to $10^{12}$ CFU per hectare. In some embodiments, the effective amount of the bacterial strain provided herein or active variant thereof comprises at least about $10^{12}$ to $10^{16}$ CFU per hectare.

A defensive response in the plant can be triggered after applying the bacterial strain provided herein, the active variant thereof, and/or the composition derived therefrom to the plant, but prior to pest challenge and/or after pest challenge of the plant treated with the bacterial strain provided herein, the active variant thereof, and/or the composition derived therefrom.

In some methods, the bacterial strain provided herein, the active variant thereof, and/or the composition derived therefrom induces resistance to one, two, three, four, five or more plant pests described herein. In other methods, the bacterial strain provided herein, the active variant thereof, and/or the composition derived therefrom induces resistance to one, two, three, four, five or more insect pests, fungal plant pests, or nematode pests described herein.

By "disease resistance" is intended that the plants avoid the disease symptoms that result from plant-pest interactions. That is, pests are prevented from causing plant diseases and the associated disease symptoms, or alternatively, the disease symptoms caused by the pest are minimized or lessened as compared to a control. By "pest resistance" can be intended that the plants avoid the symptoms that result from infection or infestation of a plant by a pest. That is, pests are prevented from causing plant diseases and the associated disease symptoms, or alternatively, the disease symptoms caused by the pest are minimized or lessened as compared to a control. Further provided are methods of improving plant health and/or improving an agronomic trait of interest comprising applying to a plant an effective amount of at least one bacterial strain provided herein or an active variant thereof or an active derivative thereof. In certain embodiments, the bacterial strain provided herein or active variant thereof may comprise a cell of at least one of AIP045885, AIP075655, AIP09474, AIP024525, AIP033287, AIP093798, AIP061639, AIP082862, AIP058187, AIP059286, AIP036706, or an active variant of any thereof; or a spore, or a forespore or a combination of cells, forespores and/or spores from any one of AIP045885, AIP075655, AIP09474, AIP024525, AIP033287, AIP093798, AIP061639, AIP082862, AIP058187, AIP059286, AIP036706, or an active variant of any thereof. In some embodiments, the effective amount of the bacterial strain provided herein or active variant thereof comprises at least about $10^5$ to $10^{12}$ CFU per hectare. In some embodiments, the effective amount of the bacterial strain provided herein or active variant thereof comprises at least about $10^{12}$ to $10^{16}$ CFU per hectare. In some embodiments, the composition is derived from a bacteria strain provided herein or active variant thereof which may comprise a cell of at least one of AIP045885, AIP075655, AIP09474, AIP024525, AIP033287, AIP093798, AIP061639, AIP082862, AIP058187, AIP059286, AIP036706, or an active variant of any thereof, or a spore, or a forespore or a combination of cells, forespores and/or spores from any one of AIP045885, AIP075655, AIP09474, AIP024525, AIP033287, AIP093798, AIP061639, AIP082862, AIP058187, AIP059286, AIP036706, or an active variant of any thereof.

In particular embodiments, the agronomic trait of interest that is improved by the bacterial strains or active variants thereof described herein is improved plant health. By "improved plant health" is meant increased growth and/or yield of a plant, increased stress tolerance and/or decreased herbicide resistance, to name a few. Increased stress tolerance refers to an increase in the ability of a plant to decrease or prevent symptoms associated with one or more stresses. The stress can be a biotic stress that occurs as a result of damage done to plants by other living organisms such as a pest (for example, bacteria, viruses, fungi, parasites), insects, nematodes, weeds, cultivated or native plants). The stress can also be an abiotic stress such as extreme temperatures (high or low), high winds, drought, salinity, chemical toxicity, oxidative stress, flood, tornadoes, wildfires, radiation and exposure to heavy metals. Non-limiting examples of improved agronomic traits are disclosed elsewhere herein. In specific embodiments, an effective amount of the bacterial strain, active variant thereof, and/or a composition derived therefrom improves plant health or improves an agronomic trait of interest by a statistically significant amount, including for example, at least about 10% to at least about 20%, at least about 20% to about 50%, at least about 10% to about 60%, at least about 30% to about 70%, at least about 40% to about 80%, or at least about 50% to about 90% or greater.

D. Methods of Application to a Plant or Plant Part

The bacterial strains provided herein, the active variant thereof, and/or the composition derived therefrom are applied in an effective amount. An effective amount of a bacterial strain provided herein, the active variant thereof, and/or the composition derived therefrom is an amount sufficient to control, treat, prevent, inhibit the pest, such as an insect pest, and/or improve an agronomic trait of interest. In specific embodiments, an effective amount of a bacterial strain provided herein, the active variant thereof, and/or the composition derived therefrom is an amount sufficient to control, treat, prevent, inhibit a pest that causes plant disease or damage and/or reduce plant disease severity or reduce plant disease development. In other embodiments, the effective amount of the bacterial strain provided herein, the active variant thereof, and/or the composition derived therefrom is an amount sufficient to improve an agronomic trait of interest and/or to promote or increase plant health, growth or yield of a plant susceptible to a disease and/or infection by a plant pest or infestation by a plant pest, such as an insect pest. The rate of application of the bacterial strain provided herein, the active variant thereof, and/or the composition derived therefrom may vary according to the pest being targeted, the crop to be protected, the efficacy of the bacterial strain provided herein, the active variant thereof, and/or the composition derived therefrom, the severity of the disease, the climate conditions, the agronomic trait of interest to improve, and the like. The methods provided herein can comprise a single application of at least one bacterial strain provided herein or an active variant thereof and/or a composition derived therefrom to a plant, plant part, or area of cultivation or multiple applications of at least one bacterial strain provided herein or an active variant thereof to a plant, plant part, or area of cultivation.

Generally, the rate of bacterial strain provided herein or active variant thereof is $10^7$ to $10^{16}$ colony forming units (CFU) per hectare. In other embodiments, for a field inoculation, the rate of bacterial strain provided herein or active variant thereof application is $3 \times 10^7$ to $1 \times 10^{11}$ colony forming units (CFU) per hectare. (This corresponds to about 1 Kg to 10 kg of formulated material per hectare). In other embodiments, for a field inoculation, the rate of bacterial strain provided herein or active variant thereof application is $3 \times 10^7$ to $1 \times 10^{16}$ colony forming units (CFU) per hectare; about $1 \times 10^{12}$ to about $1 \times 10^{13}$ colony forming units (CFU) per hectare, about $1 \times 10^{13}$ to about $1 \times 10^{14}$ colony forming units (CFU) per hectare, about $1 \times 10^{14}$ to about $1 \times 10^{15}$ colony forming units (CFU) per hectare, about $1 \times 10^{15}$ to about $1 \times 10^{16}$ colony forming units (CFU) per hectare, about $1 \times 10^{16}$ to about $1 \times 10^{17}$ colony forming units (CFU) per hectare; about $1 \times 10^4$ to about $1 \times 10^{14}$ colony forming units (CFU) per hectare; about $1 \times 10^5$ to about $1 \times 10^{13}$ colony forming units (CFU) per hectare; about $1 \times 10^6$ to about $1 \times 10^{12}$ colony forming units (CFU) per hectare; about $1 \times 10^9$ to about $1 \times 10^{11}$ colony forming units (CFU) per hectare; or about $1 \times 10^9$ to about $1 \times 10^{11}$ colony forming units (CFU) per hectare. In other embodiments, for a field inoculation, the rate of bacterial strain provided herein or active variant thereof application is at least about $1 \times 10^4$, about $1 \times 10^5$, about $1 \times 10^6$, about $1 \times 10^7$, about $1 \times 10^8$, about $1 \times 10^9$, about $1 \times 10^{10}$, about $1 \times 10^{11}$, about $1 \times 10^{12}$ $1 \times 10^{13}$, about $1 \times 10^{14}$, $1 \times 10^{15}$, about $1 \times 10^{16}$, or about $1 \times 10^{17}$ colony forming units (CFU) per hectare. In other embodiments, for a field inoculation, the rate of bacterial strain provided herein or active variant thereof application is at least $1 \times 10^7$ to at least about $1 \times 10^{12}$ CFU/hectare. In specific embodiments, the bacterial strain provided herein or active variant thereof applied comprises the strain deposited as AIP045885, AIP075655, AIP09474, AIP024525, AIP033287, AIP093798, AIP061639, AIP082862, AIP058187, AIP059286, AIP036706, or an active derivative of any thereof, or a spore, or a forespore or a combination of cells, forespores and/or spores from any one of AIP045885, AIP075655, AIP09474, AIP024525, AIP033287, AIP093798, AIP061639, AIP082862, AIP058187, AIP059286, AIP036706, or an active derivative of any thereof.

In some embodiments, the applied composition is derived from a bacterial strain or active variant thereof comprising a strain deposited as AIP045885, AIP075655, AIP09474, AIP024525, AIP033287, AIP093798, AIP061639, AIP082862, AIP058187, AIP059286, AIP036706, or an active derivative of any thereof, or a spore, or a forespore or a combination of cells, forespores and/or spores from any one of AIP045885, AIP075655, AIP09474, AIP024525, AIP033287, AIP093798, AIP061639, AIP082862, AIP058187, AIP059286, AIP036706, or an active derivative of any thereof. In some embodiments, the applied composition may be a substantially pure culture, whole cell broth, supernatant, filtrate, extract, or compound derived from a bacterial strain of the invention or an active variant thereof. The applied composition may be applied alone or in combination with another substance, in an effective amount for controlling a plant pest or for improving an agronomic trait of interest in a plant.

An effective amount of the applied composition is the quantity of microorganism cells, supernatant, whole cell broth, filtrate, cell fraction or extract, metabolite, and/or compound alone or in combination with another pesticidal substance that is sufficient to modulate plant pest infestation or the performance of an agronomic trait of interest in the plant. The amount that will be within an effective range can be determined by laboratory or field tests by one skilled in the art.

In some embodiments, when the composition is applied directly to the seed, the effective amount is a concentration of about 0.05-25%, or about 0.1-20%, or about 0.5-15%, or about 1-10%, or about 2-5% of the active ingredient per 100 g of seed. In some embodiments, the effective amount is about 0.5-1% of the active ingredient per 100 g of seed.

In some embodiments, when the composition is applied to the soil by, for example, in furrow, the effective amount is about 0.1-50 oz. of the active ingredient per 1000 ft row. In another embodiment, the effective amount for soil application is about 1-25 oz. of the active ingredient per 1000 ft row. In another embodiment, the effective amount is about 2-20 oz, or about 3-15 oz, or about 4-10 oz, or about 5-8 oz, of the active ingredient per 1000 ft row. In yet another embodiment, the effective amount is about 14 or 28 oz of the active ingredient per 1000 ft row.

Any appropriate agricultural application rate for a biocide can be applied in combination with the bacterial strain provided herein or active variant thereof disclosed herein. Methods to assay for the effective amount of the bacterial strain provided herein or active variant thereof include, for example, any statistically significant increase in the control of the pest targeted by the bacterial strain, active variant thereof, and/or a composition derived therefrom. Methods to assay for such control are known. Moreover, a statistically significant increase in plant health, yield and/or growth can occur upon application of an effective amount of the bacterial strain provided herein or active variant thereof when compared to the plant health, yield and/or growth that occurs when no bacterial strain provided herein or active variant thereof is applied.

Further provided is a method for controlling or inhibiting the growth of a plant pest, such as those that cause plant disease, by applying a composition comprising a bacterial strain provided herein or active variant thereof provided herein (i.e., a cell of at least one of AIP045885, AIP075655, AIP09474, AIP024525, AIP033287, AIP093798, AIP061639, AIP082862, AIP058187, AIP059286, AIP036706, or an active variant of any thereof, or a spore, or a forespore or a combination of cells, forespores and/or spores from any one of AIP045885, AIP075655, AIP09474, AIP024525, AIP033287, AIP093798, AIP061639, AIP082862, AIP058187, AIP059286, AIP036706, or an active variant of any thereof) and/or a composition derived from a bacteria strain or active variant described above. By "applying" is intended contacting an effective amount of the bacterial strain provided herein or active variant thereof to a plant, area of cultivation, and/or seed with one or more of the bacterial strains provided herein or active variant thereof so that a desired effect is achieved. Furthermore, the application of the bacterial strain provided herein or active variant thereof can occur prior to the planting of the crop (for example, to the soil, the seed, or the plant). In a specific embodiment, the application of the bacterial strain provided herein or active variant thereof and/or a composition derived therefrom is a foliar application. Therefore, a further embodiment of the invention provides a method for controlling or inhibiting the growth of a plant pest by applying the population of bacterial strain provided herein or active variant thereof and/or a composition derived therefrom to an environment in which the plant pest may grow. The application may be to the plant, to parts of the plant, to the seeds of the plants to be protected, or to the soil in which the plant to be protected are growing or will grow. Application to the plant or plant parts may be before or after harvest. Application to the seeds will be prior to planting of the seeds.

In some embodiments, an effective amount of at least one bacterial strain provided herein or active variant thereof and/or a composition derived therefrom provided herein is used as a foliar application to control or inhibit growth of one or more nematode pathogens from the group consisting of Southern Root-Knot nematode (*Meloidogyne incognita*), Javanese Root-Knot nematode (*Meloidogyne javanica*), Northern Root-Knot Nematode (*Meloidogyne hapla*) and Peanut Root-Knot Nematode.

In some embodiments, an effective amount of at least one bacterial strain provided herein or active variant thereof provided herein and/or a composition derived therefrom is used as a foliar or soil or seed application to control or inhibit growth of one or more insect pests. For example, an effective amount of at least one bacterial strain provided herein, or active variant thereof, can be used as a foliar application to control or inhibit growth of coleopteran insects including corn rootworms, Western corn rootworm, Colorado potato beetle, weevils, and the sweetpotato weevil. In other embodiments, an effective amount of at least one bacterial strain provided herein or active variant thereof and/or a composition derived therefrom provided herein is applied to the soil in which the plants to be protected are growing or will grow to control or inhibit growth of one or more nematode or nematode pest. In specific embodiments, an effective amount of at least one bacterial strain provided herein or active variant thereof and/or a composition derived therefrom provided herein is applied to plant seed for inhibiting (inhibiting growth, feeding, fecundity, or viability), suppressing (suppressing growth, feeding, fecundity, or viability), reducing (reducing the pest infestation, reducing the pest feeding activities on a particular crop) or killing (causing the morbidity, mortality, or reduced fecundity of) a plant pest (e.g., an insect pest, such as a coleopteran pest).

In other embodiments, an effective amount of at least one bacterial strain provided herein or active variant thereof and/or a composition derived therefrom provided herein is applied to the plant propagule (i.e. seed, slip, stem cutting, corn etc.) from which the plant to be protected are growing or will grow to control or inhibit growth of one or more plant pests. For example, an effective amount of at least one bacterial strain provided herein, or active variant thereof, and/or a composition derived therefrom, can be applied to the plant propagule to control or inhibit growth of insect pests (e.g., coleopteran insects including corn rootworms, Western corn rootworm, Colorado potato beetle, weevils, and the sweetpotato weevil). In specific embodiments, an effective amount of at least one bacterial strain provided herein, or active variant thereof, and/or a composition derived therefrom, can be applied to the plant tissue (including fruit) before or after harvest to control or inhibit growth of a plant pest (e.g., insect pest, such as coleopteran insects including corn rootworms, Western corn rootworm, Colorado potato beetle, weevils, and the sweetpotato weevil). In some embodiments, an effective amount of a bacterial strain provided herein, or active variant thereof, and/or a composition derived therefrom, provided herein is applied to the plant tissue (including fruit) after harvest to control or inhibit growth of one or more nematode pests.

In other embodiments, an effective amount of at least one bacterial strain provided herein, or active variant thereof, and/or a composition derived therefrom provided herein is applied to the soil in which the plant to be protected are growing or will grow to control or inhibit growth of one or more pests selected from the group consisting of Southern Root-Knot nematode (*Meloidogyne incognita*), Javanese Root-Knot nematode (*Meloidogyne javanica*), Northern Root-Knot Nematode (*Meloidogyne hapla*) and Peanut Root-Knot Nematode.

In some embodiments, an effective amount of a bacterial strain provided herein or active variant thereof and/or a composition derived therefrom provided herein is applied to the plant after harvest to control or inhibit growth of one or more pests selected from the group consisting of Southern Root-Knot nematode (*Meloidogyne incognita*), Javanese Root-Knot nematode (*Meloidogyne javanica*), Northern Root-Knot Nematode (*Meloidogyne hapla*) and Peanut Root-Knot Nematode.

As used Herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species.

In specific embodiments, the application of the bacterial strain provided herein or active variant thereof (i.e., a cell of at least one of AIP045885, AIP075655, AIP09474, AIP024525, AIP033287, AIP093798, AIP061639, AIP082862, AIP058187, AIP059286, AIP036706, or an active variant of any thereof, or a spore, or a forespore or a combination of cells, forespores and/or spores from any one of AIP045885, AIP075655, AIP09474, AIP024525, AIP033287, AIP093798, AIP061639, AIP082862, AIP058187, AIP059286, AIP036706, or an active variant of any thereof), and/or a composition derived therefrom, is applied to the seeds of a plant, such as the seeds of a corn (maize) plant. Application of the bacterial strain, or an active variant thereof, to corn seed can comprise a concentration of about $10^5$ CFU/gram to about $10^{11}$ CFU/gram, about $10^7$ CFU/gram to about $10^{10}$ CFU/gram, about $10^7$ CFU/gram to about $10^{11}$ CFU/gram, about $10^6$ CFU/gram to about $10^{10}$ CFU/gram, about $10^6$ CFU/gram to about $10^{11}$ CFU/gram, about $10^{11}$ CFU/gram to about $10^{12}$ CFU/gram, about $10^5$ CFU/gram to about $10^{10}$ CFU/gram, about $10^5$ CFU/gram to about $10^{12}$ CFU/gram, about $10^5$ CFU/gram to about $10^6$ CFU/gram, about $10^6$ CFU/gram to about $10^7$ CFU/gram, about $10^7$ CFU/gram to about $10^8$ CFU/gram, about $10^8$ CFU/gram to about $10^9$ CFU/gram, about $10^9$ CFU/gram to about $10^{10}$ CFU/gram, about $10^{10}$ CFU/gram to about $10^{11}$ CFU/gram, or about $10^{11}$ CFU/gram to about $10^{12}$ CFU/gram. In some embodiments, the concentration of the bacterial strain comprises at least about $10^5$ CFU/gram, at least about $10^6$ CFU/gram, at least about $10^7$ CFU/gram, at least about $10^8$ CFU/gram, at least about $10^9$ CFU/gram, at least about $10^{10}$ CFU/gram, at least about $10^{11}$ CFU/gram, at least about $10^{12}$ CFU/gram, or at least about $10^{13}$ CFU/gram. In specific embodiments, the bacterial strain, or active variant thereof, and/or a composition derived therefrom applied to the corn seed is applied in the form of a heterologous seed coating as described elsewhere herein. The concentration and timing of application can vary depending on the conditions and geographical location.

In specific embodiments, the application of the bacterial strain provided herein or active variant thereof (i.e., a cell of at least one of AIP045885, AIP075655, AIP09474, AIP024525, AIP033287, AIP093798, AIP061639, AIP082862, AIP058187, AIP059286, AIP036706, or an active variant of any thereof, or a spore, or a forespore or a combination of cells, forespores and/or spores from any one of AIP045885, AIP075655, AIP09474, AIP024525, AIP033287, AIP093798, AIP061639, AIP082862, AIP058187, AIP059286, AIP036706, or an active variant of any thereof) and/or a composition derived therefrom is applied to the leaves of a soybean plant. The timing of application can vary depending on the conditions and geographical location.

Various methods are provided for controlling a plant pest, such as one that causes a plant disease, in an area of cultivation containing a plant susceptible to the plant pest or a plant disease caused by a plant pest. The method comprises planting the area of cultivation with seeds or plants susceptible to the plant disease or pest; and applying to the plant susceptible to the disease or pest, the seed or the area of cultivation of the plant susceptible to the plant disease or pest an effective amount of at least one bacterial strain provided herein or active variant thereof (i.e., a cell of at least one of AIP045885, AIP075655, AIP09474, AIP024525, AIP033287, AIP093798, AIP061639, AIP082862, AIP058187, AIP059286, AIP036706, or an active derivative of any thereof, or a spore, or a forespore or a combination of cells, forespores and/or spores from any one of AIP045885, AIP075655, AIP09474, AIP024525, AIP033287, AIP093798, AIP061639, AIP082862, AIP058187, AIP059286, AIP036706, or an active variant of any thereof), and/or a composition derived therefrom wherein the effective amount of the bacterial strain provided herein or active variant thereof controls the plant pest without significantly affecting the plant. In specific embodiments, the effective amount comprises at least about $10^{12}$ to $10^{16}$ colony forming units (CFU) per hectare. Further provided is a method for growing a plant susceptible to a plant pest or a plant disease caused by a plant pest. The method comprises applying to a plant susceptible to the disease or pest, a seed, or an area of cultivation of the plant susceptible to the disease or pest an effective amount of a composition comprising at least one bacterial strain provided herein or active variant thereof. In certain embodiments, the bacterial strain provided herein or active variant thereof may comprise a cell of at least one of AIP045885, AIP075655, AIP09474, AIP024525, AIP033287, AIP093798, AIP061639, AIP082862, AIP058187, AIP059286, AIP036706, or an active variant of any thereof; or a spore, or a forespore or a combination of cells, forespores and/or spores from any one of AIP045885, AIP075655, AIP09474, AIP024525, AIP033287, AIP093798, AIP061639, AIP082862, AIP058187, AIP059286, AIP036706, or an active variant of any thereof. Various effective amounts of at least one bacterial strain provided herein or active variant thereof are disclosed elsewhere herein and in one, non-limiting example, the effective amount of the bacterial strain provided herein or active variant thereof comprises at least about $10^{12}$ to $10^{16}$ colony forming units (CFU) per hectare. In some embodiments, the composition is derived from a bacterial strain provided herein or active variant thereof and may comprise a cell of at least one of AIP045885, AIP075655, AIP09474, AIP024525, AIP033287, AIP093798, AIP061639, AIP082862, AIP058187, AIP059286, AIP036706, or an active variant of any thereof, or a spore, or a forespore or a combination of cells, forespores and/or spores from any one of AIP045885, AIP075655, AIP09474, AIP024525, AIP033287, AIP093798, AIP061639, AIP082862, AIP058187, AIP059286, AIP036706, or an active variant of any thereof.

Methods for increasing plant yield are provided. The "yield" of the plant refers to the quality and/or quantity of biomass produced by the plant. By "biomass" is intended any measured plant product. An increase in biomass production is any improvement in the yield of the measured plant product. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not exposed to the bacterial strain provided herein or active variant thereof. A method for increasing yield in a plant is also provided and comprises applying to a crop or an area of cultivation an effective amount of a composition comprising at least one bacterial strain comprising AIP045885, AIP075655, AIP09474, AIP024525, AIP033287, AIP093798, AIP061639, AIP082862, AIP058187, AIP059286, AIP036706, or an active variant of any thereof, a spore or a forespore or a combination of cells, forespores and/or spores from any one of AIP045885, AIP075655, AIP09474, AIP024525, AIP033287, AIP093798, AIP061639, AIP082862, AIP058187, AIP059286, AIP036706, or an active variant of any thereof, wherein said effective amount comprises at least about $10^{12}$ to $10^{16}$ colony forming units (CFU) per hectare, and wherein said composition controls a plant pest, thereby increasing yield. A method for increasing yield in a plant is also provided which comprises applying to a crop or an area of cultivation an effective amount of a composition derived from at least one bacterial strain comprising AIP045885, AIP075655, AIP09474, AIP024525, AIP033287, AIP093798, AIP061639, AIP082862, AIP058187, AIP059286, AIP036706, or an active variant of any thereof, a spore or a forespore or a combination of cells, forespores and/or spores from any one of AIP045885, AIP075655, AIP09474, AIP024525, AIP033287, AIP093798, AIP061639, AIP082862, AIP058187, AIP059286, AIP036706, or an active variant of any thereof, wherein said composition controls a plant pest, thereby increasing yield.

As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc.), a greenhouse, a growth chamber, etc.

In other embodiments, a plant of interest (i.e., plant susceptible to a plant pest or plant disease caused by a plant pest) and/or the area of cultivation comprising the plant, can be treated with a combination of an effective amount of the bacterial strain provided herein, an active variant thereof, and/or a composition derived therefrom, and an effective amount of a biocide or other biocontrol agent. By "treated with a combination of" or "applying a combination of" a bacterial strain provided herein, an active variant thereof, a composition derived therefrom, and a biocide or other biocontrol agent to a plant, area of cultivation or field it is intended that one or more of a particular field, plant, and/or weed is treated with an effective amount of one or more of the bacterial strains provided herein or active variant thereof and one or more biocide or other biocontrol agent so that a desired effect is achieved. Furthermore, the application of one of the bacterial strains provided herein, an active variant thereof, and/or a composition derived therefrom, and the biocide or other biocontrol agent can occur prior to the planting of the crop (for example, to the soil, or the plant). Moreover, the application of the bacterial strains provided herein, an active variant thereof, and/or a composition derived therefrom and the biocide or other biocontrol agent may be simultaneous or the applications may be at different times (sequential), so long as the desired effect is achieved.

In one non-limiting embodiment, the active variant comprises a bacterial strain provided herein that is resistant to one or more biocide. In specific embodiments, the bacterial strain provided herein or active variant thereof (i.e., a cell of at least one of AIP045885, AIP075655, AIP09474, AIP024525, AIP033287, AIP093798, AIP061639, AIP082862, AIP058187, AIP059286, AIP036706, or an active variant of any thereof, or a spore, or a forespore or a combination of cells, forespores and/or spores from any one of AIP045885, AIP075655, AIP09474, AIP024525, AIP033287, AIP093798, AIP061639, AIP082862, AIP058187, AIP059286, AIP036706, or an active variant of any thereof) is resistant to glyphosate. In such methods, a plant, crop, or area of cultivation is treated with a combination of an effective amount of the bacterial strain provided herein or active variant thereof that is resistant to glyphosate and an effective amount of glyphosate, wherein the effective amount of glyphosate is such as to selectively control weeds while the crop is not significantly damaged.

In another non-limiting embodiment, the active variant comprises a bacterial strain provided herein that is resistant to glufosinate. In such methods, a plant, crop, or area of cultivation is treated with a combination of an effective amount of the bacterial strain provided herein or active variant thereof that is resistant to glufosinate and an effective amount of glufosinate, wherein the effective amount of glufosinate is such as to selectively control weeds while the crop is not significantly damaged. In such embodiments, the effective amount of the bacterial strain provided herein or active variant thereof is sufficient to result in a statistically significant increase in plant health, yield, and/or growth when compared to the plant health, yield, and/or growth that occurs when the same concentration of a bacterial strain provided herein or active variant thereof that was not modified to be resistant to glufosinate is applied in combination with the effective amount of the glufosinate or active derivative thereof. In a further embodiment, the bacterial strain provided herein or active variant thereof comprises an effective amount of a cell of at least one of AIP045885, AIP075655, AIP09474, AIP024525, AIP033287, AIP093798, AIP061639, AIP082862, AIP058187, AIP059286, AIP036706, or an active variant of any thereof, or a spore, or a forespore or a combination of cells, forespores and/or spores from any one of AIP045885, AIP075655, AIP09474, AIP024525, AIP033287, AIP093798, AIP061639, AIP082862, AIP058187, AIP059286, AIP036706, or an active variant of any thereof.

V. Biocides for Use in Combination with the Bacterial Strain Provided Herein or Active Variants Thereof As discussed elsewhere herein, the bacterial strain provided herein or active variant thereof and/or a composition derived therefrom can be used in combination with a biocide (i.e., an herbicide, insecticide, fungicide, pesticide, or other crop protection chemical). In such instances, the bacterial strain provided herein or active variant thereof is compatible with the biocide of interest.

By "herbicide, insecticide, fungicide, pesticide, insecticide or other crop protection chemical tolerance or herbicide, fungicide, pesticide, insecticide or other crop protection chemical resistance" is intended the ability of an organism (i.e., the plant and/or the bacterial strain provided herein or active variant thereof etc.) to survive and reproduce following exposure to a dose of the herbicide, insecticide, fungicide, pesticide, insecticide, or other crop protection chemical that is normally lethal to the wild type organism.

Herbicides that can be used in the various methods and compositions discloses herein include glyphosate, ACCase inhibitors (Arloxyphenoxy propionate (FOPS)); ALS inhibitors (Sulfonylurea (SU)), Imidazonlinone (IMI), Pyrimidines (PM)); microtubule protein inhibitor (Dinitroaniline (DNA)); synthetic auxins (Phenoxy (P)), Benzoic Acid (BA), Carboxylic acid (CA)); Photosystem II inhibitor (Triazine (TZ)), Triazinone (TN), Nitriles (NT), Benzothiadiazinones (BZ), Ureas (US)); EPSP Synthase inhibitor (glycines (GC)); Glutamine Synthesis inhibitor (Phosphinic Acid (PA)); DOXP synthase inhibitor (Isoxazolidinone (IA)); HPPD inhibitor (Pyrazole (PA)), Triketone (TE)); PPO inhibitors (Diphenylether (DE), N-phenylphthalimide (NP) (Ary triazinone (AT)); VLFA inhibitors (chloroacetamide (CA)), Oxyacetamide (OA)); Photosystem I inhibitor (Bipyridyliums (BP)); and the like.

Pesticides that can be used in the various methods and compositions disclosed herein include imidacloprid clothianidin, arylpyrazole compounds (WO2007103076); organophosphates, phenyl pyrazole, pyrethoids caramoyloximes, pyrazoles, amidines, halogenated hydrocarbons, carbamates and derivatives thereof, terbufos, chloropyrifos, fipronil, chlorethoxyfos, telfuthrin, carbofuran, imidacloprid, tebupirimfos (U.S. Pat. No. 5,849,320).

Insecticides that can be used used in the various methods and compositions disclosed herein include imidacloprid, Beta-cyfluthrin, cyantraniliprole, diazinon, lambda-cyhalothrin, methiocarb, pymetrozine, pyrifluquinazon, spinetoram, spirotetramat, thiodicarb, and Ti-435, carbamates, sodium channel modulators/voltage dependent sodium channel blockers, pyrethroids such as DDT, oxadiazines such as indoxacarb, acetylcholine-receptor agonists/antagonists, acetylcholine-receptor-modulators, nicotine, bensultap, cartap, chloronicotyinyls such as acetamiprid, bifenthrin, clothianidin, dinotefuran, imidac loprid, nitenpyram, nithiazine, thiacloprid, and thiamethoxam, spinosyns such as spinosad, cyclodiene organochlorines such as camphechlor, chlordane, endosulfan, gamma-HCH, HCH, heptachlor, lindane, methoxychlor, fiproles such as acetoprole, ethiprole, fipronil, vaniliprole, chloride-channel, 6.1 mectins such as avermectin, emamectin, emamectin-benzoate, ivermectin, and milbemycin, juvenile-hormone mimics such as diofenolan, epofenonane, fenoxycarb, hydroprene, kinoprene, methoprene, pyriproxyfen, and triprene, ecdysone agonists/disruptors, diacylhydrazine, chromafenozide, halofenozide, methoxyfenozide, tebufenozide, chitin biosynthesis inhibitors, benzoylureas such as bistrifluron, chlorfluazuron, diflubenzuron, fluazuron, flucycloxuron, flufenoxuron, hexaflumuron, lufenuron, novaluron, noviflumuron, penfluron, teflubenzuron, triflumuron, buprofezin, cyromazine, oxidative phosphorylation inhibitors, ATP disruptors, diafenthiuron, organotins such as azocyclotin, cyhexatin, fenbutatin-oxide, pyrroles such as chlorfenapyr, dinitrophenols such as binapacryl, dinobuton, dinocap, DNOC, site-I electron transport inhibitors, METI's such as fenazaquin, fenpyroximate, pyrimidifen, pyridaben, tebufenpyrad, tolfenpyrad, hydramethyinon, dicofol, rotenone, acequinocyl, fluacrypyrim, spirodiclofen, spiromesifen, tetramic acids, carboxamides such as flonicamid, octopaminergic agonists such as amitraz, magnesium-stimulated ATPase inhibitors such as propargite, BDCA's such as N2-[1,1-dimethyl-2-(methylsulfonyl)ethyl]-3-iodo-N1-[2-methyl-4-[1,2,2,2-tetrafluoro-1-(trifluoromethyl)ethyl]phenyl]-1,2-benzene, nereistoxin analogues such as thiocyclam hydrogen oxalate, and thiosultap sodium. Preferably the insecticide is one or more of chlorpyrifos and tefluthrin.

Nematicides that can be used in the various methods and compositions disclosed herein include, but are not limited to, acibenzolar-S-methyl, an avermectin (e.g., abamectin), carbamate nematicides (e.g., aldicarb, thiadicarb, carbofuran, carbosulfan, oxamyl, aldoxycarb, ethoprop, methomyl, benomyl, alanycarb), organophosphorus nematicides (e.g., phenamiphos (fenamiphos), fensulfothion, terbufos, fosthiazate, dimethoate, phosphocarb, dichlofenthion, isamidofos, fosthietan, isazofos ethoprophos, cadusafos, terbufos, chlorpyrifos, dichlofenthion, heterophos, isamidofos, mecarphon, phorate, thionazin, triazophos, diamidafos, fosthietan, phosphamidon), and certain fungicides, such as captan, thiophanate-methyl and thiabendazole.

Fungicides that can be used in the various methods and compositions disclosed herein include aliphatic nitrogen fungicides (butylamine, cymoxanil, dodicin, dodine, guazatine, iminoctadine); amide fungicides (benzovindiflupyr, carpropamid, chloraniformethan, cyflufenamid, diclocymet, diclocymet, dimoxystrobin, fenaminstrobin, fenoxanil, flumetover, furametpyr, isofetamid, isopyrazam, mandestrobin, mandipropamid, metominostrobin, orysastrobin, penthiopyrad, prochloraz, quinazamid, silthiofam, triforine); acylamino acid fungicides (benalaxyl, benalaxyl-M, furalaxyl, metalaxyl, metalaxyl-M, pefurazoate, valifenalate); anilide fungicides (benalaxyl, benalaxyl-M, bixafen, boscalid, carboxin, fenhexamid, fluxapyroxad, isotianil, metalaxyl, metalaxyl-M, metsulfovax, ofurace, oxadixyl, oxycarboxin, penflufen, pyracarbolid, sedaxane, thifluzamide, tiadinil, vanguard); benzanilide fungicides (benodanil, flutolanil, mebenil, mepronil, salicylanilide, tecloftalam); furanilide fungicides (fenfuram, furalaxyl, furcarbanil, methfuroxam); sulfonanilide fungicides (flusulfamide); benzamide fungicides (benzohydroxamic acid, fluopicolide, fluopyram, tioxymid, trichlamide, zarilamid, zoxamide); furamide fungicides (cyclafuramid, furmecyclox); phenylsulfamide fungicides (dichlofluanid, tolylfluanid); sulfonamide fungicides (amisulbrom, cyazofamid); valinamide fungicides (benthiavalicarb, iprovalicarb); antibiotic fungicides (aureofungin, blasticidin-S, cycloheximide, griseofulvin, kasugamycin, moroxydine, natamycin, polyoxins, polyoxorim, streptomycin, validamycin); strobilurin fungicides (fluoxastrobin, mandestrobin); methoxyacrylate strobilurin fungicides (azoxystrobin, bifujunzhi, coumoxystrobin, enoxastrobin, flufenoxystrobin, jiaxiangjunzhi, picoxystrobin, pyraoxystrobin); methoxycarbanilate strobilurin fungicides (pyraclostrobin, pyrametostrobin, triclopyricarb); methoxyiminoacetamide strobilurin fungicides (dimoxystrobin, fenaminstrobin, metominostrobin, orysastrobin); methoxyiminoacetate strobilurin fungicides (kresoxim-methyl, trifloxystrobin); aromatic fungicides (biphenyl, chlorodinitronaphthalenes, chloroneb, chlorothalonil, cresol, dicloran, fenjuntong, hexachlorobenzene, pentachlorophenol, quintozene, sodium pentachlorophenoxide, tecnazene, trichlorotrinitrobenzenes); arsenical fungicides (asomate, urbacide); aryl phenyl ketone fungicides (metrafenone, pyriofenone); benzimidazole fungicides (albendazole, benomyl, carbendazim, chlorfenazole, cypendazole, debacarb, fuberidazole, mecarbinzid, rabenzazole, thiabendazole); benzimidazole precursor fungicides (furophanate, thiophanate, thiophanate-methyl); benzothiazole fungicides (bentaluron, benthiavalicarb, benthiazole, chlobenthiazone, probenazole); botanical fungicides (allicin, berberine, carvacrol, carvone, osthol, sanguinarine, santonin); bridged diphenyl fungicides (bithionol, dichlorophen, diphenylamine, hexachlorophene, parinol); carbamate fungicides (benthiavalicarb, furophanate, iodocarb, iprovalicarb, picarbutrazox, propamocarb, pyribencarb, thiophanate, thiophanate-methyl, tolprocarb); benzimidazolylcarbamate fungicides (albendazole, benomyl, carbendazim, cypendazole, debacarb, mecarbinzid); carbanilate fungicides (diethofencarb, pyraclostrobin, pyrametostrobin, triclopyricarb); conazole fungicides, conazole fungicides (imidazoles) (climbazole, clotrimazole, imazalil, oxpoconazole, prochloraz, triflumizole); conazole fungicides (triazoles) (azaconazole, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole, uniconazole, uniconazole-P); copper fungicides (acypetacs-copper, Bordeaux mixture, Burgundy mixture, Cheshunt mixture, copper acetate, copper carbonate, basic, copper hydroxide, copper naphthenate, copper oleate, copper oxychloride, copper silicate, copper sulfate, copper sulfate, basic, copper zinc chromate, cufraneb, cuprobam, cuprous oxide, mancopper, oxine-copper, saisentong, thiodiazole-copper); cyanoacrylate fungicides (benzamacril, phenamacril); dicarboximide fungicides (famoxadone, fluoroimide); dichlorophenyl dicarboximide fungicides (chlozolinate, dichlozoline, iprodione, isovaledione, myclozolin, procymidone, vinclozolin); phthalimide fungicides (captafol, captan, ditalimfos, folpet, thiochlorfenphim); dinitrophenol fungicides (binapacryl, dinobuton, dinocap, dinocap-4, dinocap-6, meptyldinocap, dinocton, dinopenton, dinosulfon, dinoterbon, DNOC); dithiocarbamate fungicides (amobam, asomate, azithiram, carbamorph, cufraneb, cuprobam, disulfiram, ferbam, metam, nabam, tecoram, thiram, urbacide, ziram); cyclic dithiocarbamate fungicides (dazomet, etem, milneb); polymeric dithiocarbamate fungicides (mancopper, mancozeb, maneb, metiram, polycarbamate, propineb, zineb); dithiolane fungicides (isoprothiolane, saijunmao); fumigant fungicides (carbon disulfide, cyanogen, dithioether, methyl bromide, methyl iodide, sodium tetrathiocarbonate); hydrazide fungicides (benquinox, saijunmao); imidazole fungicides (cyazofamid, fenamidone, fenapanil, glyodin, iprodione, isovaledione, pefurazoate, triazoxide); conazole fungicides (imidazoles) (climbazole, clotrimazole, imazalil, oxpoconazole, prochloraz, triflumizole); inorganic fungicides (potassium azide, potassium thiocyanate, sodium azide, sulfur, see also copper fungicides, see also inorganic mercury fungicides); mercury fungicides; inorganic mercury fungicides (mercuric chloride, mercuric oxide, mercurous chloride); organomercury fungicides ((3-ethoxypropyl)mercury bromide, ethylmercury acetate, ethylmercury bromide, ethylmercury chloride, ethylmercury 2,3-dihydroxypropyl mercaptide, ethylmercury phosphate, N-(ethylmercury)-p-toluenesulphonanilide, hydrargaphen, 2-methoxyethylmercury chloride, methylmercury benzoate, methylmercury dicyandiamide, methylmercury pentachlorophenoxide, 8-phenylmercurioxyquinoline, phenylmercuriurea, phenylmercury acetate, phenylmercury chloride, phenylmercury derivative of pyrocatechol, phenylmercury nitrate, phenylmercury salicylate, thiomersal, tolylmercury acetate); morpholine fungicides (aldimorph, benzamorf, carbamorph, dimethomorph, dodemorph, fenpropimorph, flumorph, tridemorph); organophosphorus fungicides (ampropylfos, ditalimfos, EBP, edifenphos, fosetyl, hexylthiofos, inezin, iprobenfos, izopamfos, kejunlin, phosdiphen, pyrazophos, tolclofos-methyl, triamiphos); organotin fungicides (decafentin, fentin, tributyltin oxide); oxathiin fungicides (carboxin, oxycarboxin); oxazole fungicides (chlozolinate, dichlozoline, drazoxolon, famoxadone, hymexazol, metazoxolon, myclozolin, oxadixyl, oxathiapiprolin, pyrisoxazole, vinclozolin); polysulfide fungicides (barium polysulfide, calcium polysulfide, potassium polysulfide, sodium polysulfide); pyrazole fungicides (benzovindiflupyr, bixafen, fenpyrazamine, fluxapyroxad, furametpyr, isopyrazam, oxathiapiprolin, penflufen, penthiopyrad, pyraclostrobin, pyrametostrobin, pyraoxystrobin, rabenzazole, sedaxane); pyridine fungicides (boscalid, buthiobate, dipyrithione, fluazinam, fluopicolide, fluopyram, parinol, picarbutrazox, pyribencarb, pyridinitril, pyrifenox, pyrisoxazole, pyroxychlor, pyroxyfur, triclopyricarb); pyrimidine fungicides (bupirimate, diflumetorim, dimethirimol, ethirimol, fenarimol, ferimzone, nuarimol, triarimol); anilinopyrimidine fungicides (cyprodinil, mepanipyrim, pyrimethanil); pyrrole fungicides (dimetachlone, fenpiclonil, fludioxonil, fluoroimide); quaternary ammonium fungicides (berberine, sanguinarine); quinoline fungicides (ethoxyquin, halacrinate, 8-hydroxyquinoline sulfate, quinacetol, quinoxyfen, tebufloquin); quinone fungicides (chloranil, dichlone, dithianon); quinoxaline fungicides (chinomethionat, chlorquinox, thioquinox); thiadiazole fungicides (etridiazole, saisentong, thiodiazole-copper, zinc thiazole); thiazole fungicides (ethaboxam, isotianil, metsulfovax, octhilinone, oxathiapiprolin, thiabendazole, thifluzamide); thiazolidine fungicides (flutianil, thiadifluor); thiocarbamate fungicides (methasulfocarb, prothiocarb); thiophene fungicides (ethaboxam, isofetamid, silthiofam); triazine fungicides (anilazine); triazole fungicides (amisulbrom, bitertanol, fluotrimazole, triazbutil); conazole fungicides (triazoles) (azaconazole, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, huanjunzuo, imibenconazole, ipconazole, metconazole, myclobutanil, penconazole, propiconazole, prothioconazole, quinconazole, simeconazole, tebuconazole, tetraconazole, triadimefon, triadimenol, triticonazole, uniconazole, uniconazole-P); triazolopyrimidine fungicides (ametoctradin); urea fungicides (bentaluron, pencycuron, quinazamid); zinc fungicides (acypetacs-zinc, copper zinc chromate, cufraneb, mancozeb, metiram, polycarbamate, polyoxorim-zinc, propineb, zinc naphthenate, zinc thiazole, zinc trichlorophenoxide, zineb, ziram); unclassified fungicides (acibenzolar, acypetacs, allyl alcohol, benzalkonium chloride, bethoxazin, bromothalonil, chitosan, chloropicrin, DBCP, dehydroacetic acid, diclomezine, diethyl pyrocarbonate, ethylicin, fenaminosulf, fenitropan, fenpropidin, formaldehyde, furfural, hexachlorobutadiene, methyl isothiocyanate, nitrostyrene, nitrothal-isopropyl, OCH, pentachlorophenyl laurate, 2-phenylphenol, phthalide, piperalin, propamidine, proquinazid, pyroquilon, sodium orthophenylphenoxide, spiroxamine, sultropen, thicyofen, tricyclazole), or mefenoxam.

In some embodiments of the invention, a kit of parts is provided comprising a bacterial strain provided herein or active variant thereof, and/or a composition derived therefrom, and at least one biocide, in a spatially separated arrangement. In some embodiments, the biocide is an herbicide, fungicide, insecticide, pesticide, or other crop protection chemical.

Non-limiting embodiments of the invention include:
1. A composition comprising:
   (a) at least one of bacterial strain AIP045885, AIP075655, AIP09474, AIP024525, AIP033287, AIP093798, AIP061639, AIP082862, AIP058187, AIP059286, AIP036706, or an active variant of any thereof, wherein the active variant comprises a bacterial strain having a genome within a Mash distance of about 0.015, and wherein said bacterial strain or an active variant thereof is present at about $10^5$ CFU/gram to about $10^{12}$ CFU/gram or at about $10^5$ CFU/ml to about $10^{12}$ CFU/ml;
   (b) at least one of a spore, or a forespore, or a combination of cells, forespores, and/or spores from any of AIP045885, AIP075655, AIP09474, AIP024525, AIP033287, AIP093798, AIP061639, AIP082862, AIP058187, AIP059286, AIP036706, or an active variant of any thereof, wherein the active variant comprises a bacterial strain having a genome within a Mash distance of about 0.015, and wherein said spore, forespore, or a combination of cells, forespores, and/or spores or an active variant thereof is present at about $10^5$ CFU/gram to about $10^{12}$ CFU/gram or at about $10^5$ CFU/ml to about $10^{12}$ CFU/ml; and/or
   (c) a supernatant, filtrate, or extract derived from a whole cell culture of at least one of bacterial strain AIP045885, AIP075655, AIP09474, AIP024525, AIP033287, AIP093798, AIP061639, AIP082862, AIP058187, AIP059286, AIP036706, or an active variant of any thereof, wherein the active variant comprises a bacterial strain having a genome within a Mash distance of about 0.015.

2. The composition of embodiment 1, wherein said plant pest comprises a fungal pest.

3. The composition of embodiment 2, wherein said fungal pest comprises one or more fungal pathogens selected from the group consisting of *Aspergillus* spp., *Aspergillus flavus*, *Botrytis cinerea*, *Cersospora* spp, *Cercospora sojina*, *Cercospora beticola*, *Alternaria solani*, *Rhizoctonia solani*, *Blumeria graminis*, *Bremia lactucae*, *Erysiphe necator*, *Podosphaera* spp., *Podosphaera xanthii*, *Golovinomyces cichoracearum*, *Erysiphe lagerstroemiae*, *Sphaerotheca pannosa*, *Colletotrichm* spp., *Colletotrichum sublineolum*, *Colletotrichum cereale*, *Colletotrichum gloeosporiodes*, *Apiognomonia errabunda*, *Apiognomonia veneta*, *Discula fraxinea*, *Plasmopara viticola*, *Pseudoperonospora cubensis*, *Peronospora* spp., *Peronospora belbahrii*, *Peronospora lamii*, *Plasmopara obduscens*, *Pythium cryptoirregulare*, *Pythium aphanidermatum*, *Pythium irregulare*, *Pythium sylvaticum*, *Pythium myriotylum*, *Pythium ultimum*, *Phytophthora* spp., *Phytophthora capsici*, *Phytophthora nicotianae*, *Phytophthora infestans*, *Phytophthora tropicalis*, *Phytophthora sojae*, *Fusarium* spp., *Fusarium virguliforme*, *Fusarium graminearum*, *Fusarium solani*, *Fusarium oxysporum*, *Fusarium graminicola*, *Gibberella zeae*, *Colletotrichum graminicola*, *Phakopsora* spp., *Phakopsora meibomiae*, *Phakopsora pachyrizi*, *Puccinia triticina*, *Puccinia recondita*, *Puccinia striiformis*, *Puccinia graminis*, *Puccinia* spp., *Venturia inaequalis*, *Verticillium* spp, *Mycosphaerella* spp., *Mycosphaerella fijiensis*, *Monilinia fructicola*, *Monilinia lax*, and *Monilinia fructigena*.

4. The composition of embodiment 1, wherein said pest is an insect pest.

5. The composition of embodiment 4, wherein said insect pest is a coleopteran, lepidopteran, or hemipteran insect.

6. The composition of any of embodiments 1-5, wherein said cell, spore, forespore, or combination of cells, spores and/or forespores or the active variant of any thereof is present at about $10^5$ CFU/gram to about $10^{10}$ CFU/gram or at about $10^5$ CFU/ml to about $10^{10}$ CFU/ml.

7. The composition of any of embodiments 1-6, wherein said composition comprises a cell paste.

8. The composition of any one of embodiments 1-7, wherein said composition comprises a wettable powder.

9. A composition comprising a cell paste comprising a cell, a spore, a forespore, or a combination of cells, spores and/or forespores of at least one of bacterial strain AIP045885, AIP075655, AIP09474, AIP024525, AIP033287, AIP093798, AIP061639, AIP082862, AIP058187, AIP059286, AIP036706, or an active variant of any thereof, wherein the active variant comprises a cell, spore, forespore, or a combination of cells, spores and/or forespores having a genome within a Mash distance of about 0.015;
   wherein an effective amount of said composition controls a plant pest or improves an agronomic trait of interest of a plant.

10. The composition of embodiment 9, wherein said plant pest comprises a fungal pest.

11. The composition of embodiment 10, wherein said fungal pest comprises one or more fungal pathogens selected from the group consisting of *Aspergillus* spp., *Aspergillus flavus*, *Botrytis cinerea*, *Cersospora* spp, *Cercospora sojina*, *Cercospora beticola*, *Alternaria solani*, *Rhizoctonia solani*, *Blumeria graminis*, *Bremia lactucae*, *Erysiphe necator*, *Podosphaera* spp., *Podosphaera xanthii*, *Golovinomyces cichoracearum*, *Erysiphe lagerstroemiae*, *Sphaerotheca pannosa*, *Colletotrichm* spp., *Colletotrichum sublineolum*, *Colletotrichum cereale*, *Colletotrichum gloeosporiodes*, *Apiognomonia errabunda*, *Apiognomonia veneta*, *Discula fraxinea*, *Plasmopara viticola*, *Pseudoperonospora cubensis*, *Peronospora* spp., *Peronospora belbahrii*, *Peronospora lamii*, *Plasmopara obduscens*, *Pythium cryptoirregulare*, *Pythium aphanidermatum*, *Pythium irregulare*, *Pythium sylvaticum*, *Pythium myriotylum*, *Pythium ultimum*, *Phytophthora* spp., *Phytophthora capsici*, *Phytophthora nicotianae*, *Phytophthora infestans*, *Phytophthora tropicalis*, *Phytophthora sojae*, *Fusarium* spp., *Fusarium virguliforme*, *Fusarium graminearum*, *Fusarium solani*, *Fusarium oxysporum*, *Fusarium graminicola*, *Gibberella zeae*, *Colletotrichum graminicola*, *Phakopsora* spp., *Phakopsora meibomiae*, *Phakopsora pachyrizi*, *Puccinia triticina*, *Puccinia recondita*, *Puccinia striiformis*, *Puccinia graminis*, *Puccinia* spp., *Venturia inaequalis*, *Verticillium* spp, *Mycosphaerella* spp., *Mycosphaerella fijiensis*, *Monilinia fructicola*, *Monilinia lax*, and *Monilinia fructigena*.

12. The composition of embodiment 9, wherein said plant pest is an insect pest.

13. The composition of embodiment 12, wherein said insect pest is a coleopteran, lepidopteran, or hemipteran insect.

14. A composition comprising a wettable power comprising:
   (a) at least one of bacterial strain AIP045885, AIP075655, AIP09474, AIP024525, AIP033287, AIP093798, AIP061639, AIP082862, AIP058187, AIP059286, AIP036706, or an active variant of any thereof, wherein the active variant comprises a bacterial strain having a genome within a Mash distance of about 0.015, and wherein said bacterial strain or an active variant thereof is present at about $10^5$ CFU/gram to about $10^{12}$ CFU/gram or at about $10^5$ CFU/ml to about $10^{12}$ CFU/ml;
   (b) at least one of a spore, or a forespore, or a combination of cells, forespores, and/or spores from any of AIP045885, AIP075655, AIP09474, AIP024525, AIP033287, AIP093798, AIP061639, AIP082862, AIP058187, AIP059286, AIP036706, or an active variant of any thereof, wherein the active variant comprises a bacterial strain having a genome within a Mash distance of about 0.015, and wherein said spore, forespore, or a combination of cells, forespores, and/or spores or an active variant thereof is present at about $10^5$ CFU/gram to about $10^{12}$ CFU/gram or at about $10^5$ CFU/ml to about $10^{12}$ CFU/ml; and/or
   (c) a supernatant, filtrate, or extract derived from a whole cell culture of at least one of bacterial strain AIP045885, AIP075655, AIP09474, AIP024525, AIP033287, AIP093798, AIP061639, AIP082862, AIP058187, AIP059286, AIP036706, or an active variant of any thereof, wherein the active variant comprises a bacterial strain having a genome within a Mash distance of about 0.015;
   wherein an effective amount of said composition controls a plant pest or improves an agronomic trait of interest of a plant.

15. The composition of embodiment 14, wherein said plant pest comprises at least one fungal pest.

16. The composition of embodiment 15, wherein said fungal pest comprises one or more fungal pathogens selected from the group consisting of *Aspergillus* spp., *Aspergillus flavus, Botrytis cinerea, Cersospora* spp, *Cercospora sojina, Cercospora beticola, Alternaria solani, Rhizoctonia solani, Blumeria graminis, Bremia lactucae, Erysiphe necator, Podosphaera* spp., *Podosphaera xanthii, Golovinomyces cichoracearum, Erysiphe lagerstroemiae, Sphaerotheca pannosa, Colletotrichm* spp., *Colletotrichum sublineolum, Colletotrichum cereale, Colletotrichum gloeosporiodes, Apiognomonia errabunda, Apiognomonia veneta, Discula fraxinea, Plasmopara viticola, Pseudoperonospora cubensis, Peronospora* spp., *Peronospora belbahrii, Peronospora lamii, Plasmopara obduscens, Pythium cryptoirregulare, Pythium aphanidermatum, Pythium irregulare, Pythium sylvaticum, Pythium myriotylum, Pythium ultimum, Phytophthora* spp., *Phytophthora capsici, Phytophthora nicotianae, Phytophthora infestans, Phytophthora tropicalis, Phytophthora sojae, Fusarium* spp., *Fusarium virguliforme, Fusarium graminearum, Fusarium solani, Fusarium oxysporum, Fusarium graminicola, Gibberella zeae, Colletotrichum graminicola, Phakopsora* spp., *Phakopsora meibomiae, Phakopsora pachyrizi, Puccinia triticina, Puccinia recondita, Puccinia striiformis, Puccinia graminis, Puccinia* spp., *Venturia inaequalis, Verticillium* spp, *Mycosphaerella* spp., *Mycosphaerella fijiensis, Monilinia fructicola, Monilinia lax*, and *Monilinia fructigena*.

17. The composition of embodiment 14, wherein said plant plest comprises at least one insect pest.

18. The composition of embodiment 16, wherein said insect pest is a coleopteran, lepidopteran, and/or hemipteran insect.

19. The composition of any one of embodiments 14-18, wherein said active variant is resistant to at least one herbicide, nematicide, fungicide, pesticide, insecticide or other crop protection chemical.

20. The composition of embodiment 19, wherein said active variant is selected under herbicide, fungicide, pesticide, insecticide, or other crop protection chemical pressure and is resistant to said herbicide, fungicide, pesticide, insecticide, or other crop protection chemical.

21. The composition of any one of embodiments 14-20, wherein said active variant has been transformed with a herbicide resistance gene rendering the cell, spore, forespore, or combination of cells, forespores and/or spores herbicide resistant.

22. The composition of embodiment 21, wherein said herbicide is selected from the group consisting of glyphosate, glufosinate (glutamine synthase inhibitor), sulfonylurea and imidazolinone herbicides (branched chain amino acid synthesis inhibitors).

23. An isolated biologically pure culture of a bacterial strain comprising a cell, a spore, a forespore, or a combination of cells, spores and/or forespores of AIP045885, AIP075655, AIP09474, AIP024525, AIP033287, AIP093798, AIP061639, AIP082862, AIP058187, AIP059286, AIP036706, or an active variant of any thereof, wherein the active variant comprises a cell, spore, forespore, or combination of cells, spores and/or forespores having a genome within a Mash distance of about 0.015;
  wherein an effective amount of said cell, spore, forespore, or combination of cells, spores and/or forespores controls a plant pest or improves an agronomic trait of interest of a plant.

24. The isolated biologically pure culture of embodiment 23, wherein said bacterial strain is resistant to a biocide selected from a herbicide, a fungicide, a pesticide, insecticide, or a crop protection chemical, wherein said culture is produced by growing in the presence of said biocide.

25. The isolated biologically pure culture of embodiment 24, wherein said biologically pure culture is able to grow in the presence of glyphosate.

26. The isolated biologically pure culture of any one of embodiments 23-25, wherein said plant pest comprises a fungal pest.

27. The isolated biologically pure culture of embodiment 26, wherein said fungal pest comprises one or more fungal pathogens selected from the group consisting of *Aspergillus* spp., *Aspergillus flavus, Botrytis cinerea, Cersospora* spp, *Cercospora sojina, Cercospora beticola, Alternaria solani, Rhizoctonia solani, Blumeria graminis, Bremia lactucae, Erysiphe necator, Podosphaera* spp., *Podosphaera xanthii, Golovinomyces cichoracearum, Erysiphe lagerstroemiae, Sphaerotheca pannosa, Colletotrichm* spp., *Colletotrichum sublineolum, Colletotrichum cereale, Colletotrichum gloeosporiodes, Apiognomonia errabunda, Apiognomonia veneta, Discula fraxinea, Plasmopara viticola, Pseudoperonospora cubensis, Peronospora* spp., *Peronospora belbahrii, Peronospora lamii, Plasmopara obduscens, Pythium cryptoirregulare, Pythium aphanidermatum, Pythium irregulare, Pythium sylvaticum, Pythium myriotylum, Pythium ultimum, Phytophthora* spp., *Phytophthora capsici, Phytophthora nicotianae, Phytophthora infestans, Phytophthora tropicalis, Phytophthora sojae, Fusarium* spp., *Fusarium virguliforme, Fusarium graminearum, Fusarium solani, Fusarium oxysporum, Fusarium graminicola, Gibberella zeae, Colletotrichum graminicola, Phakopsora* spp., *Phakopsora meibomiae, Phakopsora pachyrizi, Puccinia triticina, Puccinia recondita, Puccinia striiformis, Puccinia graminis, Puccinia* spp., *Venturia inaequalis, Verticillium* spp, *Mycosphaerella* spp., *Mycosphaerella fijiensis, Monilinia fructicola, Monilinia lax*, and *Monilinia fructigena*.

28. The isolated biologically pure culture of any one of embodiments 23-25, wherein said plant pest comprises at least one insect pest.

29. The isolated biologically pure culture of embodiment 28, wherein said insect pest is a coleopteran, lepidopteran, and/or hemipteran insect.

30. A bacterial culture grown from a cell, a spore, a forespore, or a combination of cells, spores and/or forespores of AIP045885, AIP075655, AIP09474, AIP024525, AIP033287, AIP093798, AIP061639, AIP082862, AIP058187, AIP059286, AIP036706, or an active variant of any thereof, wherein the active variant comprises a cell, spore, forespore, or a combination of cells, spores and/or forespores having a genome within a Mash distance of about 0.015;
  wherein said bacterial culture is able to grow in the presence of glufosinate; and
  wherein an effective amount of said bacterial culture controls a plant pest or improves an agronomic trait of interest of a plant.

31. The bacterial culture of embodiment 30, wherein said plant pest comprises a fungal pest.

32. The bacterial culture of embodiment 31, wherein said fungal pest comprises one or more fungal pathogens selected from the group consisting of *Aspergillus* spp., *Aspergillus flavus, Botrytis cinerea, Cersospora* spp, *Cercospora sojina, Cercospora beticola, Alternaria solani, Rhizoctonia solani, Blumeria graminis, Bremia lactucae, Erysiphe necator, Podosphaera* spp., *Podosphaera xanthii, Golovinomyces cichoracearum, Erysiphe lagerstroemiae, Sphaerotheca*

*pannosa, Colletotrichm* spp., *Colletotrichum sublineolum, Colletotrichum cereale, Colletotrichum gloeosporiodes, Apiognomonia errabunda, Apiognomonia veneta, Discula fraxinea, Plasmopara viticola, Pseudoperonospora cubensis, Peronospora* spp., *Peronospora belbahrii, Peronospora lamii, Plasmopara obduscens, Pythium cryptoirregulare, Pythium aphanidermatum, Pythium irregulare, Pythium sylvaticum, Pythium myriotylum, Pythium ultimum, Phytophthora* spp., *Phytophthora capsici, Phytophthora nicotianae, Phytophthora infestans, Phytophthora tropicalis, Phytophthora sojae, Fusarium* spp., *Fusarium virguliforme, Fusarium graminearum, Fusarium solani, Fusarium oxysporum, Fusarium graminicola, Gibberella zeae, Colletotrichum graminicola, Phakopsora* spp., *Phakopsora meibomiae, Phakopsora pachyrizi, Puccinia triticina, Puccinia recondita, Puccinia striiformis, Puccinia graminis, Puccinia* spp., *Venturia inaequalis, Verticillium* spp, *Mycosphaerella* spp., *Mycosphaerella fijiensis, Monilinia fructicola, Monilinia lax,* and *Monilinia fructigena.*

33. The bacterial culture of embodiment 30, wherein said plant pest is an insect pest.

34. The bacterial culture of embodiment 33, wherein said insect pest is a coleopteran, lepidopteran, and/or hemipteran insect.

35. A method for controlling a plant pest population comprising contacting said population with an effective amount of the composition of any one of embodiments 1-22, the isolated biologically pure culture of any one of embodiments 23-29, or the bacterial culture of any one of embodiments 30-34, wherein said bacterial strain controls said plant pest.

36. A method for growing a plant susceptible to a plant pest or plant disease caused by a plant pest or improving an agronomic trait of interest in a plant comprising applying to the plant:
  (a) an effective amount of at least one of bacterial strain AIP045885, AIP075655, AIP09474, AIP024525, AIP033287, AIP093798, AIP061639, AIP082862, AIP058187, AIP059286, AIP036706, or an active variant of any thereof wherein the active variant comprises a bacterial strain having a genome within a Mash distance of about 0.015, wherein said effective amount comprises at least about $10^{12}$ to $10^{16}$ colony forming units (CFU) per hectare;
  (b) an effective amount of at least one of a spore, or a forespore, or a combination of cells, forespores and/or spores from any one of AIP045885, AIP075655, AIP09474, AIP024525, AIP033287, AIP093798, AIP061639, AIP082862, AIP058187, AIP059286, AIP036706 or an active variant of any thereof, wherein the active variant comprises a bacterial strain having a genome within a Mash distance of about 0.015, wherein said effective amount comprises at least about $10^{12}$ to $10^{16}$ colony forming units (CFU) per hectare; and/or,
  (c) an effective amount of a supernatant, filtrate, or extract derived from a whole cell culture of at least one of bacterial strain AIP045885, AIP075655, AIP09474, AIP024525, AIP033287, AIP093798, AIP061639, AIP082862, AIP058187, AIP059286, AIP036706, or an active variant of any thereof, wherein the active variant comprises a bacterial strain having a genome within a Mash distance of about 0.015;
  wherein said effective amount controls said plant pest or improves the agronomic trait of interest.

37. The method of embodiment 36, wherein said method increases yield of the plant susceptible to the plant pest.

38. The method of embodiment 36 or 37, wherein said plant is a soybean.

39. The method of any one of embodiments 36-38, wherein said plant pest comprises a fungal pest.

40. The method of embodiment 39, wherein said fungal pest comprises one or more fungal pathogens selected from the group consisting of *Aspergillus* spp., *Aspergillus flavus, Botrytis cinerea, Cersospora* spp, *Cercospora sojina, Cercospora beticola, Alternaria solani, Rhizoctonia solani, Blumeria graminis, Bremia lactucae, Erysiphe necator, Podosphaera* spp., *Podosphaera xanthii, Golovinomyces cichoracearum, Erysiphe lagerstroemiae, Sphaerotheca pannosa, Colletotrichm* spp., *Colletotrichum sublineolum, Colletotrichum cereale, Colletotrichum gloeosporiodes, Apiognomonia errabunda, Apiognomonia veneta, Discula fraxinea, Plasmopara viticola, Pseudoperonospora cubensis, Peronospora* spp., *Peronospora belbahrii, Peronospora lamii, Plasmopara obduscens, Pythium cryptoirregulare, Pythium aphanidermatum, Pythium irregulare, Pythium sylvaticum, Pythium myriotylum, Pythium ultimum, Phytophthora* spp., *Phytophthora capsici, Phytophthora nicotianae, Phytophthora infestans, Phytophthora tropicalis, Phytophthora sojae, Fusarium* spp., *Fusarium virguliforme, Fusarium graminearum, Fusarium solani, Fusarium oxysporum, Fusarium graminicola, Gibberella zeae, Colletotrichum graminicola, Phakopsora* spp., *Phakopsora meibomiae, Phakopsora pachyrizi, Puccinia triticina, Puccinia recondita, Puccinia striiformis, Puccinia graminis, Puccinia* spp., *Venturia inaequalis, Verticillium* spp, *Mycosphaerella* spp., *Mycosphaerella fijiensis, Monilinia fructicola, Monilinia lax,* and *Monilinia fructigena.*

41. The method of any one of embodiments 36-38, wherein said plant pest is an insect pest.

42. The method of embodiment 41, wherein said insect pest is a coleopteran, lepidopteran, and/or hemipteran insect.

43. A method of controlling a plant pest in an area of cultivation comprising:
  (a) planting the area of cultivation with seeds or plants susceptible to the plant pest; and
  (b) applying to the seed or plant susceptible to the plant pest:
    (i) an effective amount of at least one bacterial strain comprising AIP045885, AIP075655, AIP09474, AIP024525, AIP033287, AIP093798, AIP061639, AIP082862, AIP058187, AIP059286, AIP036706, or an active variant of any thereof, wherein the active variant comprises a bacterial strain having a genome within a Mash distance of about 0.015, and wherein said effective amount comprises at least about $10^{12}$ to $10^{16}$ colony forming units (CFU) per hectare;
    (ii) an effective amount of at least one bacterial strain comprising a spore, or a forespore, or a combination of cells, forespores and/or spores from any one of AIP045885, AIP075655, AIP09474, AIP024525, AIP033287, AIP093798, AIP061639, AIP082862, AIP058187, AIP059286, AIP036706, or an active variant of any thereof, wherein the active variant comprises a bacterial strain having a genome within a Mash distance of about 0.015, and wherein said effective amount comprises at least about $10^{12}$ to $10^{16}$ colony forming units (CFU) per hectare; or
    (iii) an effective amount of a supernatant, filtrate, or extract derived from a whole cell culture of at least one of bacterial strain AIP045885, AIP075655, AIP09474, AIP024525, AIP033287, AIP093798, AIP061639, AIP082862, AIP058187, AIP059286, AIP036706, or an active variant of any thereof, wherein the active variant comprises a bacterial strain having a genome within a Mash distance of about 0.015;

wherein said effective amount controls a plat pest in an area of cultivation.

44. The method of embodiment 43, where said seed or plant is a soybean.

45. The method of embodiment 43 or 44, wherein said plant pest comprises a fungal pest.

46. The method of embodiment 45, wherein said fungal pest comprises one or more fungal pathogens selected from the group consisting of *Aspergillus* spp., *Aspergillus flavus*, *Botrytis cinerea, Cersospora* spp, *Cercospora sojina, Cercospora beticola, Alternaria solani, Rhizoctonia solani, Blumeria graminis, Bremia lactucae, Erysiphe necator, Podosphaera* spp., *Podosphaera xanthii, Golovinomyces cichoracearum, Erysiphe lagerstroemiae, Sphaerotheca pannosa, Colletotrichm* spp., *Colletotrichum sublineolum, Colletotrichum cereale, Colletotrichum gloeosporiodes, Apiognomonia errabunda, Apiognomonia veneta, Discula fraxinea, Plasmopara viticola, Pseudoperonospora cubensis, Peronospora* spp., *Peronospora belbahrii, Peronospora lamii, Plasmopara obduscens, Pythium cryptoirregulare, Pythium aphanidermatum, Pythium irregulare, Pythium sylvaticum, Pythium myriotylum, Pythium ultimum, Phytophthora* spp., *Phytophthora capsici, Phytophthora nicotianae, Phytophthora infestans, Phytophthora tropicalis, Phytophthora sojae, Fusarium* spp., *Fusarium virguliforme, Fusarium graminearum, Fusarium solani, Fusarium oxysporum, Fusarium graminicola, Gibberella zeae, Colletotrichum graminicola, Phakopsora* spp., *Phakopsora meibomiae, Phakopsora pachyrizi, Puccinia triticina, Puccinia recondita, Puccinia striiformis, Puccinia graminis, Puccinia* spp., *Venturia inaequalis, Verticillium* spp, *Mycosphaerella* spp., *Mycosphaerella fijiensis, Monilinia fructicola, Monilinia lax,* and *Monilinia fructigena.*

47. The method of embodiment 43 or 44, wherein the plant pest is an insect pest.

48. The method of embodiment 46, wherein the insect pest is a coleopteran, lepidopteran, and/or hemipteran insect.

49. The method of any one of embodiments 43-48, wherein said method further comprises applying an effective amount of a biocide, wherein said effective amount of the biocide selectively controls an organism of interest while not significantly damaging said seed or plant.

50. The method of embodiment 49, wherein said cell, spore, forespore, or combination of cells, spores and/or forespores or active variant of any thereof and the biocide are applied simultaneously.

51. The method of embodiment 49, wherein said cell, spore, forespore, or combination of cells, spores and/or forespores or active variant of any thereof and the biocide are applied sequentially.

52. The method of any one of embodiments 49-51 where the biocide is a nematicide.

53. A method of making a modified bacterial strain comprising:
(a) providing a population of a cell, a spore, a forespore, or a combination of cells, spores and/or forespores of at least one bacterial strain comprising AIP045885, AIP075655, AIP09474, AIP024525, AIP033287, AIP093798, AIP061639, AIP082862, AIP058187, AIP059286, AIP036706, or an active variant of any thereof, wherein the active variant comprises a cell, spore, forespore, or a combination of cells, spores and/or forespores having a genome within a Mash distance of about 0.015, wherein said population is susceptible to a biocide of interest;
(b) culturing said population in the presence of a biocide of interest; and,
(c) selecting a modified bacterial strain having an increased resistance to said biocide of interest.

54. The method of embodiment 53, where said culturing comprises increasing the concentration of the biocide over time.

55. The method of embodiment 53 or 54, where said biocide is glyphosate or glufosinate.

56. A method of treating or preventing a plant disease or damage caused by a plant pest comprising applying to a plant having said plant pest, said plant disease, said damage, susceptible to said plant pest, or at risk of developing said plant disease or damage:

(a) at least one of bacterial strain AIP045885, AIP075655, AIP09474, AIP024525, AIP033287, AIP093798, AIP061639, AIP082862, AIP058187, AIP059286, AIP036706 or an active variant of any thereof, wherein the active variant comprises a bacterial strain having a genome within a Mash distance of about 0.015, wherein said effective amount comprises at least about $10^{12}$ to $10^{16}$ CFU per hectare;

(b) at least one of a spore or a forespore, or a combination of cells, forespores and/or spores from any one of AIP045885, AIP075655, AIP09474, AIP024525, AIP033287, AIP093798, AIP061639, AIP082862, AIP058187, AIP059286, AIP036706 or an active variant of any thereof, wherein the active variant comprises a bacterial strain having a genome within a Mash distance of about 0.015, wherein said effective amount comprises at least about $10^{12}$ to $10^{16}$ CFU per hectare; and/or (c) an effective amount of a supernatant, filtrate, or extract derived from a whole cell culture of at least one of bacterial strain AIP045885, AIP075655, AIP09474, AIP024525, AIP033287, AIP093798, AIP061639, AIP082862, AIP058187, AIP059286, AIP036706, or an active variant of any thereof, wherein the active variant comprises a bacterial strain having a genome within a Mash distance of about 0.015;

wherein the effective amount controls the plant pest that causes the plant disease.

57. The method of embodiment 56, wherein said plant is a soybean.

58. The method of embodiment 56 or 57, wherein said bacterial strain or active variant thereof treats or prevents one or more plant diseases.

59. The method of embodiment 58, wherein said one or more plant diseases are caused by a fungal pest.

60. The method of embodiment 59, wherein said fungal pest comprises one or more fungal pathogens selected from the group consisting of *Aspergillus* spp., *Aspergillus flavus, Botrytis cinerea, Cersospora* spp, *Cercospora sojina, Cercospora beticola, Alternaria solani, Rhizoctonia solani,*

*Blumeria graminis, Bremia lactucae, Erysiphe necator, Podosphaera* spp., *Podosphaera xanthii, Golovinomyces cichoracearum, Erysiphe lagerstroemiae, Sphaerotheca pannosa, Colletotrichm* spp., *Colletotrichum sublineolum, Colletotrichum cereale, Colletotrichum gloeosporiodes, Apiognomonia errabunda, Apiognomonia veneta, Discula fraxinea, Plasmopara viticola, Pseudoperonospora cubensis, Peronospora* spp., *Peronospora belbahrii, Peronospora lamii, Plasmopara obduscens, Pythium cryptoirregulare, Pythium aphanidermatum, Pythium irregulare, Pythium sylvaticum, Pythium myriotylum, Pythium ultimum, Phytophthora* spp., *Phytophthora capsici, Phytophthora nicotianae, Phytophthora infestans, Phytophthora tropicalis, Phytophthora sojae, Fusarium* spp., *Fusarium virguliforme, Fusarium graminearum, Fusarium solani, Fusarium oxysporum, Fusarium graminicola, Gibberella zeae, Colletotrichum graminicola, Phakopsora* spp., *Phakopsora meibomiae, Phakopsora pachyrizi, Puccinia triticina, Puccinia recondita, Puccinia striiformis, Puccinia graminis, Puccinia* spp., *Venturia inaequalis, Verticillium* spp, *Mycosphaerella* spp., *Mycosphaerella fijiensis, Monilinia fructicola, Monilinia lax*, and *Monilinia fructigena*.

61. The method of embodiment 58, wherein said one or plant diseases are caused by an insect pest.

62. The method of embodiment 61, wherein said insect pest is a coleopteran, lepidopteran, and/or hemipteran insect.

63. A kit of parts comprising a biocide and at least one of the following:

(a) at least one of bacterial strain AIP045885, AIP075655, AIP09474, AIP024525, AIP033287, AIP093798, AIP061639, AIP082862, AIP058187, AIP059286, AIP036706 or an active variant of any thereof, wherein the active variant comprises a bacterial strain having a genome within a Mash distance of about 0.015, (b) at least one of a spore or a forespore, or a combination of cells, forespores and/or spores from any one of AIP045885, AIP075655, AIP09474, AIP024525, AIP033287, AIP093798, AIP061639, AIP082862, AIP058187, AIP059286, AIP036706 or an active variant of any thereof, wherein the active variant comprises a bacterial strain having a genome within a Mash distance of about 0.015; and/or (c) a supernatant, filtrate, or extract derived from a whole cell culture of at least one of bacterial strain AIP045885, AIP075655, AIP09474, AIP024525, AIP033287, AIP093798, AIP061639, AIP082862, AIP058187, AIP059286, AIP036706, or an active variant of any thereof, wherein the active variant comprises a bacterial strain having a genome within a Mash distance of about 0.015.

64. The kit of embodiment 63, wherein the biocide is an herbicide, fungicide, insecticide, nematicide, or pesticide.

The following examples are offered by way of illustration and not by way of limitation.

EXAMPLES

Example 1. Microbial Strains and Methods of Culturing

TABLE 2

Bacterial strains selected for evaluation of inhibition of pest activity

| Strain ID | NRRL No. | Date of deposit | Taxonomic ID Genus | Nearest 16S Neighbor |
|---|---|---|---|---|
| AIP045885 | B-67650 | Aug. 3, 2018 | *Pseudomonas* | *chlororaphis* |
| AIP075655 | B-67651 | Aug. 3, 2018 | *Pseudomonas* | *chlororaphis* |
| AIP009474 | B-67657 | Aug. 3, 2018 | *Bacillus* | *subtilis* |
| AIP024525 | B-67661 | Aug. 3, 2018 | *Bacillus* | *thuringiensis* |
| AIP033287 | B-67659 | Aug. 3, 2018 | *Bacillus* | *subtilis* |
| AIP093798 | B-67660 | Aug. 3, 2018 | *Bacillus* | *subtilis* |
| AIP061639 | B-67654 | Aug. 3, 2018 | *Pseudomonas* | *chlororaphis* |
| AIP082862 | B-67656 | Aug. 3, 2018 | *Pseudomonas* | *chlororaphis* |
| AIP058187 | B-67655 | Aug. 3, 2018 | *Pseudomonas* | *chlororaphis* |
| AIP059286 | B-67653 | Aug. 3, 2018 | *Pseudomonas* | *chlororaphis* |
| AIP036706 | B-67652 | Aug. 3, 2018 | *Pseudomonas* | *chlororaphis* |

The bacterial strains set forth in Table 2 were cultured in medium. Table 3A summarizes the incubation time and the concentration of bacteria (CFU/ml) achieved. Table 3B provides the media recipe.

TABLE 3A

Culture conditions

| Strain ID | Incubation time (hrs) | Concentration (CFU/ml) |
|---|---|---|
| AIP045885 | 72 | 2.11E+10 |
| AIP075655 | 72 | 4.46E+10 |
| AIP009474 | 72 | 3.62E+08 |
| AIP061382 | 72 | 1.57E+10 |
| AIP029105 | 72 | 4.90E+09 |
| AIP024525 | 72 | 3.47E+09 |
| AIP033287 | 72 | 7.40E+08 |
| AIP093798 | 72 | 4.27E+09 |
| AIP061639 | 72 | 2.63E+10 |
| AIP082862 | 72 | 1.69E+10 |
| AIP058187 | 73 | 2.48E+10 |
| AIP059286 | 73 | 3.12E+10 |
| AIP036706 | 72 | 2.22E+10 |

TABLE 3B

Media recipe

| Ingredient | Amount (g/L) |
|---|---|
| Sodium Phosphate Dibasic Heptahydrate | 11.33 |
| Potassium Phosphate Monobasic | 3 |
| Ammonium Chloride | 1.55 |
| L(+)-Monosodium glutamate | 14.01 |
| Magnesium Sulfate Heptahdyrate | 0.5 |
| Amberex Yeast Extract | 10 |
| Zinc Sulfate | 0.05 |
| Iron (II) Sulfate Heptahydrate | 0.004 |
| Dextrose | 75 |

Example 2: Evaluation of Bacterial Strains Against Asian Soybean Rust

Plant material: The susceptible soybean cultivar Williams 82 was used in strain evaluation using the detached-leaf technique (Twizeyimana and Hartman, 2010) and using whole plant in growth chambers. Briefly, soybean seeds were sown in 18-cell plastic inserts that were filled with soil-less mix (Sunshine Mix, LC1; Sun Gro Horticulture Inc. Bellevue, WA) and placed inside a flat, Cells were fertilized at planting with slow-release pellets (Osmocote 19-6-12; 2 pellets per $cm^2$), Flats were maintained inside a growth chamber (Percival Scientific, Inc., Boone, IA) maintained at 70% relative humidity (RH) with a daily cycle of 14 h of light and 10 h of darkness at 24° and 20° C., respectively.

Bacterial strains: The bacterial strains set forth in Table 2 were plated on Luria Bertani medium or in liquid culture, CHA medium which consists of, per L, NaCl (5 g), tryptone (10 g), nutrient broth (8 g), $CaCl_2$ (0.14 mM), $MgCl_2 \cdot 6H_2O$ (0.2 mM), and $MnCl_2 \cdot 4\ H_2O$ (0.01 mM) and were purified to obtain single colonies. Single colonies were characterized morphologically or using molecular techniques.

*Phakopsora pachyrhizi* isolate: The isolate FL07-1 was used in all inoculations. The isolate was a single spore isolate obtained from infected soybean leaves collected from Gadseden County, Florida in 2007.

Strain Evaluation:

Evaluation on detached-leaf Briefly, leaf disks (3-cm diameter each) were sprayed with 120 µl of the bacterial strain ($1\times10^8$ spores/ml of water) of *P. pachyrhizi*. Leaf disks were inoculated with 120 µl spore suspension ($1\times10^4$ spores/ml of sterile distilled water) of *P. pachyrhizi* a day after application of the bacterial strain. Both the bacterial strain and *P. pachyrhizi* inoculation applications were done using an atomizer attached to an air compressor (Twizeyimana and Hartman, 2010). Leaf disks were placed adaxial side down on saturated 20×20 cm filter paper (Whatman International Ltd., Kent, England) in a plastic container (Blister Box 20×20 cm, Placon, Madison, WI); two filter papers were used per box. Boxes with leaf disks were incubated in the dark for a period of 12 h followed by a cycle of 13 hours of light (380 umol m-2s-1) and 11 h of darkness inside a tissue chamber (Percival Scientific, Inc.) maintained at 23° C. and 95% RH. Prior to incubation, boxes were placed inside zip bags (Webster Industries, Peabody, MA). The experimental design was a randomized complete block design with 2 replications and was repeated once.

Evaluation on whole plant: Bacterial strains were selected from the initial screening (conducted using leaf disk) based on their uredinia counts and were evaluated on whole plant in growth chambers. In this evaluation, when plants were at V2-stage (Fehr et al. 1971), the first fully expanded trifoliate leaf was sprayed with the bacterial strain, and the inoculation with *P. pachyrhizi* was done a day after as described in detached-leaf evaluation. Sprayed plants were maintained in a growth chamber at 75% RH with a daily cycle of 14 h and 10 h of light and darkness at 22° C. and 24° C., respectively. The experimental design was a randomized complete block design with 3 replications and was repeated once.

Data collection and results: In both evaluations, data recorded was numbers of uredinia (uredinia counts) in 1-cm diameter circle recorded 14 days after inoculation. Nine bacterial strains that have <10 uredinia in 1-cm diameter circle were selected after evaluation on whole plant in growth chamber to be tested in the field.

TABLE 4

| Activity of bacterial strains against *Phakopsora pachyrhizi* | |
|---|---|
| Strain ID | Disease control (%) |
| AIP045885 | Not tested |
| AIP075655 | 96.4 |
| AIP009474 | 100 |
| AIP024525 | 63.5 |
| AIP033287 | 86.6 |
| AIP093798 | 97.2 |
| AIP061639 | 39.2 |
| AIP082862 | 74.9 |
| AIP058187 | 57.2 |
| AIP059286 | 65.1 |
| AIP036706 | 57.6 |
| Azoxystrobin (0.5 ppm) | 99.8 |

Example 3: Evaluation of Bacterial Strains Against Late Blight on Tomato

Tomato cultivar Money Maker was used in a detached leaf assay to evaluate the bacterial strains of interest. Fully expanded leaflets from 4-5-week-old tomato plants were excised and made into disks of equal sizes using a 3.5-cm diameter cork borer. To prepare the inoculum, *P. infestans*, genotype US-23, isolated from tomatoes in North Carolina (obtained from the Dr. Ristaino Laboratory at North Carolina. State University). A 2-week-old actively growing culture was flooded with sterile distilled water and mycelium scrapped off. The mycelial suspension was then ruptured for consistency.

Each of the bacterial strains of interest was streaked onto Luria Bertani (LB) agar petri plates. A single colony was picked and placed in 50 ml of LB liquid medium or in liquid culture (CHA medium; per L, NaCl (5 g), tryptone (10 g), nutrient broth (8 g), $CaCl_2$ (0.14 mM), $MgCl_2 \cdot 6H_2O$ (0.2 mM), and $MnCl_2 \cdot 4H_2O$ (0.01 mM)) in a 250-ml flask. Cultures were harvested after 48 hours by pelleting cells and re-suspending to the original volume in deionized sterile water. Each culture was titered to determine CFU/mL using standard dilution plate count methods and plates were inspected for signs of contamination. Sterile distilled water was added to achieve a final concentration needed for strain evaluation.

Leaf disks (3.5-cm diameter each) were sprayed with 120 µL of the bacterial strain ($1 \times 10^8$ CFU/ml, suspended in magnesium chloride buffer) using a ribbed skirt fine mist fingertip sprayer (ID-5009, Container &. Packaging Supply, Eagle, ID) fitted to a 15 mL conical centrifuge tube (Fisher Scientific, Cat No. 14-59-53A). Leaf disks were inoculated with a 30 µL droplet of *P. infestans* mycelial suspension, 24 hours after application of the bacterial strain. The leaf disks were placed abaxial side in contact with a saturated double layer of Whatman™3 MM chromatography paper, 20×20 cm (Fisher Scientific Cat No. 3030-861), in a plastic container (BlisterBox P5887, 20×20 cm, Placon, Madison, WI). Boxes with leaf disks were placed inside a double zipper gallon storage bag (ZIP IGS250-448632, AEP Industrial Inc. Montvale NJ) and incubated in a growth chamber (Percival Scientific, Inc) set at a cycle of 13 hours of light and 11 h of darkness, maintained at 18° C. and 95% RH. The experimental design was a randomized complete block design with 2 replications and the experiment was repeated once.

Late blight severity was assessed after 7 days. Percent disease control indicates how well infection by the pathogen was prevented. Results are shown in Table 5.

TABLE 5

Activity of bacterial strains against *Phytophthora infestans*

| Strain ID | Disease control (%) |
|---|---|
| AIP045885 | 61.1 |
| AIP075655 | 100 |
| AIP009474 | 100 |
| AIP024525 | 91.7 |
| AIP033287 | 66.7 |
| AIP093798 | 66.7 |
| AIP061639 | 100 |
| AIP082862 | 77.8 |
| AIP058187 | 83.3 |
| AIP059286 | 100 |
| AIP036706 | 80.6 |
| Mefenoxam (5 ppm) | 75.5 |

Example 4: Evaluation of Bacterial Strains Against *Colletotrichum sublineolum* (*Sorghum* Anthracnose)

*Sorghum* cultivar 12-GS9016-KS585 was grown in the greenhouse for a steady supply of leaf tissue for the bacterial strain evaluation. Fully expanded *Sorghum* leaves from 4-6 weeks old plants were excised and cut into equal pieces, 2.5 cm wide. *Colletotrichum sublineolum*, (obtained from the Dr. Isakeit laboratory at Texas A&M University) was grown on 20% Oatmeal agar for 14 days. The actively growing culture was flooded with sterile distilled water, dislodging the spores. The concentration of the suspension was then adjusted to $1 \times 10^6$ spores/mL. Tureen 20 was then added to the suspension to 0.05%.

Each of the bacterial strains of interest was streaked onto Luria. Bertani (LB) agar petri plates. A single colony was picked and placed in 50 ml of LB liquid medium or in liquid culture (CHA medium; per L, NaCl (5 g), tryptone (10 g), nutrient broth (8 g), $CaCl_2$ (0.14 mM), $MgCl_2 \cdot 6H_2O$ (0.2 mM), and $MnCl_2 \cdot 4H_2O$ (0.01 mM)) in a 250-ml flask). Cultures were harvested after 48 hours by pelleting cells and re-suspending to the original volume in deionized sterile water. Each culture was titered to determine CFU/mL using standard dilution plate count methods and plates were inspected for signs of contamination. Sterile distilled water was added to achieve a final concentration needed for strain evaluation.

Leaf pieces were sprayed with 120 µL of each bacterial strain ($1 \times 10^8$ CFU/mL, suspended in magnesium chloride buffer) using a ribbed skirt fine mist fingertip sprayer (ID-5009, Container & Packaging Supply, Eagle, ID), fitted to a 15 mL conical centrifuge tube (Fisher Scientific, Cat No. 14-59-53A). The treated leaf pieces were then plated on 1% water agar amended with 6-Benzylaminopurine (BAP) and incubated at room temperature in the dark. 24 hours post treatment, the leaf pieces were inoculated with a 30 µL droplet of *C. sublineolum* spore suspension, applied on each side of the mid-rib. The plates were then incubated in a growth chamber (Percival Scientific, Inc) set at 12 hours photoperiod, maintained at 25° C. and 95% relative humidity. The experimental design was a randomized complete block design with 2 replications and the experiment was repeated twice.

Anthracnose severity was assessed on a scale of 0-4 after 7 days according to Prom et al., 2016 (Plant Path J. 15(1): 11-16), with few modifications. 0=No symptoms or chlorotic flecks; 1=hypersensitive reaction with no acervuli; 2=lesions with minute and few acervuli; 3=lesions with minute and few acervuli ≤25% of the leaf tissue; and 4=lesions with acervuli covering ≥25% of the leaf surface. Results (Table 6) were analyzed using analysis of variance (ANOVA) in JMP® (version 13.2.1; SAS Institute Inc., Cary, NC) and significant differences ($P<0.05$) were observed among bacterial strains.

TABLE 6

Anthracnose disease control (%) by bacterial strains on sorghum detached leaf assay

| Strain ID | Disease control (%) |
|---|---|
| AIP045885 | 0 |
| AIP075655 | 89.9 |
| AIP009474 | 26.2 |
| AIP024525 | 50 |
| AIP033287 | 26.7 |
| AIP093798 | 66.7 |
| AIP061639 | 33.3 |
| AIP082862 | 37.5 |
| AIP058187 | 83.3 |
| AIP059286 | 60.6 |
| AIP036706 | 50 |
| Pyraclostrobin (10 ppm) | 96.7 |

Example 5: Evaluation of Bacterial Strains Against *Podosphaera xanthii* (Powdery Mildew on Cucurbits)

Leaf disks of healthy squash leaves were excised and cut into uniform leaf disks 35 mm in diameter using a large cork borer. An experimental unit consisted of a single leaf disk, each treated with a suspension of the selected bacterium. Treatments included AgBiome strains AIP061382, AIP075655, and AIP029105, and control treatments. Controls were non-inoculated and inoculated leaf disks, and the synthetic fungicide tebuconazole at 10 ppm as a positive control. Bacterial strains were prepared as described in Example 2. Each leaf disk was sprayed with 200 μL of the treatment (bacterial suspension or synthetic fungicide) on the adaxial surface 24 hours before inoculation with the pathogen, *Podosphaera xanthii* (strain obtained from Dr. McGrath laboratory, Cornell University). After treatment with the fungicide, leaf disks were incubated in the dark for 24 hours at 23° C.

Leaf disks were inoculated by spraying a $1 \times 10^6$ suspension of *P. xanthii* conidia on the treated leaf surface. Treatments were placed into sealed clear plastic boxes and incubated for six days at 25° C. with a relative humidity of 80% and a 12 hour photoperiod. Each treatment was rated on a disease severity scale from 0 to 4, with 0 being no symptoms and 4 being greater than 50% of the leaf disk covered with colonies. The number of powdery mildew colonies were also recorded for each treatment. This experiment was run once, with each treatment replicated two to three times. Data was analyzed in SAS JMP version 14.0. Results are shown in Table 7.

TABLE 7

Control of powdery mildew by bacterial strains on detached squash leaf disks.

| Strain ID | Disease control (%) |
| --- | --- |
| AIP045885 | 92 |
| AIP075655 | 92 |
| AIP009474 | 100 |
| AIP024525 | 42 |
| AIP033287 | 92 |
| AIP093798 | 100 |
| AIP061639 | 83 |
| AIP082862 | 81 |
| AIP058187 | 64 |
| AIP059286 | 36 |
| AIP036706 | 81 |
| Tebuconazole (100 ppm) | 75 |

Example 6: Evaluation of Bacterial Strains Against *Mycosphaerella fijiensis* (Black *sigatoka*)

The susceptible *Musa* cultivar Grand Nain was used. Plants were maintained in the greenhouse for a constant supply of disease-free leaves. The inoculum used in this evaluation was a *M. fijiensis* culture obtained from the International of Tropical Agriculture (IITA), Ibadan, Nigeria and was maintained on V8 Juice agar.

Smaller leaf pieces (4 cm long×3 cm wide) were cut from the excised leaf. Two leaf pieces were placed in plastic petri dishes with adaxial side on agar amended with 5 mg/liter gibberellic acid. Leaf pieces were sprayed with 120 μL of bacterial strain ($1 \times 10^8$ CFU/mL of sterile distilled water) using a fingertip sprayer. Petri dishes with leaf pieces were incubated at room temperature in the dark for 24 h. Leaf pieces were then inoculated with a mycelial suspension *M. ijiensis*. Mycelial fragments scraped from growing cultures were cut in smaller mycelial tips in sterile distilled (in 50 ml conical tubes) using a homogenizer (Omni International, Kennesaw, GA). The suspension was filtered through two layers of cheesecloth and then stirred. Tween 20 (0.05% and 0.05% Silwet L-77 (Loveland Industries Inc., Greeley, CO) were added, and using a hemacytometer, the suspension was adjusted with sterile distilled water to a concentration of $1 \times 10^6$ mycelial fragments/mi. A day after inoculation, plates were incubated in a growth chamber (Percival Scientific, Inc) set at 14 hours photoperiod, maintained at 25° C. and 90% relative humidity.

Data recorded was the most progressed stage on inoculated leaves at the time of data collection (there are six recognized stages for black *sigatoka* symptom development). Data was analyzed using analysis of variance (ANOVA) in PROC GLM of SAS (version 9.4; SAS Institute Inc., Cary, NC) and significant differences ($P<0.05$) were observed among treatments. Results are shown in Table 8.

TABLE 8

Control of black sigatoka by bacterial strains on Grand Nain leaf pieces

| Strain ID | Disease control (%) |
| --- | --- |
| AIP045885 | 83.3 |
| AIP075655 | 83.9 |
| AIP009474 | 66.7 |
| AIP024525 | 0 |
| AIP033287 | 77.8 |
| AIP093798 | 16.7 |
| AIP061639 | 50 |
| AIP082862 | 0 |
| AIP058187 | 29.2 |
| AIP059286 | 33.3 |
| AIP036706 | 8.3 |
| Mancozeb (10 ppm) | 83.7 |

Example 7: Evaluation of Bacterial Strains Against Insect Species

Example 7.1: Microbe Growth

A starter culture is prepared by filling a 96-well block with 1-ml (per well) LB media. From a freezer-stock screenmate, using pipet tips or an inoculation loop, each well of the block is inoculated with a bacterial strain. This starter culture is grown at 30° C. shaking at 225 rpms for 24 h. Assay cultures are prepared by filling two 48-well blocks with ~1.7 ml (per well) media. Twenty-five μl from each well of the starter culture is added to the assay culture blocks. Assay block are grown at 30° C. for either 24, 48 or 72 h at 225 rpms.

After growth, the assay blocks are removed from the incubator/shaker and centrifuged for 20 min at 4000 rpms to pellet the microbial content. The supernatant is then poured off so that only the pellet remained. Pellets are then re-suspended in 0.5 ml buffer and placed on ice until they are used in the assay. All microbial preparations are applied within 12 h of preparation.

Example 7.2: Colorado Potato Beetle Leaf Disc Assay

A starter culture was prepared by filling a 96-well block with 1-ml (per well) LB media. Each well of the block was inoculated with a bacterial strain. The starter culture was grown at 30° C. shaking at 225 rpm for 24 h. Assay cultures were prepared by filling two 48-well blocks with ~1.7 ml (per well) media. Twenty-five µl from each well of the starter culture was added to the assay culture blocks. Assay blocks were grown at 30° C. for either 24, 48 or 72 hrs at 225 rpm. All microbial preparations were applied within 12 h of preparation.

A single prefilter was placed in each well of a 24-well plate. 50 µl ddH2O was applied to each filter, to maintain the relative humidity throughout the experiment. Undamaged and uncurled potato leaves from a potato plant were selected for use. A #8 cork borer was used to make leaf discs. A single leaf disc was placed so the top-side of the leaf was facing up into each well of a 24-well plate. 100 µl of 1% stock solution of surfactant (Silwet ECO spreader) was added to each well containing a microbial preparation. The culture was thoroughly mixed and 40 µl was pipetted onto a potato leaf disc. The treatment was allowed to spread over the entire leaf. This process was repeated so that every bacterial treatment was applied to two leaf discs.

After treatments dried, 5-6 2nd-instar Colorado Potato Beetle (CPB) larvae were added to each well. CPB eggs were reared at the AgBiome laboratory and originate from insects purchased from the University of Maine. After adding 5-6 larvae to each well, the plates were sealed with a pressure-sensitive adhesive cover and 4 small holes were added above each well. Plates were then placed in a Percival incubator and maintained at 26° C. and 55% RH with 12/12 light:dark photoperiod for 24 h. After 24 h, plates were evaluated for the percent of each leaf disc that was consumed by the CPB larvae. Plates were then returned to the incubator. Forty-eight hours post-treatment, the plates were removed from the incubator and CPB mortality was recorded for any wells in which <20% estimated leaf consumption occurred at the 24 h read. A microbe was considered active on CPB when less than 20% of the leaf disc has been consumed and/or there was greater than 80% mortality in three or more independent repetitions. Results are set forth in Table 9. "nt" indicates that bacterial strain was not tested in the CPB leaf disc assay.

Example 7.3: Western Corn Rootworm Assay

Western corn rootworm (WCR) eggs were purchased from Crop Characteristics, Farmington, MN. 60 µl volume of whole culture microbial suspension was inoculated on the top surface of diet in wells of a 24-well plate (Cellstar, 24-well, Greiner Bio One) and allowed to dry. Each well contains 500 µl diet (modified from Marrone et al., 1985). Fifteen to twenty neonate larvae were introduced in each well using a fine tip paint brush and the plate was covered with membrane (Viewseal, Greiner Bio One). The bioassay was stored at ambient temperature and scored for mortality, growth inhibition, and/or feeding inhibition at day 4. A microbe was considered active on WCR when it has greater than 70% mortality in three or more independent repetitions. The results are set forth in Table 9.

TABLE 9

Control of insects by bacterial strains

| Strain ID | CPB | WCR |
|---|---|---|
| AIP045885 | nt | Negative |
| AIP075655 | active | Negative |

TABLE 9-continued

Control of insects by bacterial strains

| Strain ID | CPB | WCR |
|---|---|---|
| AIP009474 | nt | Negative |
| AIP024525 | nt | Negative |
| AIP033287 | Negative | Negative |
| AIP093798 | nt | Negative |
| AIP061639 | nt | Negative |
| AIP082862 | nt | Negative |
| AIP058187 | nt | Negative |
| AIP059286 | nt | Negative |
| AIP036706 | nt | Negative |

Example 8. *Rhizoctonia* Damping-Off Assay—Soybean Mock Seed Treatment/In-Furrow 11-14 day old *Rhizoctonia solani* infested grain is ground. The ground inoculum is screened through a #10 screen to remove any grain that is not ground well. The ground, screened infected grains are added to Fafard Superfine Germination media at 1.5 grams of ground inoculum to 1 liter of soil mix by volume. Germination mix, inoculum, and 1 liter of water per 75 liters of germination media are added to a cement mixer and mix until everything is well incorporated. The well incorporated media-inoculum material is placed into a secondary holding container with a lid and held at 20° C. for 18 hours before using in the assay.

606-cell planting trays are filled with inoculated germination media making sure to not pack the media too firmly. One soybean seed is sown per 606 cell, planting at a depth of 1.5 to 2 cm leaving the planting holes open if applying treatments as a liquid formulation. Individual planting cells are treated with the re-suspended strain set forth in Table 2 at 3 ml per cell/seed. The seed treatment is directly over the top of the seed. Once treatments are applied, the shake flats are shaken lightly shake to close planting holes. The planting trays are lightly watered and placed in a humidity dome on the flat. After 3-4 days, flats are checked for moisture and lightly watered as needed to ensure cells are evenly moist. The humidity dome is replaced after watering.

Data Collection and Results: After 10-12 days, the assay is evaluated to determine the number of seeds that germinated. Data is reported as the % of seeds that germinated out of a total of 6 seeds per treatment.

Example 9. Field Trials for the Various Bacterial Strains or Active Variants Thereof The various bacterial strains recited in Table 2 are applied to soybeans in the field. Treatments are applied at 16.8 Gallons/Acre with treatments applied to achieve uniform plant coverage per general treatment guidelines for ASR treatment. The first treatment is applied at R1 with a follow up treatment applied at 14 days and 28 days after first treatment. The specific treatments are outlined below.

Treatments:
1. Untreated Check
2. Inoculated Check
3. Quadris at 6.2 oz/acre
4. Quadris at 2.1 oz/acre
5. AIP045885 at 7.5 g/L
6. AIP075655 at 7.5 g/L
7. AIP009474 at 7.5 g/L
8. AIP024525 at 7.5 g/L
9. AIP033287 at 7.5 g/L 10. AIP093798 at 7.5 g/L
11. AIP061639 at 7.5 g/L
12. AIP082862 at 7.5 g/L
13. AIP058187 at 7.5 g/L
14. AIP059286 at 7.5 g/L
15. AIP036706 at 7.5 g/L Example 10. Field Trials Against Various Fungal Pests for the Various Bacterial Strains The various bacterial strains recited in Table 2 are applied to the crops listed in Table 6 in the field under the current agronomic practices as listed in Table 6 to achieve uniform plant coverage and follow proper agronomic practices. Treatments are applied preventatively and/or curatively at the appropriate timings per disease.

TABLE 6

| Crop | Pathogen | Rate | Treatment Volume | Treatment Number | Application Interval/Timing |
|---|---|---|---|---|---|
| All crops | Gray Mold | 5 g/L | 25-200 Gallons/Acre | 1 to 10 | 7 to 14 days |
| Ornamental Crops | Cercospora Leaf Spots | 5 g/L | 100-300 Gallons/Acre | 1 to 4 | 7 to 14 days |
| Soybean | Cercospora Leaf Spots | 5 g/L | 5-20 Gallons/Acre | 1 to 3 | V7, R1, R3, R5 |
| Beet, Spinach, Chard | Cercospora Leaf Spots | 5 g/L | 15-50 Gallons/Acre | 3 to 6 | 7 to 14 days |
| Solanaceous Crops | Early Blight | 5 g/L | 15-50 Gallons/Acre | 4 to 10 | 7 to 14 days |
| Grape | Powdery Mildew | 5 g/L | 15-50 Gallons/Acre | 3 to 8 | 7 to 14 days |
| Cucurbit | Powdery Mildew | 5 g/L | | 2 to 8 | 7 to 14 days |
| Turf/other grasses | Anthrancose leaf spot | 5 g/L | 87-120 Gallons/Acre | 2 to 6 | 7 to 14 days |
| Grape | Downy Mildew | 5 g/L | 50-100 Gallons/Acre | 2 to 6 | 7 to 14 days |
| Leafy Greens | Downy Mildew | 5 g/L | 25 to 75 Gallons/Acre | 2 to 6 | 7 to 14 days |
| Basil | Downy Mildew | 5 g/L | 25-75 Gallons/Acre | 2 to 6 | 7 to 14 days |
| Ornamental Plants | Late Blight | 5 g/L | 100-300 Gallons/Acre | 2 to 6 | 7 to 14 days |
| Cucurbit/Peppers | Late Blight | 5 g/L | 25-100 Gallons/Acre | 2 to 10 | 7 to 14 days |
| Solanaceous Crops | Late Blight | 5 g/L | 25-100 Gallons/Acre | 2 to 10 | 7 to 14 days |
| Soybean | Late Blight | 5 g/L | 5-20 Gallons/Acre | 1 to 3 | V4 to R5 |
| Soybean | Rust | 5 g/L | 5-20 Gallons/Acre | 1 to 4 | V4 to R5 |
| Rosacea family | Fire Blight | 5 g/L | 20-100 Gallons/Acre | 1 to 3 | Pre/Post Flower |
| Malus | Apple Scab | 5 g/L | 20-100 Gallons/Acre | 1 to 5 | 7 to 14 days |
| Stone Fruits | Brown Rot | 5 g/L | 20-100 Gallons/Acre | 1 to 3 | Pre/Post Flower and Fruit Set |
| Rice | Sheath Blight | 5 g/L | 5-20 Gallons/Acre | 1 to 3 | Prior to Canopy Closure |
| Cereals | Fusarium Head Blight | 5 g/L | 5-20 Gallons/Acre | 1 to 2 | Feekes 7, 9, and/or 10.51 |

The specific treatments are outlined below:
Foliar Pest Treatment List: Early Blight
6-10 treatments
Treatment Volume: 100 gallons/acre
Treatment List:
1. Non-Inoculated, untreated Check
2. Inoculated Check
3. Chemical control chosen by cooperator applied at label instructions
4. Biological control Serenade applied at label instructions
5. Experimental Biological Foliar treatment(s) at 5 g/L plus Capsil at 3 oz/100 gallons Example 11. Field Trials Against Various Fungal Pests for the Various Bacterial Strains or Active Variants Thereof Employing Seed Treatments The various bacterial strains recited in Table 2 are applied to the crops listed in Table 7 as seed treatments prior to being planted into the field. Bacterial strain treatments are applied for preventative control of the diseases and at the application rates in Table 8. The specific treatments are outlined below.

TABLE 7

| Soybean | Canola | Wheat | Cereal Grains |
|---|---|---|---|
| Maize | Cucurbit | Cotton | Solanaceous Crops |
| Beets | Leafy Greens | Verticillium Whilt | Sunflower oil and seed |

Seed Treatment Trial Treatment List:
1. Non-inoculated Check
2. Inoculated Check
3. Disease appropriate Seed Treatment Chemical Check chosen and applied by cooperator
5. Biological Experimental Seed Treatment(s)

TABLE 8

| Crop | Pest | Rate | Treatment Type |
|---|---|---|---|
| Row Crops/Vegetables | *Pythium* | 10e4 to 10e12 | Seed Treatment |
| Row Crops/Vegetables | *Phytophthora* | 10e4 to 10e12 | Seed Treatment |
| Row Crops/Vegetables | Fusarium Wilt | 10e4 to 10e12 | Seed Treatment |
| Row Crops/Vegetables | Soybean Death Syndrome | 10e4 to 10e12 | Seed Treatment |
| Row Crops/Vegetables | *Rhizoctonia solani* | 10e4 to 10e12 | Seed Treatment |
| Row Crops/Vegetables | Verticillium Wilt | 10e4 to 10e12 | Seed Treatment |
| Row Crops/Vegetables | Corn Stalk Rot | 10e4 to 10e12 | Seed Treatment |

Example 12. Field Trials Against Various Fungal Pests for the Various Bacterial Strains or Active Variants Thereof Employing In-Furrow Treatments The various bacterial strains or active variants thereof recited in Table 2 are applied to the crops listed in Table 8 as in-furrow treatments at time of planting as preventative control for the diseases and at the treatment rates listed in Table 9. The specific treatments are outlined below:
In-Furrow Trial Treatment List:
1. Non-inoculated Check
2. Inoculated Check
3. In-Furrow Biological Treatment(s) 5 g/L+Capsil at 6 oz/100 Gallons at 15 Gallons/Acre
4. Disease appropriate In-Furrow Chemical Check as chosen and applied by cooperator.

TABLE 9

| Crop | Pest | Rate | Treatment/Volume |
|---|---|---|---|
| Row Crops/Vegetables | *Pythium* | 5 g/L | 2 to 15 Gallons/Acre |
| Row Crops/Vegetables | *Phytophthora* | 5 g/L | 2 to 15 Gallons/Acre |
| Row Crops/Vegetables | Fusarium Wilt | 5 g/L | 2 to 15 Gallons/Acre |
| Row Crops/Vegetables | Soybean Death Syndrome | 5 g/L | 2 to 15 Gallons/Acre |
| Row Crops/Vegetables | *Rhizoctonia solani* | 5 g/L | 2 to 15 Gallons/Acre |
| Row Crops/Vegetables | Verticillium Wilt | 5 g/L | 2 to 15 Gallons/Acre |
| Row Crops/Vegetables | Corn Stalk Rot | 5 g/L | 2 to 15 Gallons/Acre |

Example 13. Biological Control Strain Seed Treatment Protocol

The seed treatment formulation is made by mixing 10 g formulated strain plus 30 ml water plus 15 ml Unicoat Polymer. The weighed out seed is placed in a sterilized mason jar. An appropriate amount of seed treatment solution based off of seed weight (0.05 ml/25 g seed), the mixture is shaken for 60 seconds or until the seeds were visually well coated. The seeds are placed into a single layer in a foil roasting pan and placed under a laminar flow hood for 1 hour or until seeds are dry. Once the seeds dry, they are placed in an air tight container and stored at RT.

Example 14. Wettable Powder Formulations

One hundred grams of cell paste from each of the strains denoted in Table 2 is mixed with 5 g of glycerol and 20 g of synthetic calcium silicate using a food processor. This material is dried at 40° C. to a water activity of less than 0.30. The dried powder formulation is stored in vacuum sealed mylar pouches at 22 C. The dried powder formulation retains pesticidal activity.

Example 15. *Pythium* Field Trials

The bacterial strains set forth in Table 2 are applied as seed treatments to Soybean variety W3103. The bacterial strains are formulated as a wettable powder as described in Example 14 and then turned into seed treatments by combining 10 g of formulated bacterial strain with 30 ml water and 15 ml Seed Coating Polymer (Unicoat) and then shaking until a uniform solution was made. The finished solution was applied to 1 kg of soybean seed and allowed to dry under a laminar flow hood for 12 hours

*Pythium* inoculum was grown on millet grain and applied via in-furrow application at 1.25 g/ft and was applied at planting with treated soybeans seeded at 130,000 seeds per acre on day 1. Whole row stand counts were taken 17 days later. The specific treatments are outlined below.
Treatments:
1. Untreated Check
2. Inoculated Check
3. Quadris at 0.4 fluid ounces/Acre
4. AIP045885 Seed Treatment
5. AIP075655 Seed Treatment
6. AIP009474 Seed Treatment
7. AIP024525 Seed Treatment
8. AIP033287 Seed Treatment
9. AIP093798 Seed Treatment
10. AIP061639 Seed Treatment
11. AIP082862 Seed Treatment
12. AIP058187 Seed Treatment
13. AIP059286 Seed Treatment
14. AIP036706 Seed Treatment

Example 16. *Rhizoctonia solani* Field Trials

The bacterial strains set forth in Table 2 are applied as seed treatments to Soybean variety W3103. The bacterial strains are each formulated as a wettable powder as noted in Example 10 and then turned into seed treatments by combining 10 g of formulated bacterial strain with 30 ml water and 15 ml Seed Coating Polymer (Unicoat) and then shaking until a uniform solution is made. The finished solution is applied to 1 kg of soybean seed and allowed to dry under a laminar flow hood for 12 hours.

*Rhizoctonia solani* inoculum is grown on *Sorghum* grain and applied via in-furrow application at 1.25 g/ft and is applied at planting with treated soybeans seeded at 130,000 seeds per acre on day 1. Whole row stand counts were taken 17 days later. The specific treatments are outlined below:

Treatments:
1. Untreated Check
2. Inoculated Check
3. Quadris at 0.4 fluid ounces/Acre
4. AIP045885 Seed Treatment
5. AIP075655 Seed Treatment
6. AIP009474 Seed Treatment
7. AIP024525 Seed Treatment
8. AIP033287 Seed Treatment
9. AIP093798 Seed Treatment
10. AIP061639 Seed Treatment
11. AIP082862 Seed Treatment
12. AIP058187 Seed Treatment
13. AIP059286 Seed Treatment
14. AIP036706 Seed Treatment

What is claimed is:

1. A method for controlling a plant pest population comprising contacting said population with a composition comprising an effective amount of a biocontrol agent, wherein the biocontrol agent comprises a *Pseudomonas chlororaphis* bacterial strain AIP059286 (Northern Region Research Laboratory (NRRL) No. B-67653), wherein said composition controls said plant pest.

2. The method of claim 1, wherein the bacterial strain is present in the composition at about $10^5$ colony forming units per gram (CFU/gram) to about $10^{12}$ CFU/gram or in about $10^5$ CFU/ml to about $10^{12}$ CFU/ml.

3. The method of claim 2, wherein said effective amount of the bacterial strain comprises at least about $10^4$ to $10^{16}$ CFU per hectare.

4. The method of claim 1, wherein the composition further comprises a pesticide, a fungicide, an insecticide, or a herbicide.

5. The method of claim 4, wherein the fungicide comprises prothioconazole, azoxystrobin, fluopicolide, chlorothalonil, fosetyl, fenhexamid, flutriafol, difenoconazole, tebuconazole, tetraconazole, pyraclostrobin, trifloxystrobin, propiconazole, fluoxastrobin, flutolanil, metconazole, or metrafenone.

6. A method for growing a plant susceptible to a plant pest comprising applying to a plant, a plant part, a seed, or an area of cultivation a biocontrol agent, wherein the biocontrol agent comprises:
   (a) an effective amount of a *Pseudomonas chlororaphis* bacterial strain AIP059286 (NRRL No. B-67653); or
   (b) an effective amount of a supernatant, fermentation product, filtrate, or extract derived from a whole cell culture of a bacterial strain deposited as NRRL No. B-67653;
   wherein said effective amount controls the plant pest.

7. The method of claim 6, wherein said effective amount of the bacterial strain comprises at least about $10^4$ to $10^{16}$ CFU per hectare.

8. A method of controlling a plant pest comprising applying to a plant, a plant part, a seed, or an area of cultivation a biocontrol agent, wherein the biocontrol agent comprises:
   (a) an effective amount of a *Pseudomonas chlororaphis* bacterial strain AIP059286 (NRRL No. B-67653); or
   (b) an effective amount of a supernatant, fermentation product, filtrate, or extract derived from a whole cell culture of a bacterial strain deposited as NRRL No. B-67653;
   wherein said effective amount controls the plant pest.

9. The method of claim 8, wherein said effective amount of the bacterial strain comprises at least about $10^4$ to $10^{16}$ CFU per hectare.

10. The method of claim 8, wherein the biocontrol agent is applied to the plant or plant part after harvest.

11. A method of treating or preventing a plant disease comprising applying to a plant or plant part having a plant pest or plant disease or at risk of developing a plant pest or plant disease:
   (a) an effective amount of a biocontrol agent comprising a *Pseudomonas chlororaphis* bacterial strain AIP059286 (NRRL No. B-67653); or
   (b) an effective amount of a supernatant, fermentation product, filtrate, or extract derived from a whole cell culture of a bacterial strain deposited as NRRL No. B-67653;
   wherein the effective amount controls the plant pest.

12. A stable spray-dried formulation comprising a biocontrol agent, wherein the biocontrol agent comprises
   (a) a *Pseudomonas chlororaphis* bacterial strain AIP059286 (NRRL No. B-67653); or
   (b) a supernatant, fermentation product, filtrate, or extract derived from a whole cell culture of a bacterial strain deposited as NRRL No. B-67653.

13. The stable spray-dried formulation of claim 12, wherein said spray-dried formulation is dried to a water activity of 0.3 or less.

14. The stable spray-dried formulation of claim 12, wherein the formulation is a wettable powder or a granule.

15. The stable spray-dried formulation of claim 12, wherein the biocontrol agent is present at about $10^5$ CFU/gram to about $10^{12}$ CFU/gram or at about $10^5$ CFU/ml to about $10^{12}$ CFU/ml.

16. The stable spray-dried formulation of claim 12, wherein the formulation further comprises a pesticide, a fungicide, an insecticide or an herbicide.

17. The stable spray-dried formulation of claim 16, wherein the fungicide comprises prothioconazole, azoxystrobin, fluopicolide, chlorothalonil, fosetyl, fenhexamid, flutriafol, difenoconazole, tebuconazole, tetraconazole, pyraclostrobin, trifloxystrobin, propiconazole, fluoxastrobin, flutolanil, metconazole, or metrafenone.

18. A coated seed comprising a seed and a coating on the seed, wherein the coating comprises a spray-dried formulation comprising a biocontrol agent, wherein the biocontrol agent comprises a *Pseudomonas chlororaphis* bacterial strain AIP059286 (NRRL No. B-67653).

19. The coated seed of claim 18, wherein the coating further comprises a pesticide, a fungicide, an insecticide or an herbicide.

20. The coated seed of claim 19, wherein the fungicide comprises prothioconazole, azoxystrobin, fluopicolide, chlorothalonil, fosetyl, fenhexamid, flutriafol, difenoconazole, tebuconazole, tetraconazole, pyraclostrobin, trifloxystrobin, propiconazole, fluoxastrobin, flutolanil, metconazole, or metrafenone.

* * * * *